(12) United States Patent
Pastrana-Rios et al.

(10) Patent No.: US 10,714,209 B2
(45) Date of Patent: Jul. 14, 2020

(54) METHOD AND SYSTEM FOR SPECTRAL DATA ANALYSIS

(71) Applicant: PROTEIN DYNAMIC SOULTIONS LLC, Wakefield, MA (US)

(72) Inventors: Belinda Pastrana-Rios, Wakefield, MA (US); Jose Javier Rodriguez-Toro, Mayaguez, PR (US)

(73) Assignee: Protein Dynamic Solutions, Inc., Wakefield, MA (US)

(*) Notice: Subject to any disclaimer, the term of this patent is extended or adjusted under 35 U.S.C. 154(b) by 0 days.

(21) Appl. No.: 16/240,441

(22) Filed: Jan. 4, 2019

(65) Prior Publication Data

US 2019/0272888 A1 Sep. 5, 2019

Related U.S. Application Data

(63) Continuation of application No. 16/071,032, filed as application No. PCT/US2017/014338 on Jan. 20, 2017.

(60) Provisional application No. 62/281,630, filed on Jan. 21, 2016.

(51) Int. Cl.
| | |
|---|---|
| G16B 15/00 | (2019.01) |
| G16B 40/00 | (2019.01) |
| G01N 21/35 | (2014.01) |
| G01N 21/25 | (2006.01) |
| G01N 21/552 | (2014.01) |

(52) U.S. Cl.
CPC ............ *G16B 15/00* (2019.02); *G01N 21/255* (2013.01); *G01N 21/35* (2013.01); *G16B 40/00* (2019.02); *G01N 21/552* (2013.01); *G01N 2021/3595* (2013.01)

(58) Field of Classification Search
None
See application file for complete search history.

(56) References Cited

U.S. PATENT DOCUMENTS

| | | |
|---|---|---|
| 8,268,628 B1 | 9/2012 | Pastrana-Rios et al. |
| 9,702,810 B1 | 7/2017 | Pastrana-Rios et al. |

FOREIGN PATENT DOCUMENTS

WO 2017184886 A1 10/2017

OTHER PUBLICATIONS

Alcaraz et al. External-Cavity QuantumCascade Laser Spectroscopy for Mid-IR Transmission Measurements of Proteins in Aqueous Solution Transmission Measurements of Proteins in Aqueous Solution. Analytical Chemistry, 2015, 87(13), p. 6980-6987 (Year: 2015).*
Noda et al. Biomedical Spectroscopy and Imaging, 109-127, 2015.*
Alcaraz, Mirta R., et al. "EC-QCL mid-IR transmission spectroscopy for monitoring dynamic changes of protein secondary structure in aqueous solution on the example of β-aggregation in alcohol-denaturated α-chymotrypsin." Analytical and bioanalytical chemistry, vol. 408, No. 15, pp. 3933-3941, Jun. 1, 2016.
International Search Report and Written Opinion dated May 15, 2017 in International (PCT) Application No. PCT/US2017/014338 (12 pages).
International Search Report and Written Opinion dated Oct. 2, 2018 in International (PCT) Application No. PCT/US2018/037122 (12 pages).
Noda, Isao. "Techniques of two-dimensional (2D) correlation spectroscopy useful in life science research" Biomedical Spectroscopy and Imaging, vol. 4, No. 2, pp. 109-127, Jan. 1, 2015.
Noda, Isao and Ozaki, Yukihiro. "Protein Research by Two-Dimensional Correlation Spectroscopy" in Two-Dimensional Correlation Spectroscopy—Applications in Vibrational and Optical Spectroscopy, John Wiley & Sons, pp. 231-244, Dec. 31, 2004.
Pullara, F., et al. "Protein aggregation/crystallization and minor structural changes: universal versus specific aspects." Biophysical Journal, vol. 93, No. 9, pp. 3271-3278, Nov. 1, 2007.
International Search Report and Written Opinion dated Oct. 2, 2018 in International (PCT) Application No. PCT/US2018/037122 (11 pages).

* cited by examiner

*Primary Examiner* — Michael L Borin
(74) *Attorney, Agent, or Firm* — Hogan Lovells US LLP

(57) ABSTRACT

Characteristics of proteins, peptides, and/or peptoids can be determined via two-dimensional correlation spectroscopy and/or two-dimensional co-distribution spectroscopies. Spectral data of the proteins, peptides, and/or peptoids can be obtained with respect to an applied perturbation. two-dimensional co-distribution analysis can be applied to generate an asynchronous co-distribution plot for the proteins, peptides, and/or peptoids to define the population of proteins in solution. In the two-dimensional asynchronous plot, a cross peak can be identified as correlating with an auto peak in the two-dimensional correlation synchronous plot associated with aggregation of the proteins, peptides, and/or peptoids. The two-dimensional asynchronous cross peak can be used to determine an order of a distributed presence of spectral intensities with respect to the applied perturbation. For example, for two wavenumbers $v_1$ and $v_2$, the value of the cross peak corresponding to the two wavenumbers can indicate a presence of spectral intensity at $v_1$ relative to the presence of spectral intensity at $v_2$.

16 Claims, 30 Drawing Sheets

Specification includes a Sequence Listing.

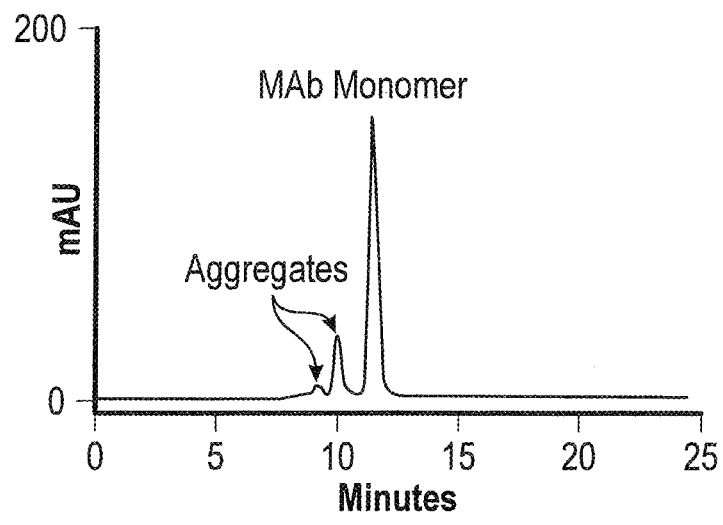
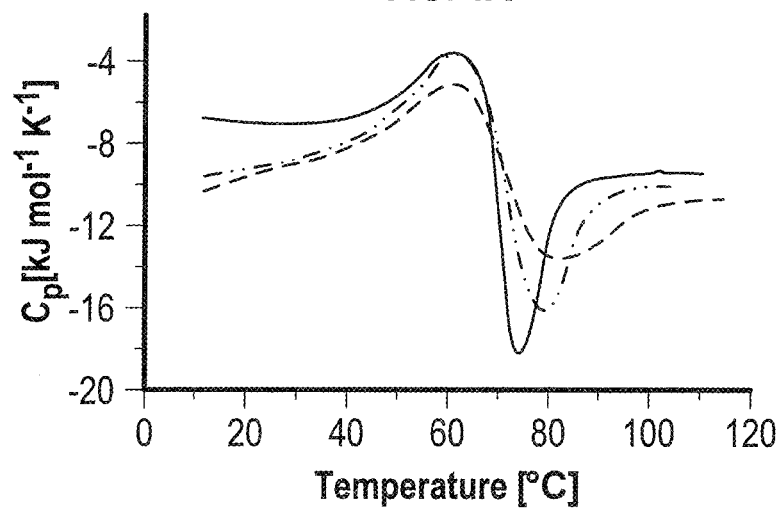
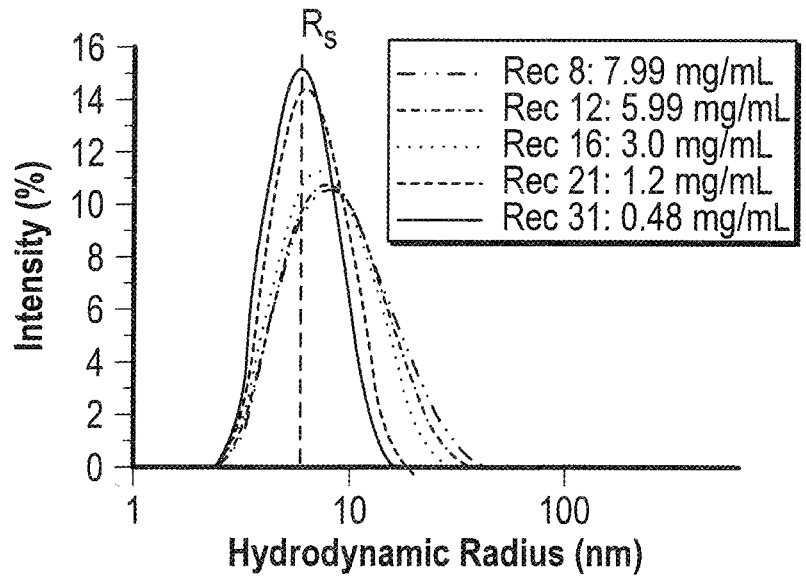
FIG. 1A
FIG. 1B
FIG. 1C

Table 1. 6 out of 20 Amino Acids are Internal Probes in $D_2O$

| Position (cm$^{-1}$) | Vibrational Mode | Side Chain | Comment |
|---|---|---|---|
| 1517 | ring bend | Y | Immediate Surrounding |
| 1545 | ν(COO-) | E | pH, Salt-bridge, H-bonding, Flexibility and Deamination |
| 1567 | ν(COO-) | D | pH, Salt-bridge, H-bonding, Deamination and Flexibility Found in β-hairpins |
| 1589 | ν$_s$(C-N) | R | Salt-bridge, H-bonding and Flexibility |
| 1609 | ν$_a$(C-N) | R | Salt-bridge, H-bonding and Flexibility |
| 1595 | Ring Bend | H | pH, H-bonding |
| 1849 | SH | C | Covalent Interaction, Oxidative Damage, Long Range Flexibility |

FIG. 7
(Continued)

```
                                  20                  40
                   |              |                   |
ADC fragment 0  APELLGGPSV FLFPPKPKDT LMISRTPEVT CVVVDVSHED PEVKFNWYVD  50
ADC fragment 1  ..□-□-□-□. ..□-□-□-□.  .........  .........  .........  . 43
ADC fragment 2  ..□-□-□-□. ..□-□-□-□C  .........  .........  .........  . 43

80              100
                                                        |               |
ADC fragment 0  GVEVHNAKTK PREEQYNSTY RVVSVLTVLH QDWLNGKEYK CKVSNKALPA  100
ADC fragment 1  .........  .........  .........  .........  .........  . 93
ADC fragment 2  .........  .........  .........  .........  .........  . 93

120
                                        |
ADC fragment 0  PIEKTISKAK HHHHHHGDYK DDDDKG  126
ADC fragment 1  .........  .........             119
ADC fragment 2  ....C....  .........             119
```

Wavenumber (cm$^{-1}$), $\nu_1$ vs Wavenumber (cm$^{-1}$), $\nu_2$

Wavenumber (cm$^{-1}$), $\nu_1$ vs Wavenumber (cm$^{-1}$), $\nu_2$

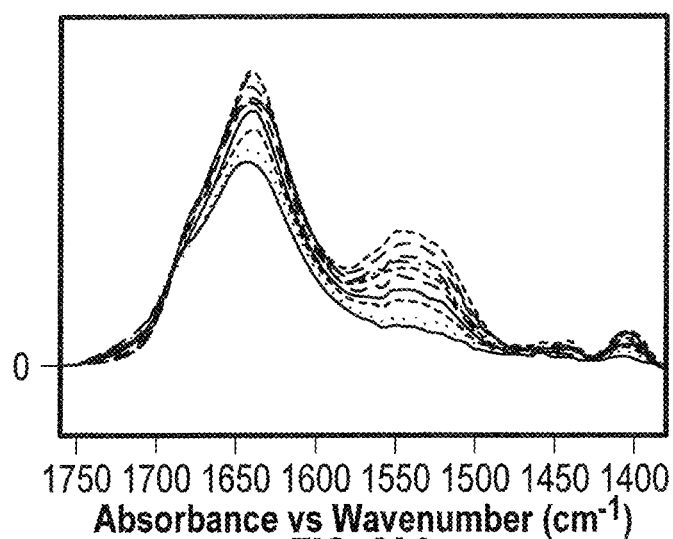
FIG. 20A
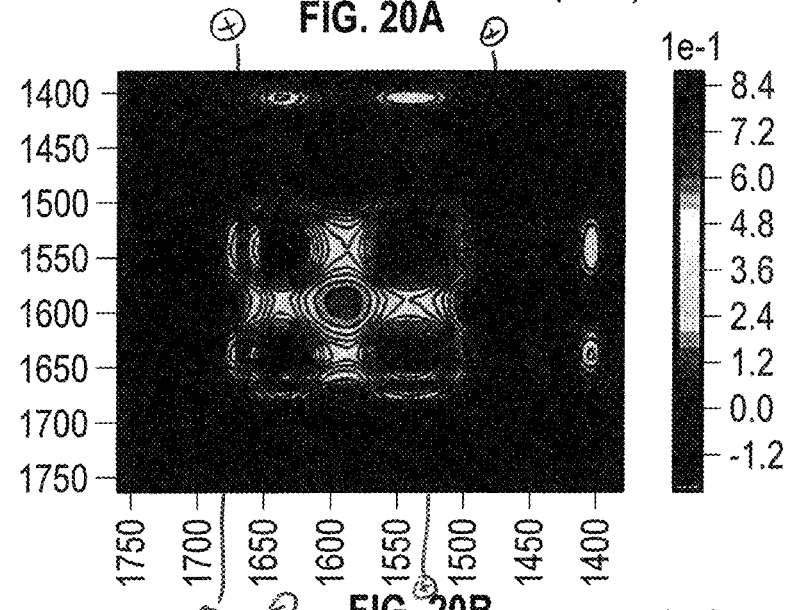
FIG. 20B
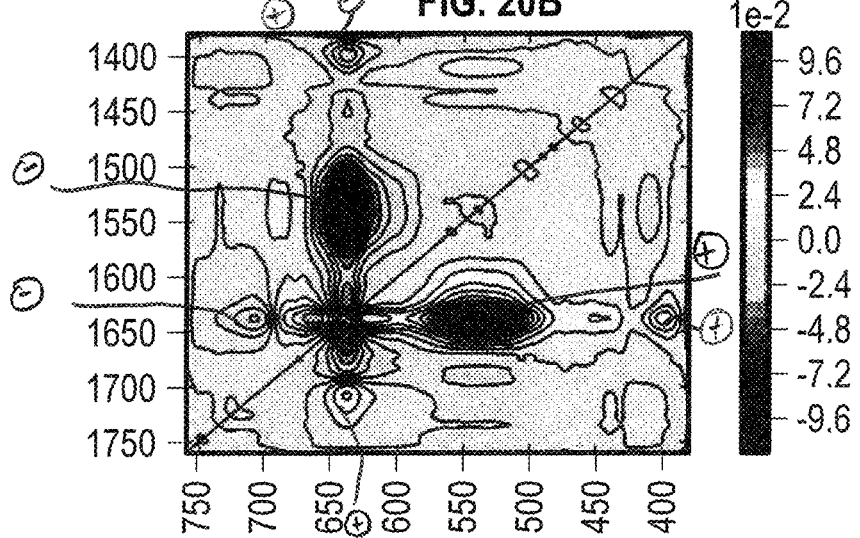
Wavenumber (cm⁻¹), $v_1$ vs Wavenumber (cm⁻¹), $v_2$   FIG. 20C FIG. 24A
FIG. 24B
FIG. 24C
FIG. 24D
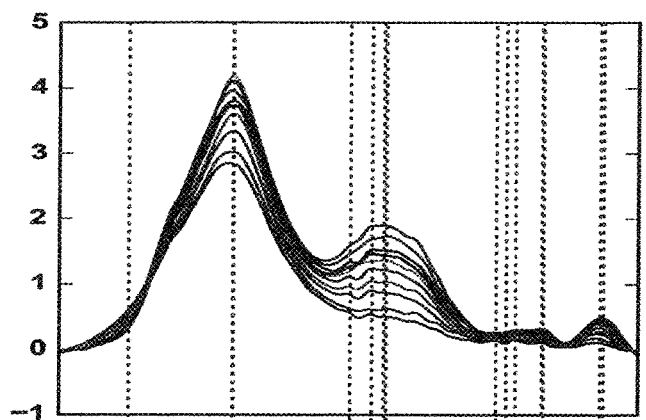
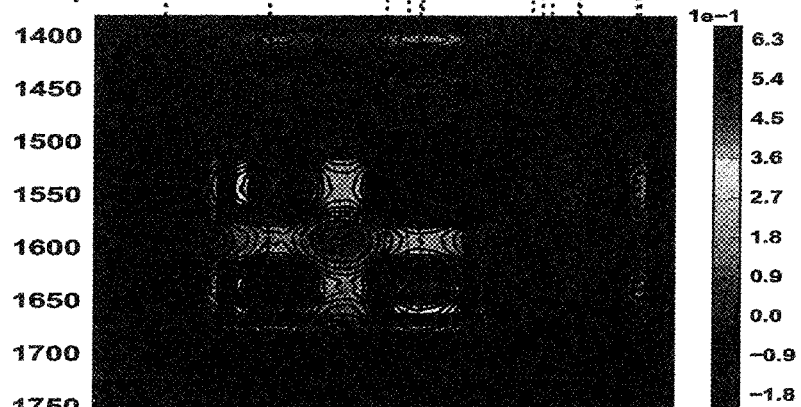
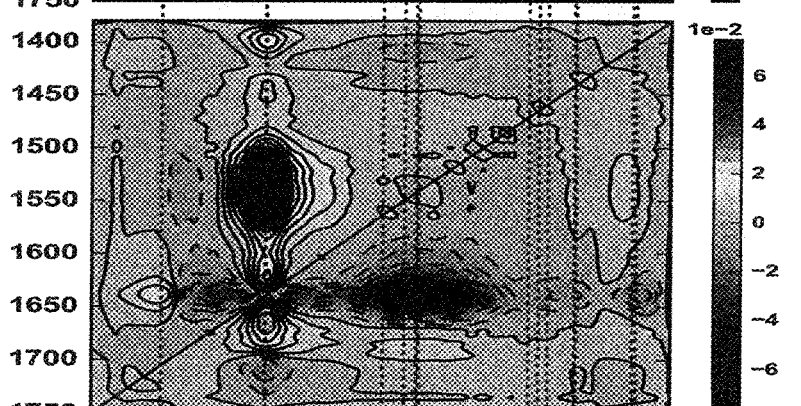
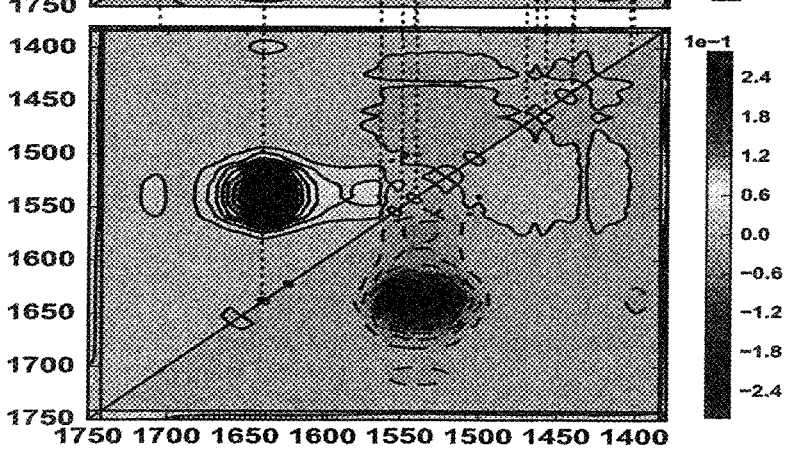

Wavenumber (cm⁻¹), $\nu_1$ vs Wavenumber (cm⁻¹), $\nu_2$

Wavenumber (cm$^{-1}$), $\nu_1$ vs Wavenumber (cm$^{-1}$), $\nu_2$

FIG. 29A Absorbance vs Wavenumber (cm⁻¹)

Wavenumber (cm⁻¹), $\nu_1$ vs Wavenumber (cm⁻¹), $\nu_2$

SEQUENCE LISTING

```
<160> NUMBER OF SEQ ID NOS: 8

<210> SEQ ID NO 1
<211> LENGTH: 126
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys His His
            100                 105                 110

His His His His Gly Asp Tyr Lys Asp Asp Asp Lys Gly
        115                 120                 125

<210> SEQ ID NO 2
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Ala Pro Glu Leu Leu Gly Gly
1               5

<210> SEQ ID NO 3
<211> LENGTH: 119
<212> TYPE: PRT
<213> ORGANISM: Artificial Sequence
<220> FEATURE:
```

<223> OTHER INFORMATION: Description of Artificial Sequence: Synthetic
      polypeptide

<400> SEQUENCE: 3

Pro Ser Val Phe Leu Phe Pro Pro Lys Pro Lys Asp Thr Leu Met Ile
1               5                   10                  15

Ser Arg Thr Pro Glu Val Thr Cys Val Val Val Asp Val Ser His Glu
            20                  25                  30

Asp Pro Glu Val Lys Phe Asn Trp Tyr Val Asp Gly Val Glu Val His
        35                  40                  45

Asn Ala Lys Thr Lys Pro Arg Glu Glu Gln Tyr Asn Ser Thr Tyr Arg
    50                  55                  60

Val Val Ser Val Leu Thr Val Leu His Gln Asp Trp Leu Asn Gly Lys
65                  70                  75                  80

Glu Tyr Lys Cys Lys Val Ser Asn Lys Ala Leu Pro Ala Pro Ile Glu
                85                  90                  95

Lys Thr Ile Ser Lys Ala Lys His His His His His His Gly Asp Tyr
            100                 105                 110

Lys Asp Asp Asp Asp Lys Gly
        115

<210> SEQ ID NO 4
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Pro Ser Val Phe Cys Phe Pro Pro Lys Pro Lys Asp Thr Leu Met Ile
1               5                   10                  15

Ser Arg Thr Pro Glu Val Thr Cys Val Val Val Asp Val Ser His Glu
            20                  25                  30

Asp Pro Glu Val Lys Phe Asn Trp Tyr Val Asp Gly Val Glu Val His
        35                  40                  45

Asn Ala Lys Thr Lys Pro Arg Glu Glu Gln Tyr Asn Ser Thr Tyr Arg
    50                  55                  60

Val Val Ser Val Leu Thr Val Leu His Gln Asp Trp Leu Asn Gly Lys
65                  70                  75                  80

Glu Tyr Lys Cys Lys Val Ser Asn Lys Ala Leu Pro Ala Pro Ile Glu
                85                  90                  95

Cys Thr Ile Ser Lys Ala Lys His His His His His His Gly Asp Tyr
            100                 105                 110

Lys Asp Asp Asp Asp Lys Gly
        115

<210> SEQ ID NO 5
<211> LENGTH: 450
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Gln Val Thr Leu Arg Glu Ser Gly Pro Ala Leu Val Lys Pro Thr Gln
1               5                   10                  15

Thr Leu Thr Leu Thr Cys Thr Phe Ser Gly Phe Ser Leu Ser Thr Ala

```
                    20                  25                  30
Gly Met Ser Val Gly Trp Ile Arg Gln Pro Gly Lys Ala Leu Glu
            35                  40                  45
Trp Leu Ala Asp Ile Trp Trp Asp Asp Lys His Tyr Asn Pro Ser
        50                  55                  60
Leu Lys Asp Arg Leu Thr Ile Ser Lys Asp Thr Ser Lys Asn Gln Val
65                  70                  75                  80
Val Leu Lys Val Thr Asn Met Asp Pro Ala Asp Thr Ala Thr Tyr Tyr
                85                  90                  95
Cys Ala Arg Asp Met Ile Phe Asn Phe Tyr Phe Asp Val Trp Gly Gln
            100                 105                 110
Gly Thr Thr Val Thr Val Ser Ser Ala Ser Thr Lys Gly Pro Ser Val
        115                 120                 125
Phe Pro Leu Ala Pro Ser Ser Lys Ser Thr Ser Gly Gly Thr Ala Ala
    130                 135                 140
Leu Gly Cys Leu Val Lys Asp Tyr Phe Pro Glu Pro Val Thr Val Ser
145                 150                 155                 160
Trp Asn Ser Gly Ala Leu Thr Ser Gly Val His Thr Phe Pro Ala Val
                165                 170                 175
Leu Gln Ser Ser Gly Leu Tyr Ser Leu Ser Ser Val Val Thr Val Pro
            180                 185                 190
Ser Ser Ser Leu Gly Thr Gln Thr Tyr Ile Cys Asn Val Asn His Lys
        195                 200                 205
Pro Ser Asn Thr Lys Val Asp Lys Arg Val Glu Pro Lys Ser Cys Asp
    210                 215                 220
Lys Thr His Thr Cys Pro Pro Cys Pro Ala Pro Glu Leu Leu Gly Gly
225                 230                 235                 240
Pro Ser Val Phe Leu Phe Pro Pro Lys Pro Lys Asp Thr Leu Met Ile
                245                 250                 255
Ser Arg Thr Pro Glu Val Thr Cys Val Val Val Asp Val Ser His Glu
            260                 265                 270
Asp Pro Glu Val Lys Phe Asn Trp Tyr Val Asp Gly Val Glu Val His
        275                 280                 285
Asn Ala Lys Thr Lys Pro Arg Glu Glu Gln Tyr Asn Ser Thr Tyr Arg
    290                 295                 300
Val Val Ser Val Leu Thr Val Leu His Gln Asp Trp Leu Asn Gly Lys
305                 310                 315                 320
Glu Tyr Lys Cys Lys Val Ser Asn Lys Ala Leu Pro Ala Pro Ile Glu
                325                 330                 335
Lys Thr Ile Ser Lys Ala Lys Gly Gln Pro Arg Glu Pro Gln Val Tyr
            340                 345                 350
Thr Leu Pro Pro Ser Arg Glu Glu Met Thr Lys Asn Gln Val Ser Leu
        355                 360                 365
Thr Cys Leu Val Lys Gly Phe Tyr Pro Ser Asp Ile Ala Val Glu Trp
    370                 375                 380
Glu Ser Asn Gly Gln Pro Glu Asn Asn Tyr Lys Thr Thr Pro Pro Val
385                 390                 395                 400
Leu Asp Ser Asp Gly Ser Phe Phe Leu Tyr Ser Lys Leu Thr Val Asp
                405                 410                 415
Lys Ser Arg Trp Gln Gln Gly Asn Val Phe Ser Cys Ser Val Met His
            420                 425                 430
Glu Ala Leu His Asn His Tyr Thr Gln Lys Ser Leu Ser Leu Ser Pro
        435                 440                 445
```

Gly Lys
    450

<210> SEQ ID NO 6
<211> LENGTH: 213
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

Asp Ile Gln Met Thr Gln Ser Pro Ser Thr Leu Ser Ala Ser Val Gly
1               5                   10                  15

Asp Arg Val Thr Ile Thr Cys Ser Ala Ser Ser Arg Val Gly Tyr Met
            20                  25                  30

His Trp Tyr Gln Gln Lys Pro Gly Lys Ala Pro Lys Leu Leu Ile Tyr
        35                  40                  45

Asp Thr Ser Lys Leu Ala Ser Gly Val Pro Ser Arg Phe Ser Gly Ser
    50                  55                  60

Gly Ser Gly Thr Glu Phe Thr Leu Thr Ile Ser Ser Leu Gln Pro Asp
65                  70                  75                  80

Asp Phe Ala Thr Tyr Tyr Cys Phe Gln Gly Ser Gly Tyr Pro Phe Thr
                85                  90                  95

Phe Gly Gly Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 7
<211> LENGTH: 583
<212> TYPE: PRT
<213> ORGANISM: Bos taurus

<400> SEQUENCE: 7

Asp Thr His Lys Ser Glu Ile Ala His Arg Phe Lys Asp Leu Gly Glu
1               5                   10                  15

Glu His Phe Lys Gly Leu Val Leu Ile Ala Phe Ser Gln Tyr Leu Gln
            20                  25                  30

Gln Cys Pro Phe Asp Glu His Val Lys Leu Val Asn Glu Leu Thr Glu
        35                  40                  45

Phe Ala Lys Thr Cys Val Ala Asp Glu Ser His Ala Gly Cys Glu Lys
    50                  55                  60

Ser Leu His Thr Leu Phe Gly Asp Glu Leu Cys Lys Val Ala Ser Leu
65                  70                  75                  80

```
Arg Glu Thr Tyr Gly Asp Met Ala Asp Cys Cys Lys Gln Glu Pro
                    85                  90                  95

Glu Arg Asn Glu Cys Phe Leu Ser His Lys Asp Asp Ser Pro Asp Leu
            100                 105                 110

Pro Lys Leu Lys Pro Asp Pro Asn Thr Leu Cys Asp Glu Phe Lys Ala
        115                 120                 125

Asp Glu Lys Lys Phe Trp Gly Lys Tyr Leu Tyr Glu Ile Ala Arg Arg
130                 135                 140

His Pro Tyr Phe Tyr Ala Pro Glu Leu Leu Tyr Tyr Ala Asn Lys Tyr
145                 150                 155                 160

Asn Gly Val Phe Gln Glu Cys Cys Gln Ala Glu Asp Lys Gly Ala Cys
                165                 170                 175

Leu Leu Pro Lys Ile Glu Thr Met Arg Glu Lys Val Leu Thr Ser Ser
            180                 185                 190

Ala Arg Gln Arg Leu Arg Cys Ala Ser Ile Gln Lys Phe Gly Glu Arg
        195                 200                 205

Ala Leu Lys Ala Trp Ser Val Ala Arg Leu Ser Gln Lys Phe Pro Lys
    210                 215                 220

Ala Glu Phe Val Glu Val Thr Lys Leu Val Thr Asp Leu Thr Lys Val
225                 230                 235                 240

His Lys Glu Cys Cys His Gly Asp Leu Leu Glu Cys Ala Asp Asp Arg
                245                 250                 255

Ala Asp Leu Ala Lys Tyr Ile Cys Asp Asn Gln Asp Thr Ile Ser Ser
            260                 265                 270

Lys Leu Lys Glu Cys Cys Asp Lys Pro Leu Leu Glu Lys Ser His Cys
        275                 280                 285

Ile Ala Glu Val Glu Lys Asp Ala Ile Pro Glu Asn Leu Pro Pro Leu
    290                 295                 300

Thr Ala Asp Phe Ala Glu Asp Lys Asp Val Cys Lys Asn Tyr Gln Glu
305                 310                 315                 320

Ala Lys Asp Ala Phe Leu Gly Ser Phe Leu Tyr Glu Tyr Ser Arg Arg
                325                 330                 335

His Pro Glu Tyr Ala Val Ser Val Leu Leu Arg Leu Ala Lys Glu Tyr
            340                 345                 350

Glu Ala Thr Leu Glu Glu Cys Cys Ala Lys Asp Asp Pro His Ala Cys
        355                 360                 365

Tyr Ser Thr Val Phe Asp Lys Leu Lys His Leu Val Asp Glu Pro Gln
    370                 375                 380

Asn Leu Ile Lys Gln Asn Cys Asp Gln Phe Glu Lys Leu Gly Glu Tyr
385                 390                 395                 400

Gly Phe Gln Asn Ala Leu Ile Val Arg Tyr Thr Arg Lys Val Pro Gln
                405                 410                 415

Val Ser Thr Pro Thr Leu Val Glu Val Ser Arg Ser Leu Gly Lys Val
            420                 425                 430

Gly Thr Arg Cys Cys Thr Lys Pro Glu Ser Glu Arg Met Pro Cys Thr
        435                 440                 445

Glu Asp Tyr Leu Ser Leu Ile Leu Asn Arg Leu Cys Val Leu His Glu
    450                 455                 460

Lys Thr Pro Val Ser Glu Lys Val Thr Lys Cys Cys Thr Glu Ser Leu
465                 470                 475                 480

Val Asn Arg Arg Pro Cys Phe Ser Ala Leu Thr Pro Asp Glu Thr Tyr
                485                 490                 495
```

```
Val Pro Lys Ala Phe Asp Glu Lys Leu Phe Thr Phe His Ala Asp Ile
            500                 505                 510

Cys Thr Leu Pro Asp Thr Glu Lys Gln Ile Lys Lys Gln Thr Ala Leu
            515                 520                 525

Val Glu Leu Leu Lys His Lys Pro Lys Ala Thr Glu Glu Gln Leu Lys
            530                 535                 540

Thr Val Met Glu Asn Phe Val Ala Phe Val Asp Lys Cys Cys Ala Ala
545                 550                 555                 560

Asp Asp Lys Glu Ala Cys Phe Ala Val Glu Gly Pro Lys Leu Val Val
                565                 570                 575

Ser Thr Gln Thr Ala Leu Ala
            580

<210> SEQ ID NO 8
<211> LENGTH: 129
<212> TYPE: PRT
<213> ORGANISM: Unknown
<220> FEATURE:
<223> OTHER INFORMATION: Description of Unknown:
      Lysozyme sequence

<400> SEQUENCE: 8

Lys Val Phe Gly Arg Cys Glu Leu Ala Ala Ala Met Lys Arg His Gly
1               5                   10                  15

Leu Asp Asn Tyr Arg Gly Tyr Ser Leu Gly Asn Trp Val Cys Ala Ala
            20                  25                  30

Lys Phe Glu Ser Asn Phe Asn Thr Gln Ala Thr Asn Arg Asn Thr Asp
            35                  40                  45

Gly Ser Thr Asp Tyr Gly Ile Leu Gln Ile Asn Ser Arg Trp Trp Cys
        50                  55                  60

Asn Asp Gly Arg Thr Pro Gly Ser Arg Asn Leu Cys Asn Ile Pro Cys
65                  70                  75                  80

Ser Ala Leu Leu Ser Ser Asp Ile Thr Ala Ser Val Asn Cys Ala Lys
                85                  90                  95

Lys Ile Val Ser Asp Gly Asn Gly Met Asn Ala Trp Val Ala Trp Arg
            100                 105                 110

Asn Arg Cys Lys Gly Thr Asp Val Gln Ala Trp Ile Arg Gly Cys Arg
            115                 120                 125

Leu
```

METHOD AND SYSTEM FOR SPECTRAL DATA ANALYSIS

RELATED APPLICATIONS

This application is a continuation of, and claims the benefit of and priority to, U.S. patent application Ser. No. 16/071,032, entitled "METHOD AND SYSTEM FOR SPECTRAL DATA ANALYSIS," filed Jul. 18, 2018, which is a National Stage application under 35 U.S.C. 371 of PCT International Application No. PCT/US2017/014338, filed Jan. 20, 2017, which claims the benefit of U.S. Provisional Application No. 62/281,630, filed Jan. 21, 2016, the entirety of each of which are hereby incorporated by reference.

SEQUENCE LISTING

The instant application contains a Sequence Listing which has been filed electronically in ASCII format and is hereby incorporated by reference in its entirety. Said ASCII copy, created on Mar. 28, 2019, is named 098210-0054_SL.txt and is 16,327 bytes in size.

BACKGROUND

Protein aggregation phenomena are prevalent throughout the industrial bioprocess. Proteins are expensive to express, isolate, and purify due to their complex physical-chemical characteristics. Aggregation is considered a primary mode of protein degradation, at times leading to immunogenicity, anti-drug antibody response (ADA) in patients and a loss of efficacy. The detection and determination of protein aggregates is a major objective in the biopharmaceutical industry and other areas of scientific research. The formation of protein aggregates is important in industrial applications because they can significantly affect the production of protein therapeutics (i.e., biologics or biosimilars), effectively lowering the production yields.

SUMMARY

The subject technology is illustrated, for example, according to various aspects described below. Various examples of aspects of the subject technology are described below. These are provided as examples and do not limit the subject technology.

Aspects of the subject technology provide a method for determining aggregation in protein, peptide and/or peptoid formulation, in solution or lyophilized state without the use of probes or additives.

According to aspects of the subject technology, the protein sample is spectroscopically analyzed and the spectral data analyzed using the established method to determine viability of the protein sample. The method and/or portions thereof can be fully automated and be used for the determination of the mechanism of aggregation.

According to aspects of the subject technology, methods described herein can be applied to membrane proteins, hydrophilic proteins, peptides and peptoids as a single component or in binary or ternary mixtures with other peptides or lipid mixtures. When in mixtures, one of the components must be isotopically labeled to allow for the simultaneous detection of each component.

Aspects of the subject technology allow flexibility of the sample preparation, its potential for automation, and data analysis which have proven its utility for pharmaceutical protein formulation.

According to aspects of the subject technology, methods described herein can be applied to any protein, peptide or peptoid sample in several environments, aqueous or lipidic. Methods described herein can be used qualitatively and/or quantitatively for determining protein aggregation. Data analysis is performed through which the mechanism of protein aggregation is determined and the stability and/or viability of the protein, peptide or peptoid can be determined.

According to one aspect of the subject technology, the method involves transmission Fourier transform infrared ("FT-IR") and/or attenuated total reflectance ("ATR") spectroscopy, quantum cascade laser microscopy ("QCL"), two-dimensional correlation spectroscopy ("2DCOS"), and/or two-dimensional co-distribution spectroscopy ("2DCDS") for the analysis of these proteins, peptides or peptoids. According to aspects of the subject technology, spectral data can be obtained using any suitable method and equipment, such as a FT-IR spectrometer, FT-IR microscope, QCL spectrometer or QCL microscope. In aspects of the subject technology, it is preferred to obtain spectral data using a QCL microscope.

Methods, systems, and instructions for processing data representing a characteristic of proteins, peptides, and/or peptoids can include: obtaining spectral data of the proteins, peptides, and/or peptoids with respect to an applied perturbation; applying two-dimensional co-distribution analysis to generate an asynchronous co-distribution plot for the proteins, peptides, and/or peptoids; identifying in the asynchronous co-distribution plot a cross peak that correlates with an auto peak associated with aggregation of the proteins, peptides, and/or peptoids; and using the cross peak to determine an order of a distributed presence of spectral intensities with respect to the applied perturbation.

Using the cross peak can include: determining, for two wavenumbers $v_j$ and $v_2$, whether the cross peak corresponding to the two wavenumbers has a positive value; and when the cross peak has a positive value, determining that a presence of spectral intensity at $v_1$ is distributed within an interval of the applied perturbation that is lower than an interval within which a presence of spectral intensity at $v_2$ is distributed. Using the cross peak can include: determining, for two wavenumbers $v_1$ and $v_2$, whether the cross peak corresponding to the two wavenumbers has a negative value; and when the cross peak has a negative value, determining that a presence of spectral intensity at $v_2$ is distributed within an interval of the applied perturbation that is lower than an interval within which a presence of spectral intensity at $v_1$ is distributed.

Operations can include: applying the two-dimensional correlation analysis to generate a synchronous plot for the proteins, peptides, and/or peptoids; identifying, in the synchronous plot, synchronous peaks associated with aggregation of the proteins, peptides, and/or peptoids; and using the synchronous peaks to determine a degree of overlap of distribution patterns for spectral intensities with respect to the applied perturbation.

Operations can also include: applying two-dimensional correlation analysis, generating a synchronous plot and an asynchronous plot for the proteins, peptides, and/or peptoids; identifying, in the synchronous plot, positive cross peaks that correlate with auto peaks associated with aggregation of the proteins, peptides, and/or peptoids; and using identified peak intensities of the spectral data to determine an amount of aggregation of the proteins, peptides, and/or peptoids.

The amount of aggregation of the proteins, peptides, and/or peptoids can be compared to an order of a distributed presence of spectral intensities with respect to the applied perturbation. Regions of interest can be recognized for discrimination of particulates and solution. A size and a number of particulates can be determined to ascertain population distribution of the particulates. The spectral data can be analyzed to verify signal-to-noise ratio, perform a baseline correction, determine water vapor content, and/or determine signal intensity within a spectral region. Covariance or dynamic spectral data can be generated based on perturbation of a sample. Changes, comprising peak intensities, can be correlated in the spectral data that are in-phase with one another as obtained in the synchronous plot. Elements that change in the spectral data can be determined. An overall greatest intensity change in the spectral data can be determined. An overall smallest intensity change in the spectral data can be determined. A minimum number of underlying spectral contributions in a band, performing curve fitting analysis, and a secondary structure composition of a sample can be determined. Changes, comprising peak intensities, can be correlated in the spectral data that are out-of-phase from one another as obtained in the asynchronous plot.

Additional features and advantages of the subject technology will be set forth in the description below, and in part will be apparent from the description, or may be learned by practice of the subject technology. The advantages of the subject technology will be realized and attained by the structure particularly pointed out in the written description and claims hereof as well as the appended drawings.

It is to be understood that both the foregoing general description and the following detailed description are exemplary and explanatory and are intended to provide further explanation of the subject technology as claimed.

BRIEF DESCRIPTION OF THE DRAWINGS

The accompanying drawings, which are included to provide further understanding of the subject technology and are incorporated in and constitute a part of this description, illustrate aspects of the subject technology and, together with the specification, serve to explain principles of the subject technology.

FIGS. 1A, 1B, and 1C show results of orthogonal bioanalytical techniques used to determine protein aggregation according to some aspects of the subject technology. FIG. 1A shows a result of size exclusion chromatography ("SEC"). FIG. 1B shows a result of differential scanning calorimetry ("DSC"). FIG. 1C shows a result of dynamic light scattering ("DLS").

FIG. 9A shows QCL infrared spectral overlay for ADC0 and ADC1. FIG. 9B shows plots for 24 and 28° C., respectively. The ADC fragments were all fully H→D exchanged. Moreover, the amide I' band maximum at 24° C. corresponds to aggregated ADC1, while at 28° C. the maximum corresponds to the ADC1 in $D_2O$ solution.

FIG. 20A shows overlaid spectra showing the amide I, II and III bands for NIST mAb at 50 mg/mL in the MID IR spectral region of 1750-1400 $cm^{-1}$ acquired within the temperature range of 24-60° C. in $H_2O$.

FIGS. 20B and 20C show 2D IR correlation analysis plots (FIG. 20B: synchronous, FIG. 20C: asynchronous) for the sample of FIG. 16A.

FIGS. 24A, 24B, 24C, and 24D show reproductions of the plots of FIGS. 21A, 21B, 21C, and 22, respectively, with the addition of broken vertical lines crossing the auto peaks of the synchronous plot 2D IR correlation analysis plots (FIG. 24B).

FIG. 29A shows overlaid spectra showing both the amide I and II bands for Lysozyme at 600 mg/mL in the spectral region of 1750-1500 $cm^{-1}$ acquired within the temperature range of 24-60° C. in $H_2O$.

DETAILED DESCRIPTION

Figure 2:
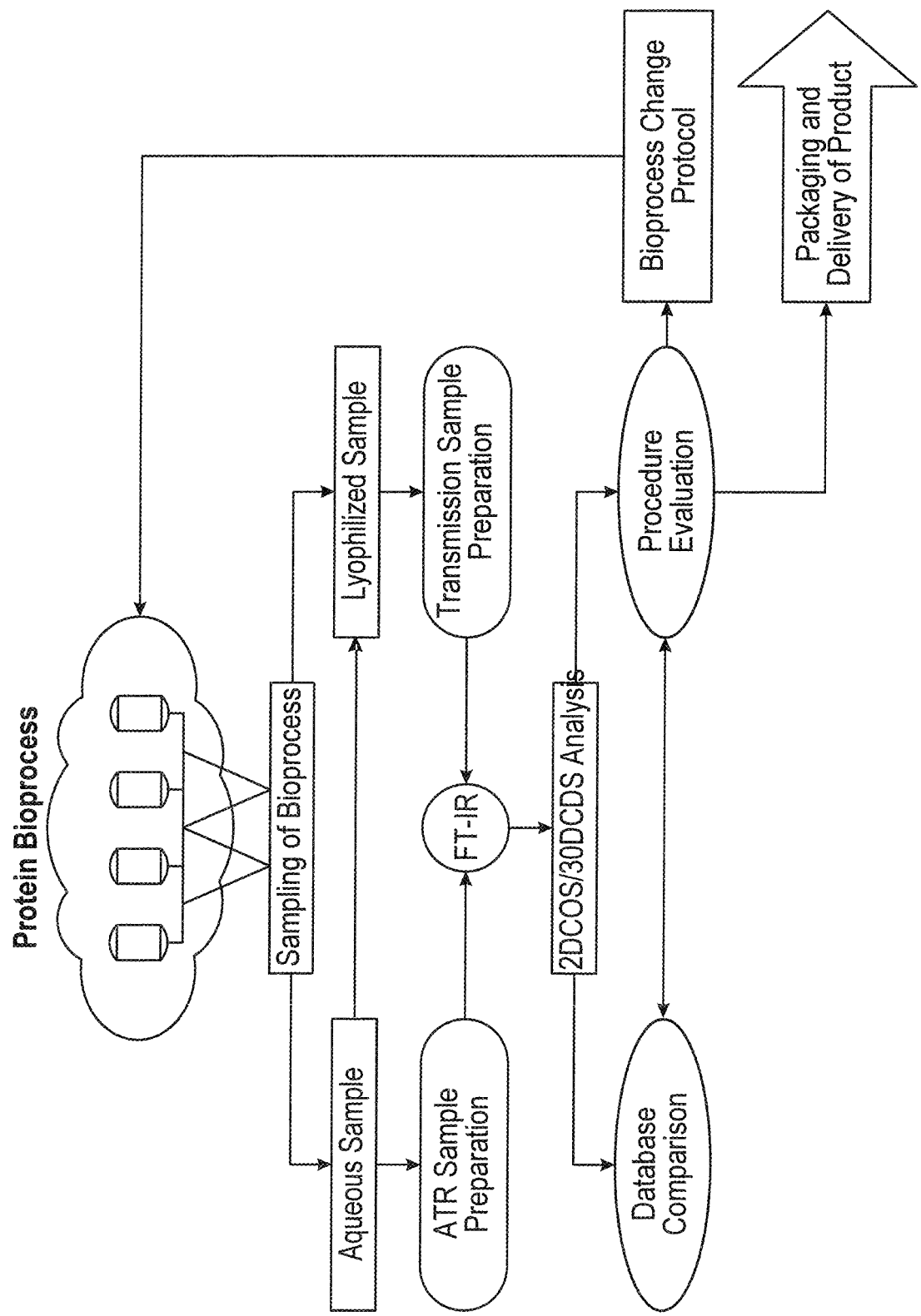
FIG. 2 shows a flowchart indicating different phases of a method according to some aspects of the subject technology.

In the following detailed description, specific details are set forth to provide an understanding of the subject technology. It will be apparent, however, to one ordinarily skilled in the art that the subject technology may be practiced without some of these specific details. In other instances, well-known structures and techniques have not been shown in detail so as not to obscure the subject technology.

Proteins are large organic compounds made of amino acids arranged in a linear chain and joined together by peptide bonds between the carboxyl and amino groups of adjacent amino acid residues. Most proteins fold into unique 3-dimensional structures. The shape into which a protein naturally folds is known as its native state. Although many proteins can fold unassisted, simply through the chemical properties of their amino acids, others require the aid of molecular chaperones to fold into their native states. There are four distinct aspects of a protein's structure:

Primary structure: the amino acid sequence.
Secondary structure: regularly repeating local structures stabilized by hydrogen bonds. Because secondary structures are local, many regions of different secondary structure can be present in the same protein molecule.
Tertiary structure: the overall shape of a single protein molecule; the spatial relationship of the secondary structures to one another.
Quaternary structure: the shape or structure that results from the interaction of more than one protein molecule, usually called protein subunits in this context, which function as part of the larger assembly or protein complex.

Proteins are not entirely rigid molecules. In addition to these levels of structure, proteins may shift between several related structures while they perform their biological function. In the context of these functional rearrangements, these tertiary or quaternary structures are usually referred to as "conformations," and transitions between them are called conformational changes.

Protein aggregation is characterized as a misfolded, rigid protein grouping which is considered a prevalent phenomenon throughout the industrial bioprocess. Aggregation is considered a primary mode of protein degradation, often leading to immunogenicity of the protein and a loss of bioactivity. Protein aggregation is of critical importance in a wide variety of biomedical situations, ranging from abnormal disease states, such as Alzheimer's and Parkinson's disease, to the production, stability and delivery of protein drugs. Protein aggregation, which could be amorphous or fibrillar in nature, can start by one of two different mechanisms: A) self-aggregation, in which the partially-folded intermediates are the immediate precursors for aggregation, and B) hetero-aggregation, in which the aggregation of one protein is mediated by another protein.

The formation of protein aggregates is critical in industrial applications, because it can highly affect the production of protein-based drugs or commercial enzymes, greatly lowering the production yields. The biologics and biosimilar industry is involved in the research, development, and manufacturing of complex drugs that include protein therapeutics. The research and development efficiency can be undesirably low, which increases costs of drug development due to the high attrition rate of protein therapeutics. The cost of protein therapeutic development is significantly impacted by late stage failure. One way to lower research and development costs is to perform a series of evaluations of the protein therapeutic candidate early in the research and development phase. By performing the characterization of the therapeutic protein under varying formulation conditions and stressors early in the research and development phase, a predictive profile of the therapeutic candidate is generated to assess the risk of protein aggregation. This approach has been defined as a developability assessment. This assessment can provide important information for decision making, such as selecting protein therapeutic candidates for further development. When protein aggregation occurs the protein therapeutic typically has decreased efficacy and can elicit an immune response. In severe cases, such an immune response can be fatal.

Several methods have been proposed in the past for the determination of aggregates in mixtures. These prior methods are either designed for a particular protein or peptide and/or require the addition of a foreign probe, and thus, do not represent a generalized method with a universal application to a class of biological molecules. Several spectroscopic techniques have been used, like UV-Vis spectroscopy with the aid of probes, fluorescence spectroscopy also using internal or exogenous probes. Similarly, near UV circular dichroism ("CD") has been used but is limited to the detection of the aggregate in its immediate vicinity, and nuclear magnetic resonance ("NMR") could be used to detect protein aggregation by the appearance of band broadening. Sedimentation analysis could also be used to identify the extent of oligomerization as long as the protein of interest has a large enough molar extinction coefficient. Chromatographic techniques such as size exclusion could also detect the presence of protein aggregates. But these techniques may require the use of exogenous probes, large amounts of protein, are time consuming and none allow for the determination of the mechanism of aggregation.

The problem of protein aggregation is complex and frequently involves several different chemical and/or computational processes, which are difficult to discern. Aggregation may be stress induced and involve physical or chemical changes such as agitation, oxidation, deamination and temperature changes. Even a slight change in pH, salt conditions, protein concentration or formulation conditions can also induce protein aggregation. Again, aggregation leads to lower yields in production, loss of efficacy of the protein therapeutic, and safety concerns in relation to immunogenicity risks. Currently available techniques to assess aggregation do not address all of the factors that are involved in the process, such as the size, identity, mechanism and extent of aggregation, and stability of the protein therapeutic in solution. Several techniques have been developed to address the size of the aggregate or particulate, yet they do not determine the identity. Other techniques can determine the size and the identity of aggregates, but cannot determine the extent of aggregation. The amino acid side chains present in a protein are important contributors to the stability of proteins. Yet, the relationship between the weak chemical interactions observed in side chains and the stability of the secondary structure of a protein can not been determined using routine bench instrumentation in a high throughput process.

The stability of the protein therapeutic is also critical for drug development, and cannot be fully characterized by simply identifying the thermal transition temperature of the protein. A greater level of understanding is needed to understand and address the stability of protein therapeutics. For example it would be beneficial to understand 1) the relative stability of the domains within the protein of interest, 2) how the amino acid side chains contribute to the stability the domains, 3) whether the amino acid side chains are involved in the aggregation mechanism, and 4) if an excipient can stabilize weak interactions (e.g., in amino acid side chains) within the critical regions in specific domains of the protein therapeutic. There is a gap in understanding parameters that are important for determining the mechanism of protein aggregation.

When currently commercially available techniques are used orthogonally, differences in the sensitivity of the available techniques is a concern. In general, such techniques focus on determining the size, purity and stability of the protein therapeutic, and evaluate the presence or absence of protein aggregates or particulates in a formulation, to achieve lot-to-lot consistency.

There is a need for technology that can be used to better assess the developability of protein therapeutics, and for the comparability assessments needed to maintain and ensure product integrity, efficacy and safety. Such a process would need to be recognized as sufficient to ensure product integrity, efficacy and safety by the Food and Drug Administration ("FDA") Center for Drug Evaluation ("CDER") division and other relevant regulatory bodies.

Solution to the protein aggregation problem for the Biopharma industry would lead to: (1) decreased R&D costs, (2) increased product yields thus ensuring its supply and demand, (3) lower risks of withdrawals, (4) increased FDA approval rates (5) reduce the time-to-market and (6) in turn increase its valuation. Also, the pipeline of new protein therapeutics is poised to address the treatment of cancer and chronic diseases such as rheumatoid arthritis, Chron's disease and neurodegenerative disorders, among others, thus improving the quality of life of patients.

Aspects of the subject technology provide a fast, accurate, and reproducible technique to determine the size, identity, mechanism, and extent of aggregation and the stability of a protein therapeutic, or other chemical, in a single experiment. Aspects of the subject technology address comparability assessment of different protein therapeutic candidates and developability assessment of protein therapeutic candidates. The data can be used for classification and chemical characterization of proteins, polymers, organic materials, inorganic materials for discovery, research and development in pilot scale or manufacturing or for quality control and assurance purposes. Also for the stability assessment during storage and delivery of the protein therapeutic.

The computational methods and systems described herein provide significant improvements over existing analysis for proteins. The computational methods and systems described herein generates and stores data in forms that facilitate efficient and meaningful analysis without requiring the use of several pieces of equipment. Accordingly, the computational methods and systems described herein can improve the efficiency of spectral data analysis for evaluation of candidate drugs.

Aspects of the subject technology include the use of two-dimensional correlation spectroscopy ("2DCOS") and two-dimensional co-distribution spectroscopy ("2DCDS") to provide essential information towards the extent and mechanism of aggregation of a protein therapeutic. The methods described herein can include analysis of the side chain modes as internal probes, offering information that confirms the stability of the structural motif or domain within proteins. The methods described herein have been shown to be useful in High Throughput-Developability and Comparability Assessment ("HT-DCA") via a Design of Experiment ("DOE") approach that complied with Quality by Design ("QBD").

According to some embodiments, systems and methods described herein can also be used to determine protein-protein interactions ("PPI's") or protein-macromolecules (protein-lipid interactions, protein DNA or protein-RNA interactions or protein drug interactions). Also, systems and methods described herein can be used for the analysis of organic solutions, polymers, gels, nanostructures or small liquid crystals, etc.

FIG. 1A shows a result of size exclusion chromatography ("SEC"), FIG. 1B shows a result of differential scanning calorimetry ("DSC"), and FIG. 1C shows a result of dynamic light scattering ("DLS"). These techniques can lead to determining the size, identity and extent of aggregation, but none can define the mechanism of aggregation. Understanding the mechanism of aggregation is fundamental to developing a protein drug that will ensure its potential to act as intended with little or no risk of immunogenicity.

According to some embodiments, for example as shown in FIG. 2, samples from different parts of a bioprocess, which could be aqueous or lyophilized, are monitored by Fourier Transform Infrared (ATR or transmission) spectroscopy ("FT-IR") and analyzed using 2DCOS in order to search for aggregates. Other types of analysis can be employed, such as Raman spectroscopy, Quantum Cascade Laser absorption, synchrotron source Fourier transform infrared microscopy, and/or combinations thereof. If aggregates are found, an evaluation procedure that might include comparing the results against an established database can be started and as a result the protocol used in the bioprocess can be modified or changed. FT-IR spectroscopy allows for a high degree of flexibility and speed in the determination of protein aggregates, with limited manipulation, and without the use of exogenous probes. An exemplary method can include FT-IR spectroscopy combined with the 2DCOS, which allows for the determination of the presence of aggregates, the determination of the mechanism of aggregation, allowing for correction in the pipeline manufacturing process of the protein to once again generate viable protein. Another exemplary method can include Quantum Cascade Laser microscopy combined with the 2DCOS, which allows for the determination of the presence of aggregates, the determination of the mechanism of aggregation, allowing for correction in the pipeline manufacturing process of the protein to once again generate viable protein. In addition, the thermal transition of the protein can also be determined and a 2DCOS plot generated to compare with the established viable protein, allowing for quality control, stability, and viability of the desired protein product. Furthermore, the ease of sample preparation and data analysis allows for the automation of this method.

FT-IR spectroscopy is sensitive to conformational changes and aggregation. This technique allows for qualitative and quantitative analysis of the extent of protein, peptide and peptoid aggregation. The use of 2DCOS allows for further analysis and provides mechanistic information related to the aggregation process. The method may incorporate one or more of the following techniques: Transmission FT-IR Spectroscopy, Attenuated Total Reflectance ("ATR") FT-IR Spectroscopy, 2DCOS analysis, and/or 2DCDS analysis.

In Transmission FT-IR microscopy or QCL microscopy, sample preparation can involve the use of pure protein, peptide or peptoid, in the appropriate buffer. The sample can be lyophilized and re-suspended in $D_2O$. The protein solution can be applied between a slide and cover and sealed to prevent solvent evaporation. The slide can be set in a slide holder. A similar procedure is used for a reference using the appropriate buffer (PBS or HEPES). A temperature probe located in close contact with the slide is used to register the temperature of the sample. A temperature gradient over time can be used and the acquired spectral data is received automatically through a thermocouple interface. During the spectral analysis the full width at half height (FWHH) of the amide I band can be determined as a function of temperature to establish the transition temperature.

Attenuated Total Reflectance (ATR) FT-IR Spectroscopy can be used for hydrogen/deuterium exchange studies, titration experiments and the determination of the orientation of reconstituted membrane proteins. In this method the protein can be fully exchanged by repeated lyophillization and redissolving the sample in $D_2O$. The fully exchanged protein sample and buffer can be spread as a film independently where the buffer is considered as the reference. Typically, a protein sample in $D_2O$ is spread onto the ATR crystal and allowed to dry, using a dry air purge. The subsequent spectrum would be representative of the protein sample and if present, the aggregated form of the protein.

According to some embodiments, spectral data can be generated by any suitable method, such as one or more of the above-described methods. A molecule to be analyzed can be provided in solution with a solute, such as water or $D_2O$, if desired. The concentration of the molecule to be analyzed in solution is preferably with a range that provides a strong signal from the molecule relative to any signal from the solute (e.g., water) or other components of the sample (i.e., a suitable signal to noise ratio), which can facilitate further analysis as described herein. Typically the concentration of a protein or peptide molecule that will provide a desired signal-to-noise ratio is related and proportional to the size of the protein or peptide. Preferred concentrations provide adequate signal-to-noise ratio for analysis. For example, as described further herein, the sample can facilitate analysis of the spectra for the molecule of interest without the need to subtract the spectra attributable to the solute (e.g., water or $D_2O$) or other components of the sample. For example, for an IgG or other protein of about 150 kD, the sample can contain the protein at a concentration of from about 50 mg/mL to about 150 mg/mL. The amount of protein can be varied from this range proportionately to the size of the protein of interest, for example, BSA which is about 67 kD can be analyzed in solution at a concentration of about 25 mg/mL to about 75 mg/mL. The sample can be provided in a cell having a path length. The path length can be longer (e.g., 30-50 μm, preferably about 40 μm) for $D_2O$ and shorter (e.g., 4-12 μm) for water.

Figure 3:
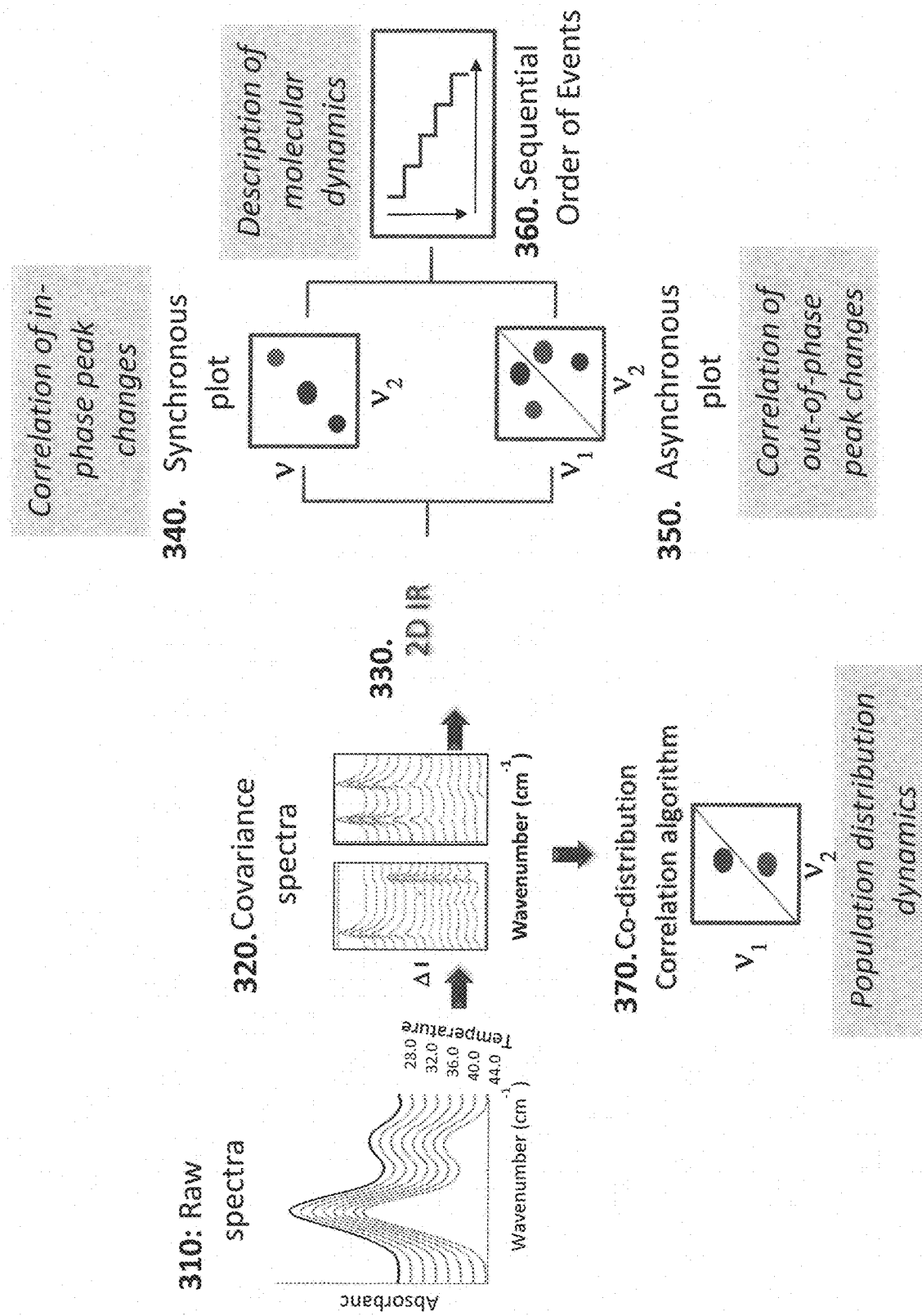
FIG. 3 shows results of a multi-stage analysis.

According to some embodiments, spectral analysis can be performed in stages, for example as illustrated in FIG. 3. The process illustrated in FIG. 3 can include stages performed as at least part of the "2DCOS/2DCDS analysis" stage illustrated in FIG. 2.

According to some embodiments, the protein sample is perturbed (thermally, chemically, pressure, or acoustics) inducing a dynamic fluctuation in the vibrational spectrum. In stage 310, raw spectra data can be collected and/or analyzed. The spectral data can be acquired at regular temperature intervals and in a sequential manner. According to some embodiments, the data can be baseline corrected.

According to some embodiments, the spectral data can be used to determine the existence of the aggregated form of the protein, peptide or peptoid. For this, the first spectrum is subtracted from the subsequent spectra to generate the dynamic spectra. In stage 320, covariance (difference) spectra can be generated by subtraction of the first spectrum (24° C.) from all subsequent spectra. Consequently, the covariance (difference) spectra contains positive and negative peaks; also referred as in- and out-of-phase from one another.

Notably the process described herein does not require the manual subtraction of water or other reference (e.g., solute) from spectral data. Such manual subtraction is a highly subjective step often incurred in protein spectral analysis. Instead, the process described herein generates the difference spectral data set based on the perturbation of the sample of interest. The output thereof can then be used for further analysis. By subtracting the first spectrum which has the overlapping water band along with the amide I band from all subsequent spectra, the spectral contributions of water are automatically subtracted.

In stage 330, a 2D IR correlation technique can be applied to generate a synchronous plot (stage 340) and an asynchronous plot (stage 350). For example, the spectral data can be fast Fourier transformed ("FFT") to generate the complex matrix from which an intensity matrix is obtained through the cross correlation product the synchronous and asynchronous plots are generated. The techniques for generating these plots will be discussed in greater detail herein.

The synchronous plot represents the intensity changes that occur during the perturbation. On the diagonal of this plot are the peaks or bands (known as auto peaks) that changed throughout the spectrum. Off the diagonal are the cross peaks which show the correlation between the auto peaks, that is, the relationship between the secondary structure changes observed. The synchronous plot can be used to relate the in-phase peak intensity changes or shifts.

In synchronous correlation spectrum, auto peaks at diagonal positions represent the extent of perturbation-induced dynamic fluctuations of spectral signals. Cross peaks represent simultaneous changes of spectral signals at two different wavenumbers, suggesting a coupled or related origin of intensity variations. If the sign of a cross peak is positive, the intensities at corresponding wavenumbers are increasing or decreasing together. If the sign is negative, one is increasing, while the other is decreasing.

The asynchronous plot contains only cross peaks which are used to determine the order of events and thus the mechanism of aggregation of the protein. The asynchronous plot can be used to relate the out-of-phase peak intensity changes or shifts.

In asynchronous correlation spectrum, cross peaks develop only if the intensity varies out of phase with each other for some Fourier frequency components of signal fluctuations. The sign of a cross peak is positive if the intensity change at wavenumber $v_2$ occurs before wavenumber $v_1$. The sign of a cross peak is negative if the intensity change at wavenumber $v_2$ occurs after wavenumber $v_1$. The above sign rules are reversed if the same asynchronous cross peak position translated to the synchronous plot falls in a negative region ($\Phi(v_1, v_2)<0$).

The 2D IR correlation enhances the spectral resolution of the underlying peaks of broad bands such as the amide I and II bands by spreading the peaks in two dimensions. These plots are symmetrical in nature, and for discussion purposes reference will be made to the top triangle for analysis. The synchronous plot (shown at 340) contains two types of peaks: (a) auto peaks that are positive peaks on the diagonal and (b) cross peaks that are off-diagonal peaks that can be either positive or negative. The asynchronous plot (shown at 350) is comprised exclusively of cross peaks that relate the out-of-phase peaks. As a result this plot reveals greater spectral resolution enhancement. The following rules can apply to establish the order of molecular events:

I. If the asynchronous cross peak, $v_2$ is positive, then $v_2$ is perturbed prior to $v_1$ ($v_2 \rightarrow v_1$).

II. If the asynchronous cross peak, $v_2$, is negative, then $v_2$ is perturbed after $v_1$. ($v_2 \rightarrow v_1$)

III. If the synchronous cross peak (off-diagonal peaks, not shown in FIG. 3) are positive, then the order of events are exclusively established using the asynchronous plot (rules I and II).

IV. If the synchronous plot contains negative cross peaks and the corresponding asynchronous cross peak is positive, then the order is reversed.

V. If the synchronous plot contains negative cross peaks and the corresponding asynchronous cross peak is negative, then the order is maintained.

The order of events can be established for each peak observed in the $v_2$ axis. A table can be provided summarizing the order for each event. In stage 360, a sequential order of events plot is generated using the table summarizing the order of each event. On top of each step (event) is the spectroscopic information of the cross peak, $v_2$ while on the bottom of each step is the corresponding peak assignment or the biochemical information for each event in the order in which they are perturbed as a function of temperature. Examples are provided herein.

Two-dimensional correlation spectroscopy ("2DCOS") analysis can be used to resolve complex bands, such as the amide I band. An example of 2DCOS analysis is described in U.S. Pat. No. 8,268,628, hereby incorporated herein by reference. The skilled artisan's attention is called to Isao Noda, "Two-dimensional co-distribution spectroscopy to determine the sequential order of distributed presence of species", Journal of Molecular Structure, Vol. 1069, pp. 51-54, which describes algorithms suitable for use in 2DCOS analysis.

A summary of the development of 2DCOS is as follows. A discretely sampled set of spectra $A(v_1, t_k)$ can be obtained for a system measured under the influence of an external perturbation, which induces changes in the observed spectral intensities. The spectral variable $v_j$ with $j=1, 2, \ldots, n$ may be for example wave-number, frequency, scattering angle, etc., and the other variable $t_k$ with $k=1, 2, \ldots, m$ represents the effect of the applied perturbation, e.g., time, temperature, and electrical potential. Only the sequentially sampled spectral data set obtained during the explicitly defined observation interval between $t_1$ and $t_m$ will be used for the 2DCOS analysis. For simplicity, wavenumber and time are used here to designate the two variables, but it is understood that use of other physical variables is also valid.

Dynamic spectrum used in 2D correlation spectroscopy is explicitly defined as $$\tilde{A}(v_j, t_k) = \begin{cases} A(v_j, t_k) - \overline{A}(v_j) & \text{for } 1 \leq k \leq m \\ 0 & \text{otherwise} \end{cases} \quad (1)$$

where $\overline{A}(v_j)$ is the spectrum of the reference state of the system. In the absence of the a priori knowledge of the reference state, the reference spectrum can also be set as the time-averaged spectrum over the observation interval between $t_1$ and $t_m$.

$$\overline{A}(v_j) = \frac{1}{m} \sum_{k=1}^{m} A(v_j, t_k) \quad (2)$$

With this specific choice of the reference spectrum, the portion of dynamic spectra within the observation interval essentially becomes equivalent to the mean-centered spectra. Synchronous and asynchronous 2D correlation spectra $\Phi(v_1, v_2)$ and $\psi(v_1, v_2)$, are given by $$\Phi(v_1, v_2) = \frac{1}{m-1} \sum_{j=1}^{m} \tilde{A}(v_1, t_j) \cdot \tilde{A}(v_2, t_j) \quad (3)$$

$$\Psi(v_1, v_2) = \frac{1}{m-1} \sum_{j=1}^{m} \tilde{A}(v_1, t_j) \cdot \sum_{l=1}^{m} N_{jl} \tilde{A}(v_2, t_l) \quad (4)$$

The term $N_{ij}$ is the element of the so-called Hilbert-Noda transformation matrix given by $$N_{ij} = \begin{cases} 0 & \text{if } i = j \\ \dfrac{1}{\pi(j-i)} & \text{otherwise} \end{cases} \quad (5)$$

Synchronous spectrum $\Phi(v_1, v_2)$ represents the coordinated or simultaneous changes of spectral intensities observed at two different wavenumbers, $v_1$ and $v_2$, along the perturbation variable $t_k$. The sign of the synchronous correlation intensity becomes positive if the spectral intensities measured at the two wavenumbers mostly change in the same direction, either increasing or decreasing. On the other hand, if one is increasing while the other is decreasing, the sign of $\Phi(v_1, v_2)$ becomes negative.

Asynchronous spectrum $\psi(v_1, v_2)$ represents the out-of-phase or sequential changes of spectral intensities. If $\psi(v_1, v_2)=0$, the variations of spectral intensities at two wavenumbers, $v_1$ and $v_2$ are completely synchronized. If the signs of $\Phi(v_1, v_2)$ and $\psi(v_1, v_2)$ are the same, the overall spectral intensity variation observed at predominantly occurs prior to that at $v_2$. If the signs are different, the order is reversed. Finally, if $\Phi(v_1, v_2)=0$, the sequential order of intensity variations cannot be determined. It is important to emphasize that 2D correlation spectra only give the sequential order of spectral intensity variations but not the order of the distributed presence of species responsible for the spectral signals.

Referring again to FIG. 3, in stage 370, a co-distribution correlation plot provides the perturbed regions of the protein population distribution (80% threshold) in solution.

Two-dimensional co-distribution spectroscopy ("2DCDS") analysis can be used to analyze a population of protein molecules that are in solution and how the different populations of these proteins behave. The skilled artisan's attention is called to Isao Noda, "Two-dimensional co-distribution spectroscopy to determine the sequential order of distributed presence of species", Journal of Molecular Structure, Vol. 1069, pp. 54-56, which describes algorithms suitable for use in 2DCDS analysis.

For a set of m time-dependent spectra $A(v_j, t_k)$ sequentially obtained during the observation interval of $t_1 \leq t_k \leq t_m$ with the time-averaged spectrum $\overline{A}(v_j)$ given by Eq. (2), the characteristic (time) index is defined as $$\overline{k}(v_j) = \frac{1}{m\overline{A}(v_j)} \sum_{k=1}^{m} k \cdot A(v_j, t_k) = \frac{1}{m\overline{A}(v_j)} \sum_{k=1}^{m} k \cdot \tilde{A}(v_j, t_k) + \frac{m+1}{2} \quad (6)$$

Dynamic spectrum $\tilde{A}(v_j, t_k)$ used here is the same as that defined in Eq. (1). The corresponding characteristic time of the distribution of spectral intensity observed at wavenumber $v_j$ is given by $$\bar{t}(v_j) = (t_m - t_1) \frac{\overline{k}(v_j) - 1}{m - 1} + t_1 \quad (7)$$

Once again, it is understood that time used here is meant to be the generic description of a representative variable of applied perturbation, so that it could be replaced with any other appropriate physical variables, such as temperature, concentration, and pressure, selected specific to the experimental condition. The characteristic time $\bar{t}(v_j)$ is the first moment (about the origin of time axis, i.e., t=0) of the distribution density of the spectral intensity $A(v_j, t_k)$ along the time axis bound by the observation interval between $t_1$ and $t_m$. It corresponds to the position of the center of gravity for observed spectral intensity distributed over the time.

Given the characteristic times, $\bar{t}(v_1)$ and $\bar{t}(v_2)$, of the time distributions of spectral intensities measured at two different wave-numbers, $v_1$ and $v_2$, the synchronous and asynchronous co-distribution spectra are defined as $$\Gamma(v_1, v_2) = \sqrt{1 - \left(\frac{\bar{t}(v_2) - \bar{t}(v_1)}{t_m - t_1}\right)^2} T(v_1, v_2) \quad (8)$$

$$\Delta(v_1, v_2) = \frac{\bar{t}(v_2) - \bar{t}(v_1)}{t_m - t_1} T(v_1, v_2) \quad (9)$$

where $T(v_1, v_2)$ is the total joint variance given by $$T(v_1, v_2) = \sqrt{\Phi(v_1, v_1) \cdot \Phi(v_2, v_2)} \quad (10)$$

Synchronous co-distribution intensity $\Gamma(v_1, v_2)$ is a measure of the co-existence or overlap of distributions of two separate spectral intensities along the time axis. In contrast, asynchronous co-distribution intensity $\Delta(v_1, v_2)$ is a measure of the difference in the distribution of two spectral signals. The term "co-distribution" denotes the comparison of two separate distributions, distinguishing this metric from the concept of "correlation" which is based on the comparison of two variations.

By combining Eqs. 6, 7, and 9, the expression for asynchronous co-distribution spectrum is given as $$\Delta(v_1, v_2) = \frac{T(v_1, v_2)}{m(m-1)} \sum_{k=1}^{m} k \left\{ \frac{A(v_2, t_k)}{\overline{A}(v_2)} - \frac{A(v_1, t_k)}{\overline{A}(v_1)} \right\} \quad (11)$$

$$= \frac{T(v_1, v_2)}{m(m-1)} \sum_{k=1}^{m} k \left\{ \frac{\tilde{A}(v_2, t_k)}{\overline{A}(v_2)} - \frac{\tilde{A}(v_1, t_k)}{\overline{A}(v_1)} \right\}$$

The value of $\Delta(v_1, v_2)$ is set to be zero, if the condition of $\overline{A}(v_1)=0$ or $\overline{A}(v_2)=0$ is encountered, which indicates the lack of spectral intensity signals at either of the wavenumber. Synchronous co-distribution spectrum can be obtained from the relationship $$\Gamma(v_1, v_2) = \sqrt{T(v_1, v_1)^2 - \Delta(v_2, v_2)^2} \quad (12)$$

In an asynchronous co-distribution spectrum, and for a cross peak with positive sign, i.e., $\Delta(v_1, v_2)$=0, the presence of spectral intensity at $v_1$ is distributed predominantly at the earlier stage along the time axis compared to that for $v_2$. On the other hand, if $\Delta(v_1, v_2)$<0, the order is reversed. In the case of $\Delta(v_1, v_2) \approx 0$, the average distributions of the spectral intensities observed at two wavenumbers over the time course are similar. Sign of synchronous co-distribution peaks is always positive, which somewhat limits the information content of synchronous spectrum beyond the obvious qualitative measure of the degree of overlap of distribution patterns.

2DCDS is capable of providing elements of the mechanism of aggregation in a protein or any process being investigated in a weighted fashion. 2DCDS can be used to directly provide the sequence of distributed presence of species along the perturbation (e.g., time, temperature, concentration, pressure, etc.) variable axis. The technique can be used as a complementary tool to augment 2DCOS analysis in directly identifying the presence of intermediate species. According to some embodiments, perturbation-dependent spectra are sequentially obtained during an observation interval. 2D correlation spectra (synchronous spectrum and asynchronous spectrum) are derived from the spectral variations. Synchronous co-distribution intensity is measured as the coexistence or overlap of distributions of two separate spectral intensities along the perturbation axis. Asynchronous co-distribution intensity is measured as the difference in the distribution of two spectral signals. For a cross peak with positive sign, i.e., $\Delta(v_1, v_2)$>0, the presence of spectral intensity at $v_1$ is distributed predominantly at the earlier stage along the time axis compared to that for $v_2$. On the other hand, if $\Delta(v_1, v_2)$<0, the order is reversed. In the case of $\Delta(v_1, v_2) \approx 0$, the average distributions of the spectral intensities observed at two wavenumbers over the time course are similar.

Differences between the 2DCOS analyses provide a mean average description of the pathway due to the perturbation process and its effect on the sample, while the 2DCDS analysis provides the weighted elements in a population of molecules (proteins) during the perturbation process. The result of 2DCOS and 2DCDS is a direct and simplified description of elements that are changing in the spectral data due to the perturbation.

Figure 4:
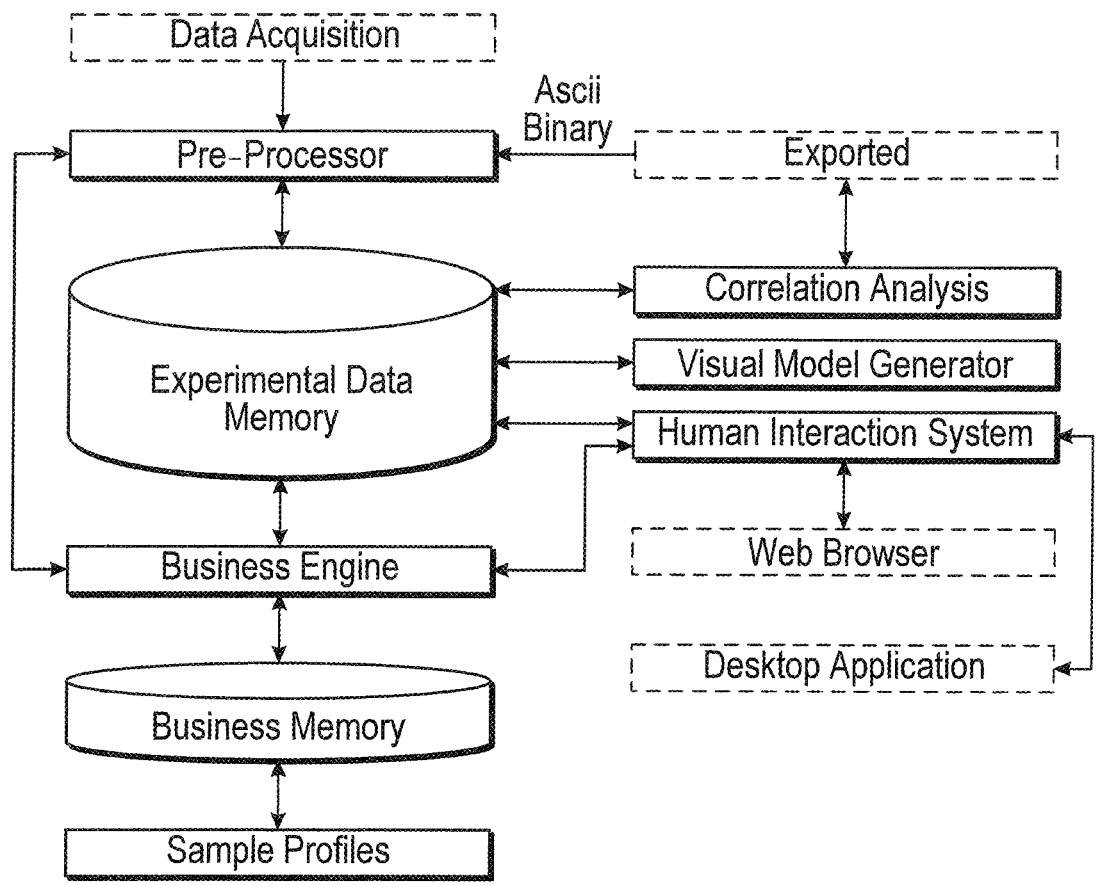
FIG. 4 shows a diagram of an exemplary computing system according to some aspects of the subject technology.

According to some embodiments, for example as shown in FIG. 4, a system for performing data analysis can include at least the components shown for performing functions of methods described herein. Acquired data can be provided to one or more computing units, including processors, for analysis. Modules can be provided to perform or manage analysis of the data. Such modules can include a correlation analysis module, a visual model generator module, and/or a human interaction module. The modules may be in communication with one another. In some embodiments, the modules may be implemented in software (e.g., subroutines and code). For example, the modules may be stored in memory and/or data storage, and executed by a processor. In some aspects, some or all of the modules may be implemented in hardware (e.g., an Application Specific Integrated Circuit (ASIC), a Field Programmable Gate Array (FPGA), a Programmable Logic Device (PLD), a controller, a state machine, gated logic, discrete hardware components, or any other suitable devices), firmware, software, and/or a combination thereof. Additional features and functions of these modules according to various aspects of the subject technology are further described in the present disclosure.

Figure 5:
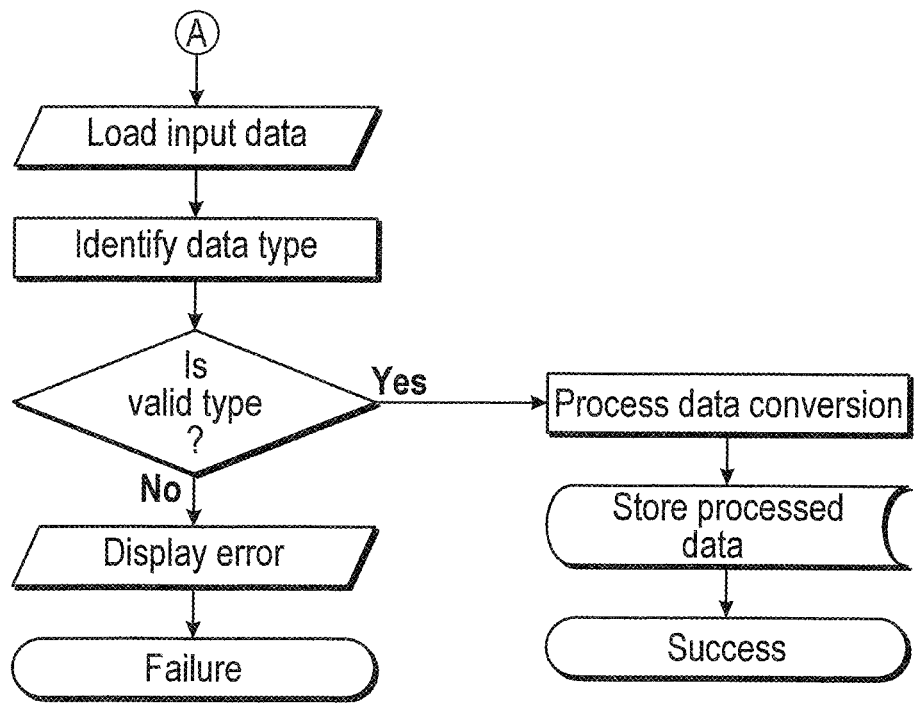
FIG. 5 shows a flowchart indicating operations of an exemplary method according to some aspects of the subject technology.

According to some embodiments, for example as shown in FIG. 5, a method for verifying and preparing acquired data can be performed. The type of data is identified and verified. Based on the verification, the data can be converted and/or stored or rejected with an error displayed to a user.

Figure 6:
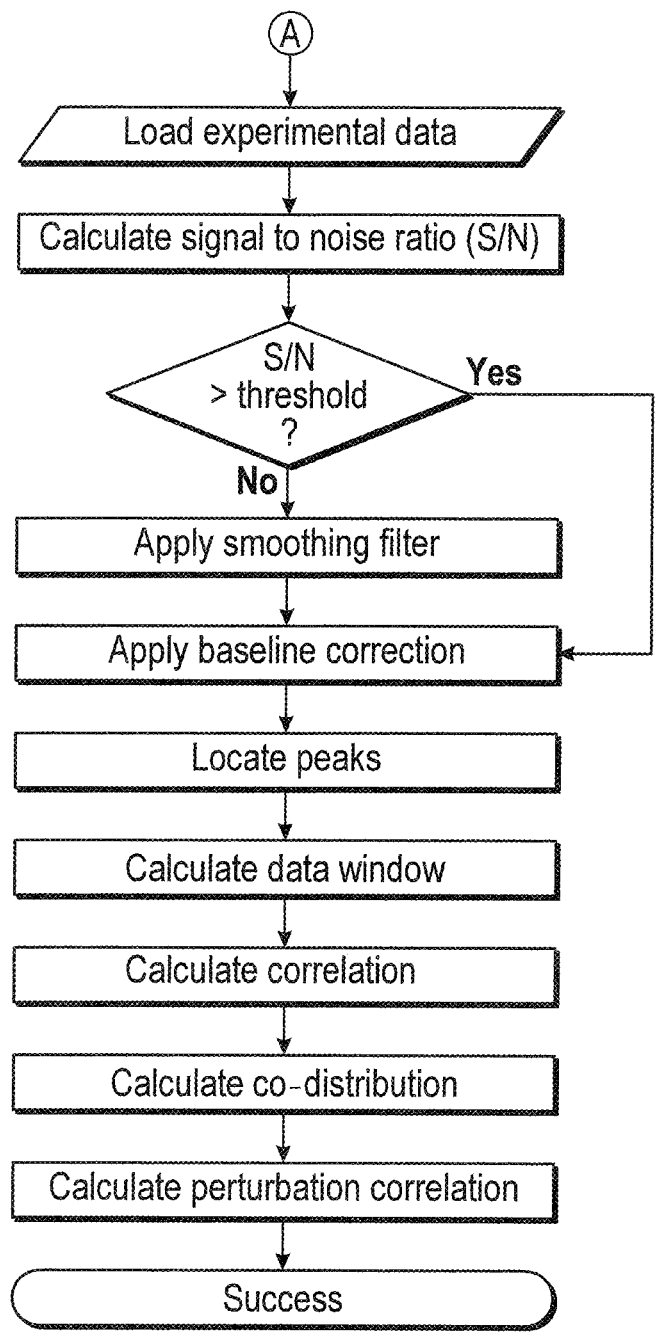
FIG. 6 shows a flowchart indicating operations of an exemplary method according to some aspects of the subject technology.

According to some embodiments, for example as shown in FIG. 6, a method for analyzing acquired data can be performed. The type of data is verified for adequate signal-to-noise ratio relative to a threshold. Based on the verification, the data can be subject to analysis or smoothing filter process before the analysis.

According to some embodiments, for example as shown in FIG. 6, the data can be analyzed in operations that include applying a baseline correlation, locating peaks, calculating data windows, calculating correlations, calculating co-distributions, and/or calculating perturbation correlation.

Data manipulation can include auto recognition of regions of interest (ROI) for the discrimination of particulates and solution. The size and number of the particulates can be determined to ascertain population distribution of particulates. Data manipulation can be performed to ensure compliance such as S/N ratio determination, baseline correction, determine water vapor content, and determine signal intensity of the elements of interest within the spectral region studied. Data output for statistical analysis can be simplified using, inter alia, the Design of Experiment approach. The intensity and spectral position of the elements of interest can be output as comma delimited files (*.csv). Covariance, or dynamic spectral data sets can be generated based on the perturbation of the sample of interest, the output of which can be used for further analysis. For example, data output can be provided in a format that facilitates merging with other bioanalytical results for comparability assessment and sourced by: perturbation type, excipient, protein therapeutic, protein concentration, temperature, date of acquisition, and/or bioanalytical technique. This approach would allow for the statistical analysis to be performed for all of the experiments that were carried-out under similar conditions. More importantly, the results of the DOE analysis would be a standalone document ready for final reporting and allow for decision making.

According to some embodiments, methods and systems described herein can apply a correlation function to the covariance or the dynamic spectral data to generate two plots (Synchronous and Asynchronous) this algorithm is termed 2D IR correlation spectroscopy. The changes (e.g., peak intensities) in the spectral data that are in-phase with one another can be correlated as obtained in the synchronous plot. The elements that change in the spectral data can be determined. The overall greatest intensity change in the spectral data can be determined. The overall smallest intensity change in the spectral data can be determined. The minimum number of underlying spectral contribution in a broad band such as the amide band for proteins and peptides can be determined for curve fitting analysis, which allows for the determination of secondary structure composition. The resolution of the spectral region being studied can be enhanced, particularly for broad bands in the spectra.

The changes (e.g., peak intensities) in the spectral data that are out-of-phase from one another can be correlated as obtained in the asynchronous plot. The asynchronous plot also contains the order of events that describe in molecular detail the protein behavior. A detailed evaluation of the plots could be performed to ascertain the order of events. Alternatively or in combination, this process can be automated. A joint variance function can be applied to the covariance or dynamic spectral data to generate the merged asynchronous plot which can be interpreted directly to determine the order of events. This method can alternatively be used to validate the above interpretations for the description of the molecular behavior of a protein which is a complex description. Further information for the curve-fitting routine, the input of the number position and intensity information for the curve-fitting routine could also be an automated process yielding the secondary structure composition of the protein and the extent of protein aggregated species in the samples analyzed. The intensity information from the 2D IR correlation plots can be used for the quantitative determination of oxidative products, such as deamination. For example, deamination can be detected based on side chins. Such analysis can be used for candidate drug selection or during a protein design phase. A machine learning approach can be implemented as a long term solution to the complexity of the attributes needed to be correlated and solved.

Figure 7:
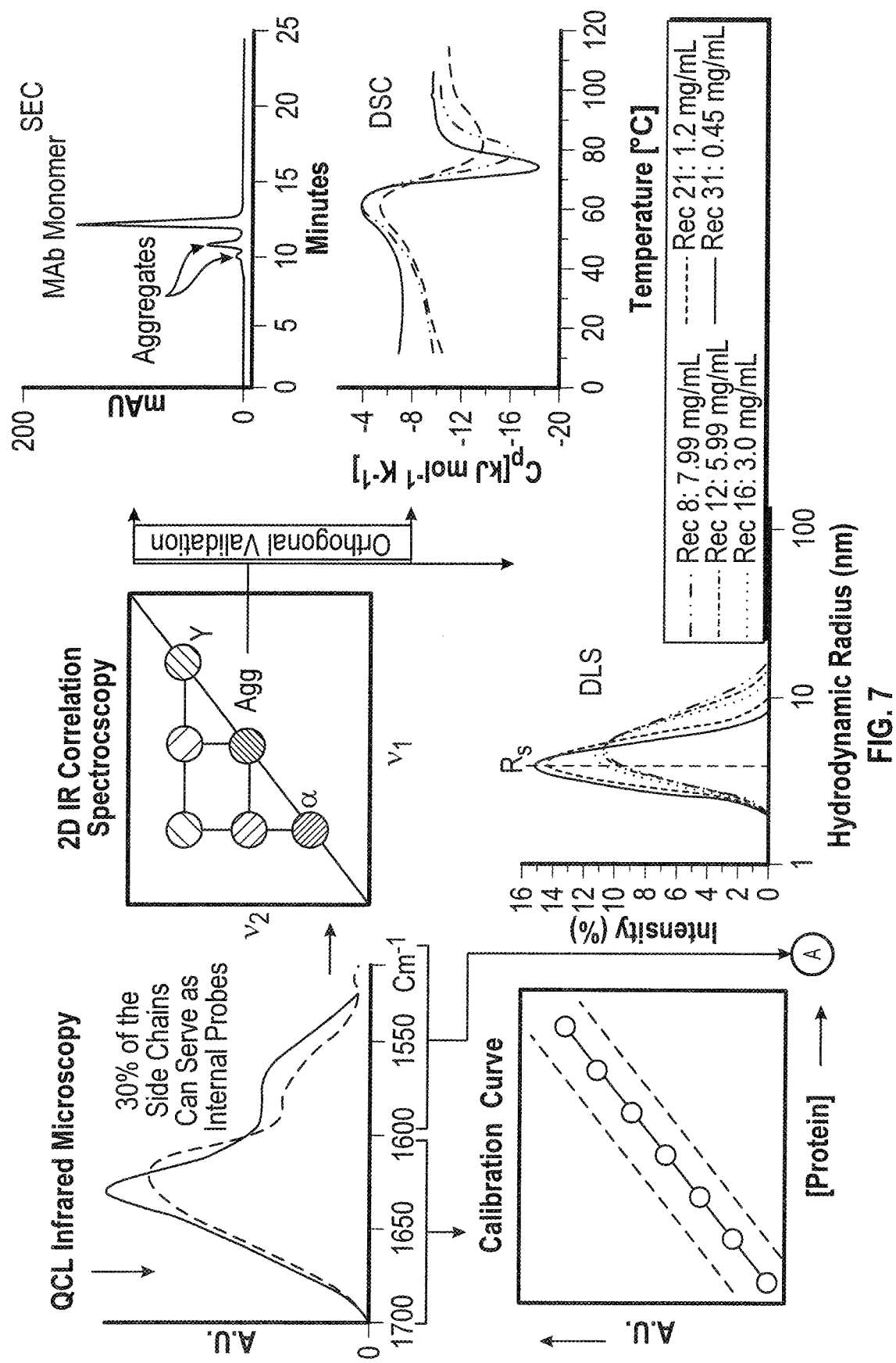
FIG. 7 shows results of a multi-stage analysis.

According to some embodiments, for example as shown in FIG. 7, analysis of acquired data can be performed in stages to provide a comprehensive solution that is statistically valid and highly informative with regard to protein aggregation studies. According to some embodiments, the process illustrated in FIG. 7 can represent applications of the process illustrated in FIG. 3. The results of QCL infrared microscopy (upper left of FIG. 7) are shown with initial and final QCL spectra at low temperature, 5° C. (with greater maximum value) and high temperature, 90° C. (with lesser maximum value) for an (hydrogen→deuterium) exchanged full-length IgG (150 KDa) is shown in the spectral region of 1700-1500 $cm^{-1}$. Differences in the amide I' (1700-1600 $cm^{-1}$, mainly due to peptide bond carbonyl stretching modes) and side chain (1600-1500 $cm^{-1}$ defined in Table 1) bands are observed.

TABLE 1

Amino acids as internal probes in $D_2O$

| Position ($cm^{-1}$) | Vibrational mode | Side Chain | Comment |
|---|---|---|---|
| 1517 | ring bend | Y | immediate surrounding |
| 1545 | ν (COO−) | E | pH, salt-bridge, H-bonding, flexibility and deamination |
| 1567 | ν (COO−) | D | pH, salt-bridge, H-bonding, deamination and flexibility found in β-hairpins |
| 1589 | $ν_s$ (C—N) | R | salt-bridge, H-bonding and flexibility |
| 1609 | $ν_a$ (C—N) | R | salt-bridge, H-bonding and flexibility |
| 1595 | ring bend | H | pH, H-bonding |
| 1849 | SH | C | covalent interaction, oxidative damage, long range flexibility |

By subtracting the initial spectrum at low temperature from all subsequent spectra, the spectral changes due to the temperature increase are revealed (revealing the changes in the protein behavior) which are referred to as covariance spectral data, but also commonly referred to as difference spectra. A cross correlation function is then applied to these spectral changes to determine the relationship between the peaks observed. Two plots are generated, the synchronous and asynchronous plots which provide the correlation between the resulting peaks observed due to the perturbation of the protein sample. These plots provide a wealth of molecular information and the sequential order of molecular events which describe the behavior of the protein. A synchronous plot (lower left of FIG. 7) containing auto peaks (peaks on the diagonal) is shown with the aggregation peak. This diagram represents the greatest intensity change in the protein, and two additional auto-peaks with lower intensity changes are observed. The relationship between these peaks is determined based on observation of the cross peaks (off-diagonal peaks), which are either positive or negative and provide the relationship between the different auto peaks observed on the diagonal (i.e., the changes in intensity due to the subtraction of the initial spectrum). In this hypothetical case, the relationship observed results in an aggregation event that involves the helical secondary structure of the protein, which is also validated by the presence of the tyrosine residue found in this helical motif, thus serving as an internal probe for the aggregation process of the protein. Therefore, the tyrosine peak defines the region of the protein that is aggregating. 2DCOS analysis provides valuable detailed molecular information not available before by other orthogonal techniques such as SEC, DSC and DLS. Results obtained from the QCL are highly reproducible and have been tested rigorously using statistics. The QCL infrared spectral region is highly selective and sensitive thus allowing for the simultaneous study of the protein conformational changes as well as 6 of the 20 amino acid side chain vibrational modes (see Table 1).

Example 1

Figures 8A, 8B:
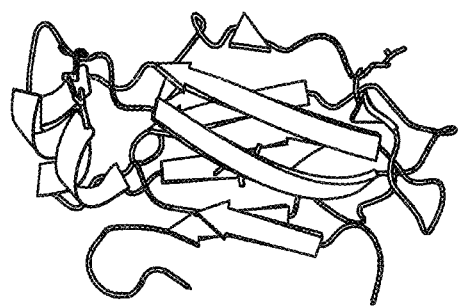
FIG. 8A shows comparison of ADC fragment candidate amino acid sequences for developability assessment. ADC fragment 0 ("ADC0"; SEQ ID NO:1) is the full-length fragment containing an additional 7 amino acids (APELLGG; SEQ ID NO:2) at the N-terminal end. ADC fragment 1 ("ADC1"; SEQ ID NO:3) is truncated at the N-terminal end and like the top fragment contains 1 disulfide bridge. ADC fragment 2 ("ADC2"; SEQ ID NO:4) has two point mutations (L5C/K97C) when compared with ADC fragment 1, thus adding an additional disulfide-bridge to stabilize the ADC fragment 2.
FIG. 8B shows a Richardson ribbon model comprised mainly of β-sheets, β-turns and hinges as well as 2 short helices within the ADC fragment. Shows are the N-terminal end, the C-terminal end, the 3 Arg at positions 25, 62 and 71, the neighboring Pro residues at positions 27 and 61, and the disulfide bond $Cys_{31}$ and $Cys_{91}$. These 3 arginine residues serve as internal probes for ADC's.
Figure 9A:
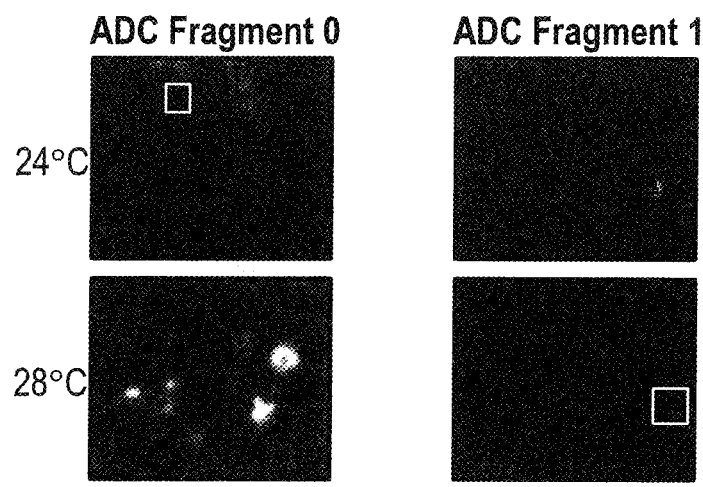
FIGS. 9A and 9B show size and identify of aggregates.
Figure 9B:
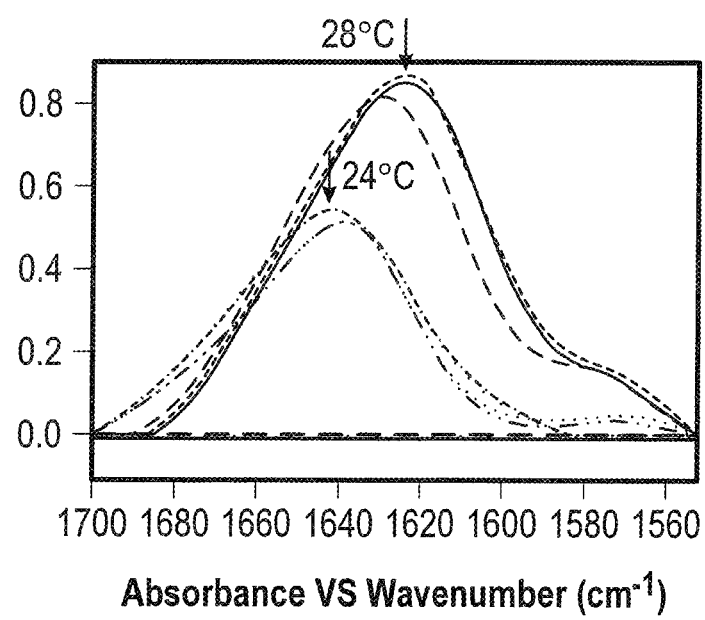
Figure 10:
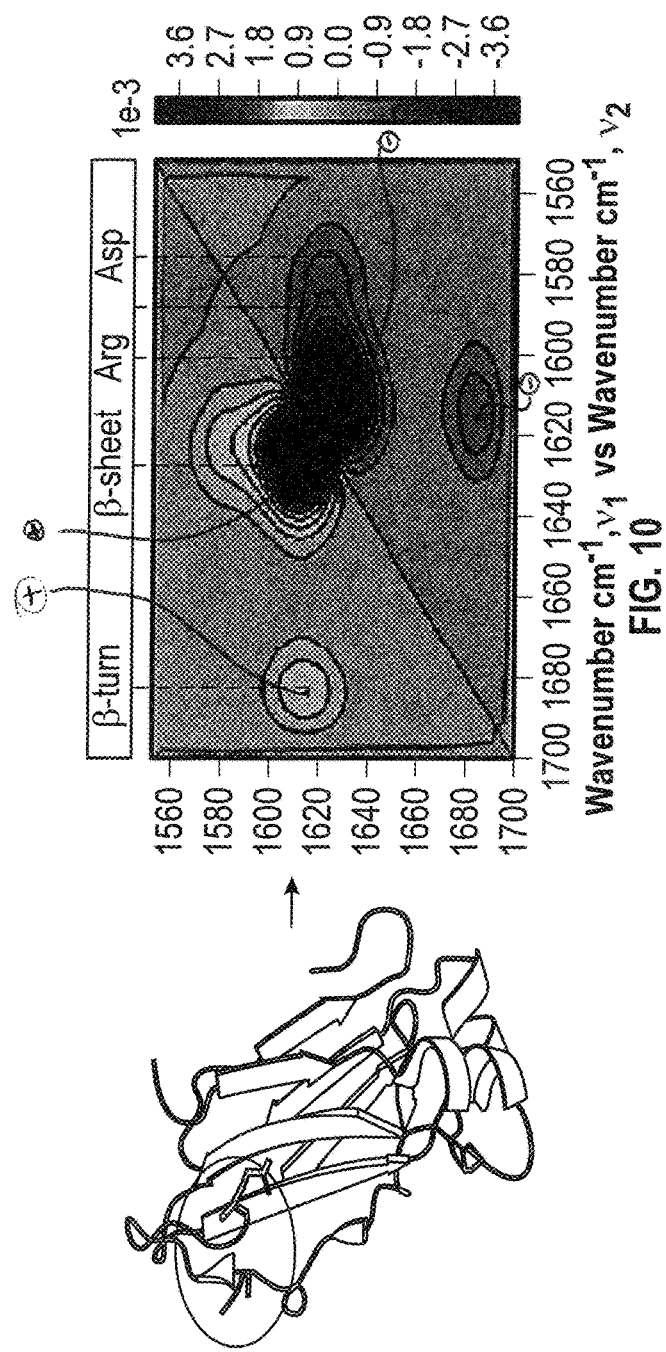
FIG. 10 shows results of a co-distribution analysis. The aggregation mechanism involved the arginine residues and selected anti-parallel β-sheets and β-turn within the protein. Therefore, this analysis provides the region of the protein that is causing the aggregation.

A developability and comparability assessment was performed for three antibody drug conjugate fragments (FIGS. 8A-B). The analysis involved a total of 47 experiments. A QCL microscope was used to perform image acquisition of 43 DOE conditions, 16 of which involved the comparison of 3 ADC fragments termed ADC0, ADC1 & ADC2 in HEPES buffered solution at pH 6.6 and T=24-30° C. It was determined that ADC2 was aggregate free under the conditions studied, whereas ADC1 had some aggregate species, but when heated to 28° C. the aggregate returned to solution (FIG. 9A-B). Moreover, ADC0 candidate had aggregate species present, but upon temperature increase the presence of aggregate species increased. These aggregate species were determined to be ADC0. Similar results were found for ADC1 using 2DCDS analysis (FIG. 10).

Figure 11B:
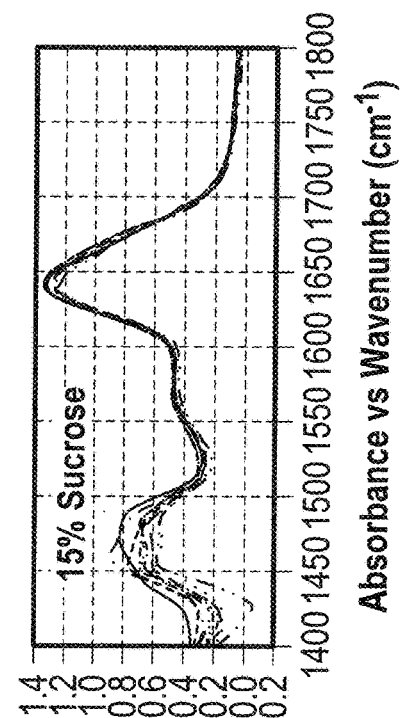
FIG. 11A shows QCL microscope images and FIG. 11B shows associated QCL spectra of ADC fragment 2 in 15% sucrose. This can be used to validate the presence and quantity of both the excipient and the protein candidate.
Figure 11A:
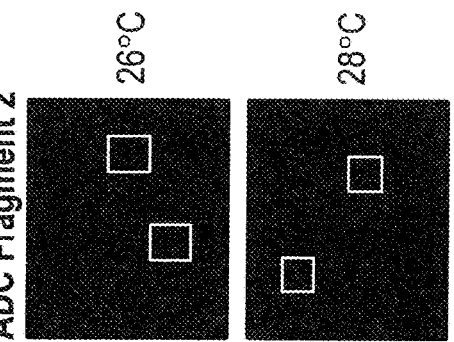
Figure 12A:
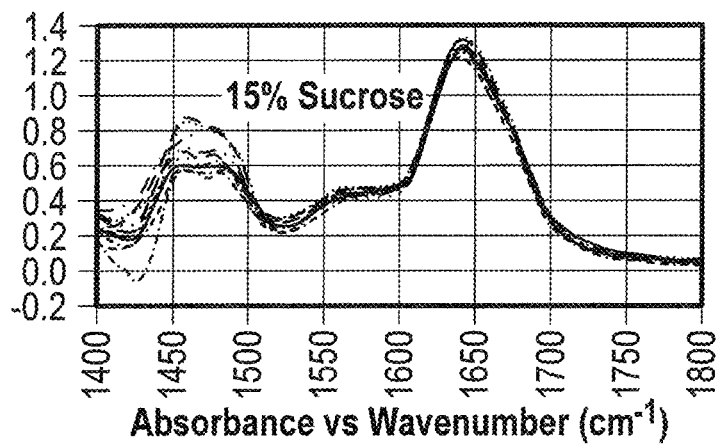
FIGS. 12A, 12B, and 12C show QCL spectral results obtained for ADC2 in HEPES at pH 6.6 in the presence of NaCl and varying amounts of sucrose (FIG. 12A: 15% sucrose, FIG. 12B: 30% sucrose, and FIG. 12C: 60% sucrose) as excipient at 26° C. within the spectral region of 1400-1800 $cm^{-1}$. These results demonstrate the extent to which the quantitative analysis can be performed, providing vital information otherwise difficult to obtain. The stability and conformation of the protein can be confirmed under the desired excipient conditions, while also permitting the determination of concentration of the protein of interest and its excipient in solution. Furthermore, no aggregate species was observed for ADC2 under these conditions.
Figure 12B:
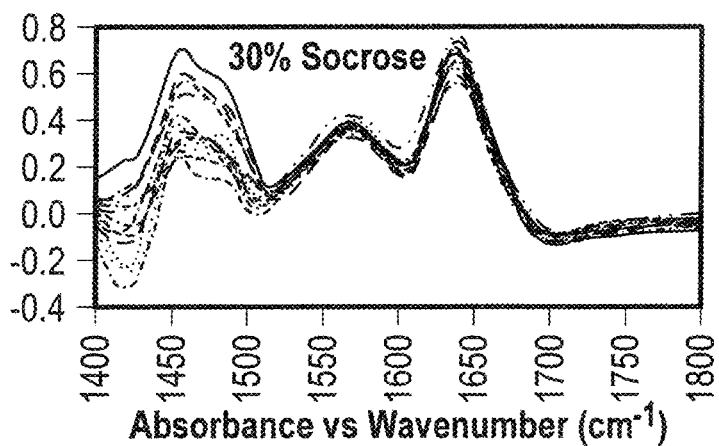
Figure 12C:
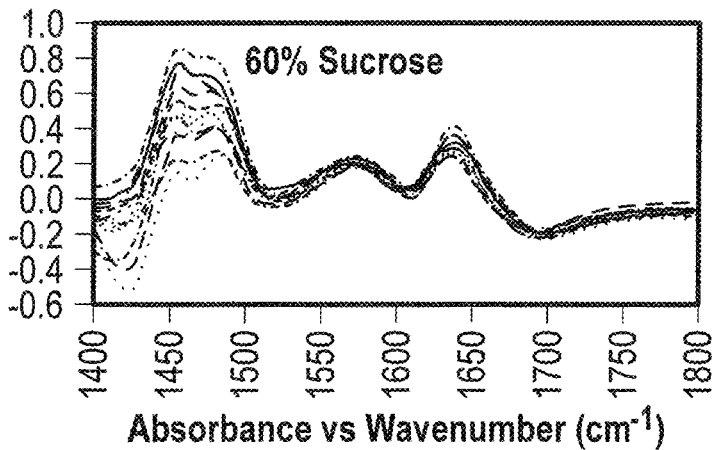

Also, the spectral analysis of aggregate free ADC2 was performed in the presence of varying excipients (sucrose and NaCl) at near-room temperatures, T=24-26° C. (FIGS. 11A-B). The value added of determining reproducibility of the analysis by selecting different regions of interest (ROI) shown as boxed within the QCL images (FIG. 11A) which were analyzed spectroscopically offline (FIG. 11B). The sucrose excipient is shown at 1420-1520 $cm^{-1}$. Also shown are the amide I' and side chain bands (1520-1700 $cm^{-1}$), thus proving the high sensitivity and selectivity of the technique. Further evidence is shown in FIGS. 12A-C. Analytically, the capability of detecting directly both the excipient and the protein therapeutic is of high value to the biopharma industry, because it allows for validation of the presence of the excipient in each formulation. The HT-DCA Platform would provide both the accuracy and reproducibility required for the statistical analysis as well as the highly valued molecular information of the constituents within the sample.

Figure 13:
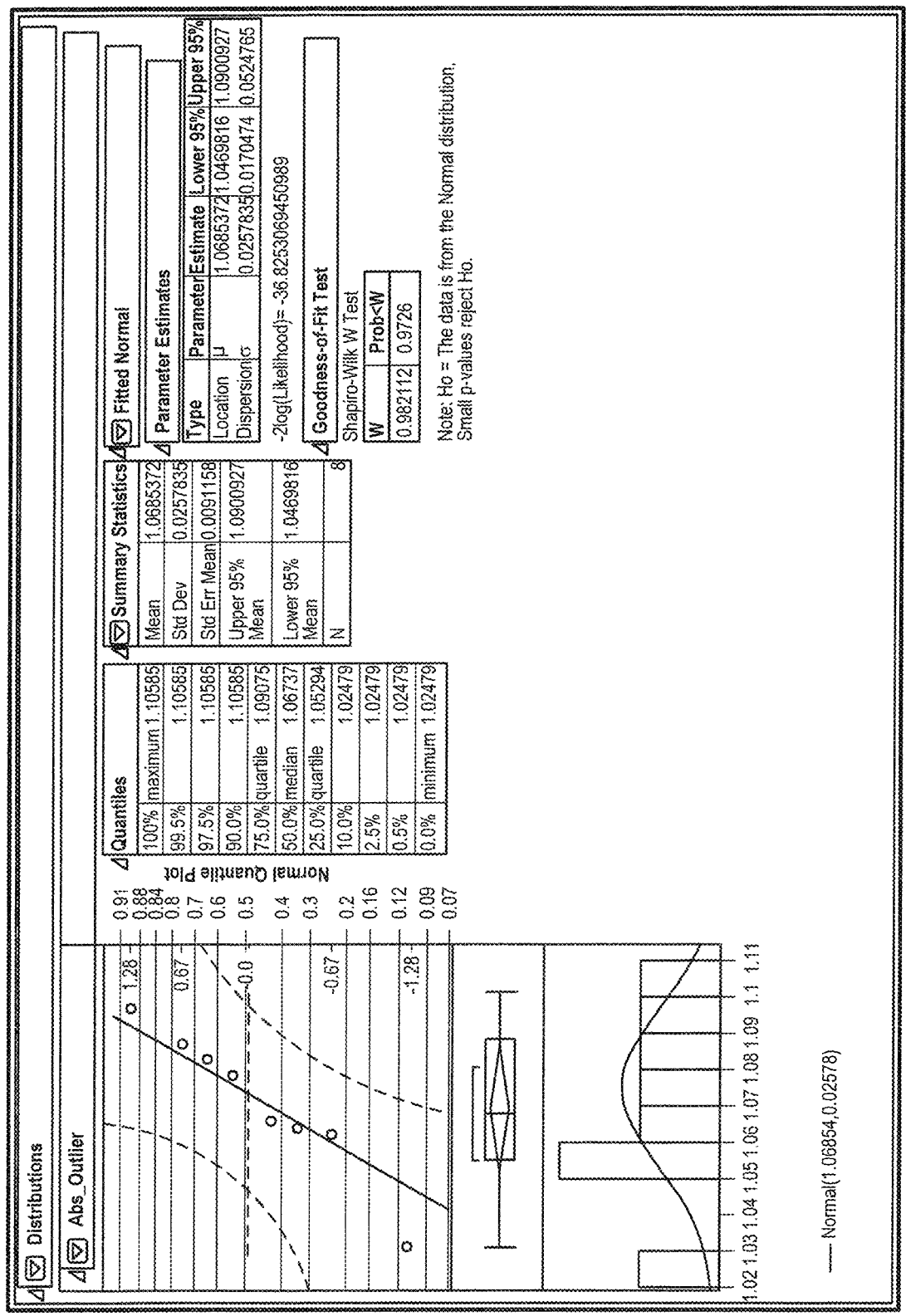
FIG. 13 shows results of normal distribution analysis performed for 43 experiments using the QCL microscope under varying conditions. The QbD experimental setup was such that 324 spectral data were analyzed representing the evaluation of ADC fragment 2 in the presence of varying amounts of NaCl, sucrose and varying ratios of both excipients (i.e., NaCl & sucrose).
Figure 14:
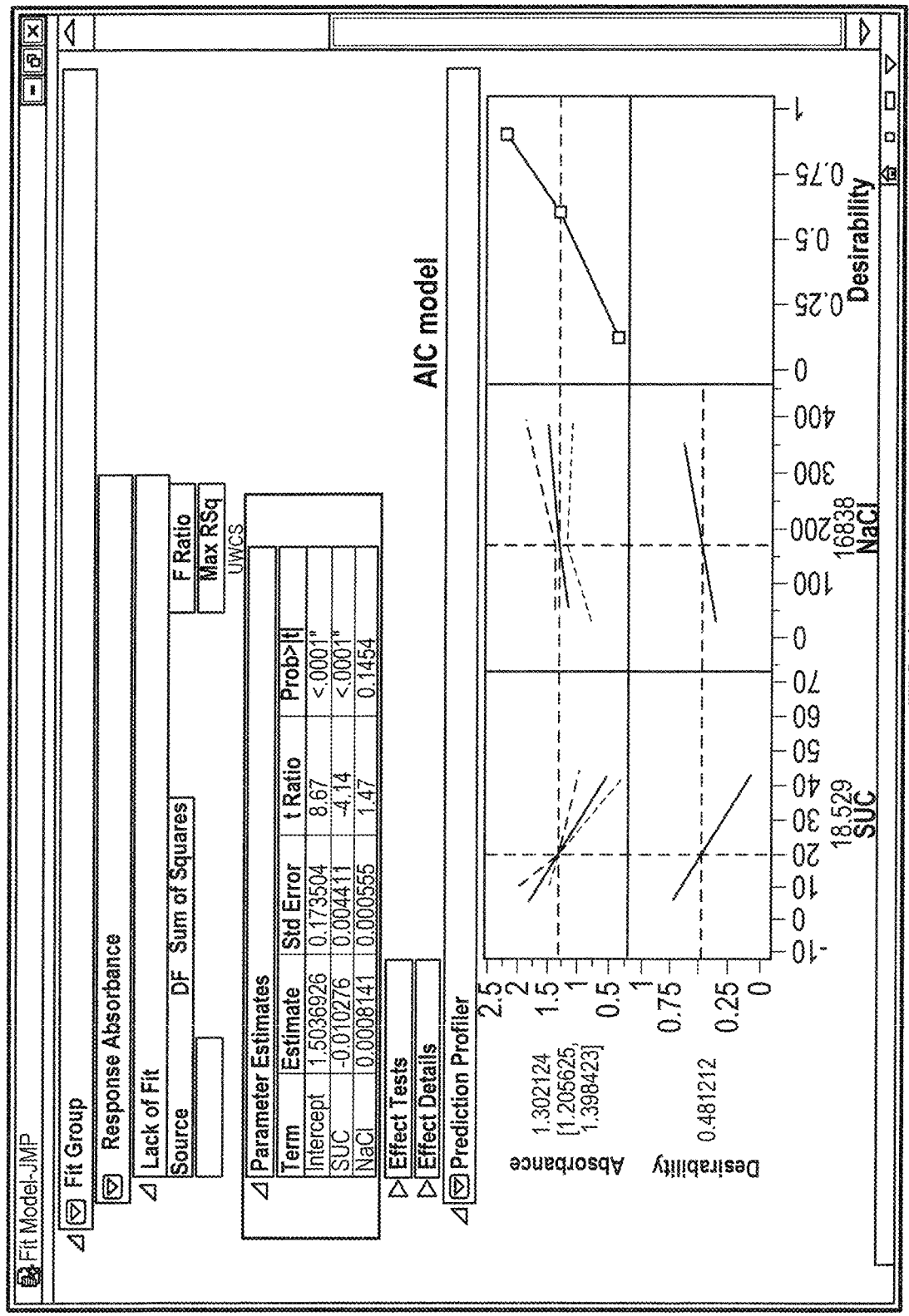
FIG. 14 shows results of DOE stepwise model fitting, including predictive profiles for the ADC2 QCL microscopy spectral data using the second best fit model (AIC model).
Figure 15:
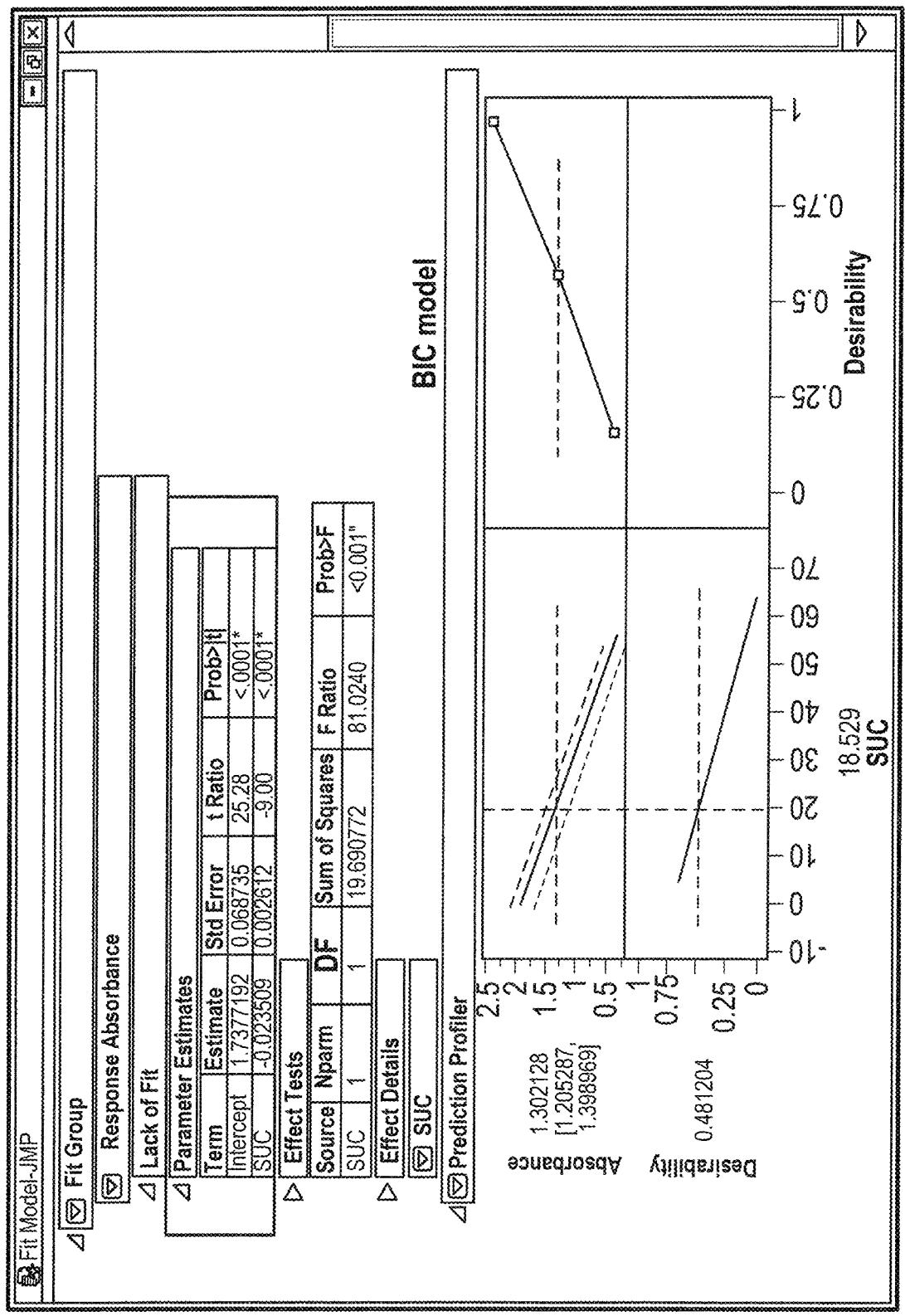
FIG. 15 shows results of DOE stepwise model fitting, including predictive profiles for ADC2 QCL microscopy spectral data using the best fit model (BIC model). The results suggest 18.5% sucrose as the best excipient for ADC2 at near room temperature conditions.

A full factorial design of 516 spectra and Normal Distribution Analysis was performed for 43 experiments using the QCL Microscope (QCL) under varying conditions. The QbD experimental setup was such that 324 spectral data were analyzed representing the evaluation of ADC2 in the presence of varying amounts of NaCl, sucrose and varying ratios of both excipients (i.e., NaCl and sucrose). The sample size was determined to be n=8-12 depending on the standard deviation. Developability and comparability assessment was pursued with ADC2 below are the summary of the results obtained at 15, 30 and 60% Sucrose at 26° and 28° C. Similar results were obtained for varying concentration (325, 350 and 400 mM) of NaCl and varying ratios of sucrose and NaCl as excipients. Typically, the results obtained converged with p values greater than 0.8 (FIG. 13). The distribution analysis was followed by a DOE statistical evaluation using a stepwise all model fit, concluding with the AIC & BIC models (FIG. 14, 15) which reached the same outcome that is 18.5% sucrose as the best excipient for ADC2.

The QCL spectral analysis capabilities of a HT-DCA platform provide further molecular analysis and stability determination of the protein therapeutic. This type of analysis is highly informative, allowing for the optimum design of the protein therapeutic candidate. Two types of correlation analysis were performed: 2DCOS analysis and 2DCDS analysis, providing information regarding the behavior of the protein therapeutic in solution.

Conceptual analysis of the 2D IR correlational plots was applied to infrared spectra of proteins. The amide I' and side chain bands are broad and comprised of many underlying contributions, whether they are conformationally sensitive as are the carbonyl stretches within the peptide bonds or side chain vibrational modes which are informative of their neighboring environment and weak interactions. To extract this information, covariance spectra are generated by subtracting the reference spectrum from all subsequent spectra. For example, in a protein thermal denaturation study (temperature perturbation), the initial spectrum at low temperature would be used for subtraction. The covariance spectra generated include the changes in intensity due to the temperature increase. A correlation function is then applied to the data set which will relate the changes in intensity observed in the covariance spectra in the form of 2 separate graphs with increased resolution. These plots are capable of resolving highly overlapped bands, establishing the most flexible regions of a protein, deciphering the aggregation mechanism in a protein and establishing protein-target interactions. 2D IR correlational plots are termed synchronous and asynchronous plots. These plots are symmetrical in nature and for interpretation purposes, reference is made to the top half of each plot. The synchronous plot has positive peaks on the diagonal known as the auto-peaks. Auto-peaks contain the overall changes in intensity observed for the entire spectral data set. The magnitude of the change can be identified and used to determine the flexibility or susceptibility a region of the protein may have due to the perturbation. The position and number of these peaks is used to determine the underlying spectral contributions for the amide I' and side chain bands (see Table 2).

TABLE 2

Summary of the band assignments for ADC2 in HEPES buffer solution with 15% sucrose

| line | distance (cm) | Wavenumber ($cm^{-1}$) | Band Assignment | number of residues |
|---|---|---|---|---|
| protein backbone | | | | |
| a' | 1.0 | 1682.6 | β-turn | |
| a | 1.3 | 1670.3 | β-turn (hinge loop) | |
| b | 2.1 | 1652.8 | random coil | |
| c | 2.5 | 1632.0 | β-sheet (antiparallel) | |
| d | 2.8 | 1626.4 | β-strand | |
| side chains | | | | |
| e | 3.7 | 1609.7 | Arg ($v_{as}$ ($CN_3H_5^+$)) | 3 |
| f | 4.3 | 1590.1 | His (C=C) | 9 |
| g | 4.9 | 1580.4 | Arg ($v_s$ ($CN_3H_5^+$)) | 3 |
| h | 6.0 | 1553.6 | Asp$^-$ ($v_{as}$ ($COO^-$)) | 10 |
| i | 6.4 | 1543.8 | Glu$^-$ ($v_{as}$ ($COO^-$)) | 8 |
| j | 7.0 | 1529.2 | COO (C-term) | 1 |
| k | 7.5 | 1517.0 | Tyr (C=C) | 5 |

The synchronous plot, also has off diagonal peaks known as the cross peaks. These cross peaks determine the relationship of the auto-peaks. The cross peaks observed in the synchronous plot are due to changes in intensity that are in-phase with one another. One can consider 2 peaks whose intensity changed incrementally or vice versa, these two auto-peaks would have an accompanying cross peak that represents their mutual relationship (FIGS. 16A-B).

The asynchronous plot does not contain peaks on the diagonal, yet renders enhanced spectral resolution. The resulting cross peaks are due to peaks whose intensity in the covariance spectra changed out-of-phase from one another and consequently provides detailed information. Among them, are the sequential order of molecular events due to the thermal perturbation. The cross peaks in the asynchronous plot are either positive or negative and one can determine the sequential order. In general, if the sign of the cross peaks are positive in both plots, the order defined in the asynchronous plot is retained. Therefore, a positive cross peak means $v_1$ occurs prior to $v_2$. This interpretation is designated as true if and only if the same cross peak in the synchronous plot is also positive. However, when the sign of the cross peaks are different in both plots, then the order is reversed.

Figure 16A:
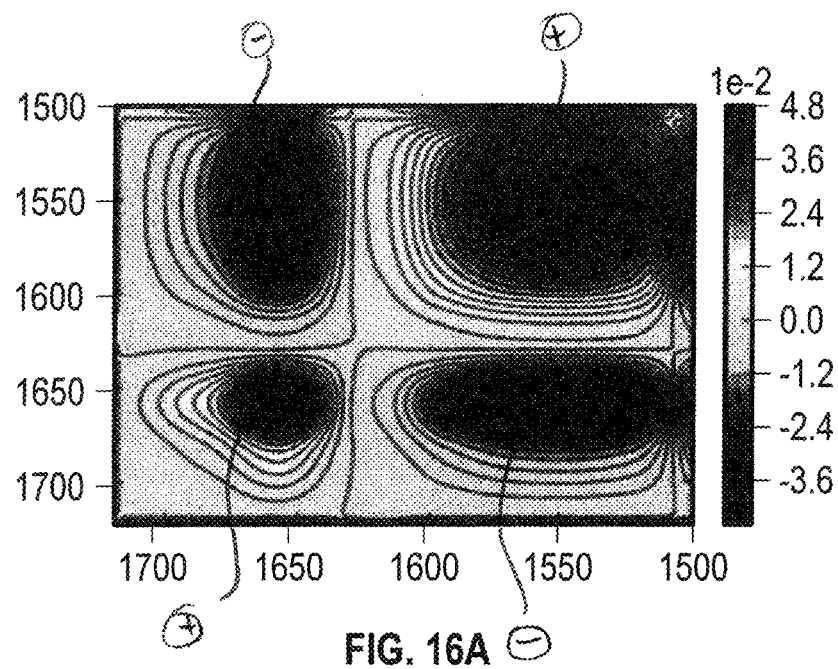
FIGS. 16A and 16B show 2D IR correlation analysis plots (FIG. 16A: synchronous, FIG. 16B: asynchronous) for ADC fragment 2 in the presence of HEPES and 15% sucrose within a temperature range of 26-28° C. The amide I' and side chain bands studied in the spectral region of 1720-1500 $cm^{-1}$. The synchronous plot (FIG. 16A) ADC2 was observed to have mainly β-sheet and β-turn secondary structure with no presence of aggregate species.
Figure 16B:
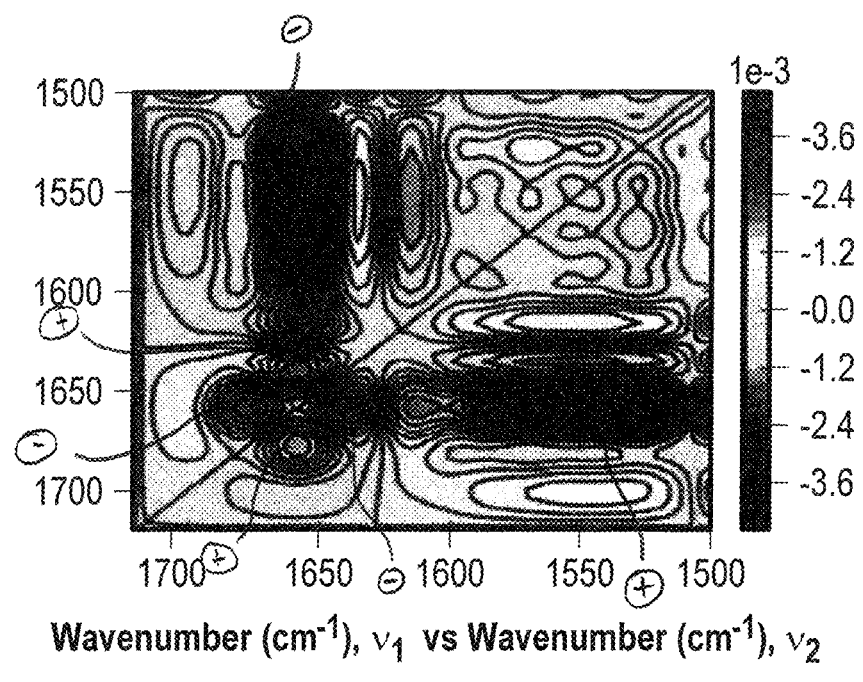
Figure 17:
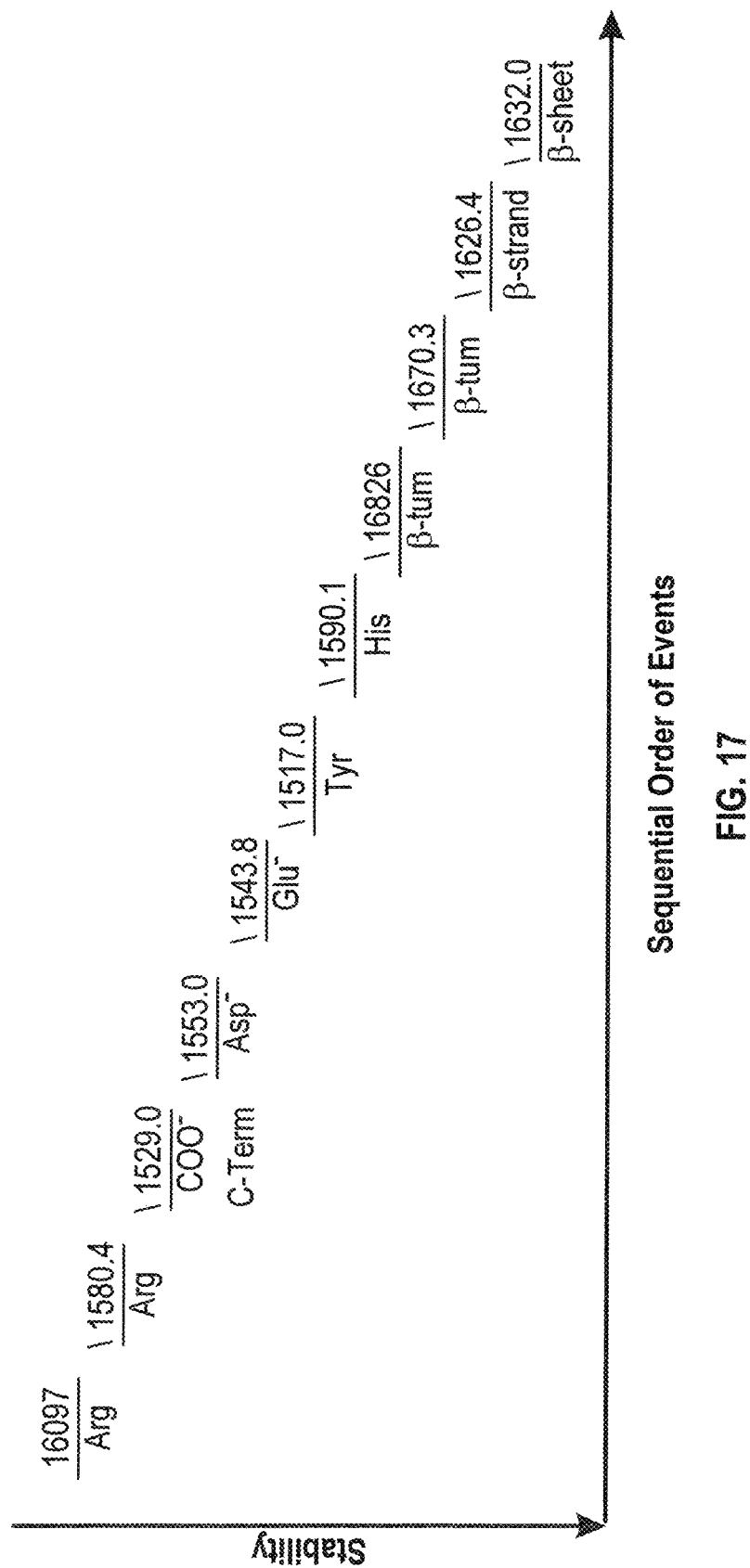
FIG. 17 shows the sequential order of events for ADC fragment 2 in 50 mM HEPES, 150 mM NaCl, 3 mM KCl and 15% sucrose at pH 6.6 and a temperature of 26° C. used to confirm the role of sucrose in stabilizing the protein.

Applying this to the plots of FIGS. 16A-B, a cross peak in the asynchronous plot is found to be positive at (1652, 1632). The 1652 $cm^{-1}$ ($v_1$) peak is perturbed prior to 1632 $cm^{-1}$ ($v_2$). The molecular interpretation would be that the π-helix is perturbed prior to the anti-parallel β-sheets within the protein (Table 2). Similarly, the β-turns (hinge loops, 1670.3 $cm^{-1}$) are perturbed prior to the anti-parallel β-sheets. Furthermore, these plots were used to determine how the sucrose stabilized ADC2 in solution. Hydrogen bonding between side chains and the sucrose stabilized the β-turns (hinge loops) and thus also stabilized the β-sheets. More importantly, the molecular changes that occurred in the protein fragment of interest are shown in FIG. 17.

Although the temperature perturbation was limited to near room temperature, the analysis still allowed for the determination of the H-bonding interaction between the side chains and its aqueous environment and the excipient (sucrose). Also, these interactions stabilized the secondary structure of ADC2.

Figure 18A:
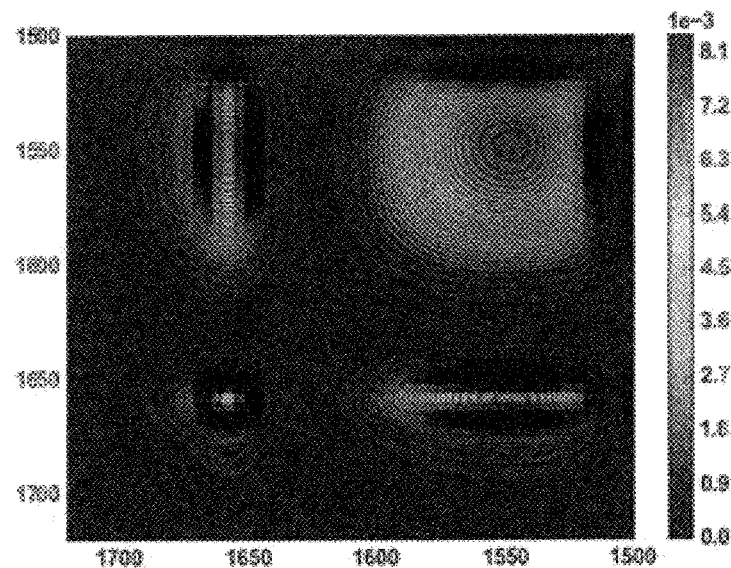
FIGS. 18A and 18B show 2D IR co-distribution analysis plots (FIG. 18A: synchronous, FIG. 18B: asynchronous) ADC2 in HEPES and 15% sucrose as excipient in the temperature range of 26-28° C. Side chains along with the π-helix and β-turns (hinge loops) were perturbed at low temperatures.
Figure 18B:
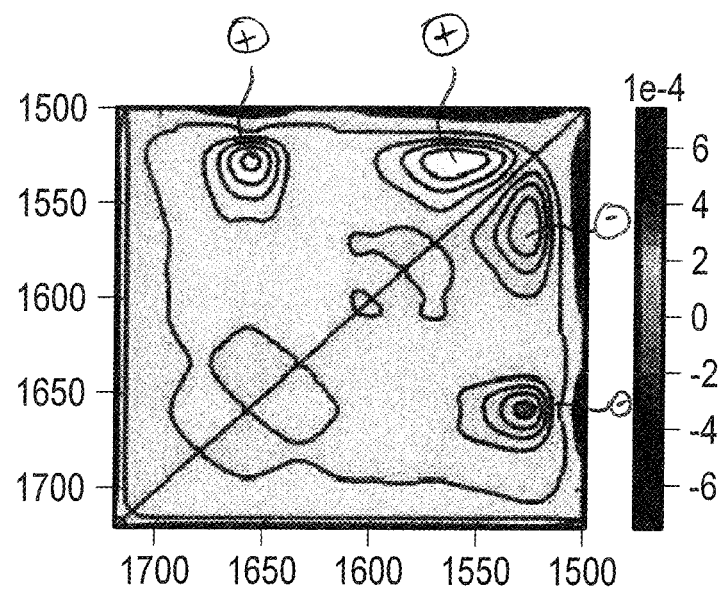

The 2DCDS analysis was found to be useful for the evaluation of the dynamics of a protein solution and the distribution of conformational dynamics within a temperature range, in the current case the temperature range was small only 26-28° C. for ADC2 in HEPES buffers and in the presence of 15% sucrose (FIGS. 18A-B). The interpretation of the asynchronous co-distribution plot is straight forward when compared to the 2D IR correlation. No comparison of cross peak signs between the plots is required. For a positive cross peak, it can be determined that $v_1$ occurs prior to $v_2$. Moreover, for the negative cross peak, it can be determined that $v_2$ occurs prior to $v_1$.

No aggregation was observed for this protein. With reference to the asynchronous plot (FIG. 18B) an inter-dependence is observed between the β-turns also referred to as hinge loops (1660 cm$^{-1}$) and the negatively charged aspartate (1553 cm$^{-1}$), and glutamate (1543 cm$^{-1}$) residues for this protein in solution. This result is consistent with their location within the β-turns motifs of ADC2. 2DCOS analysis and 2DCDS analysis allowed for the complete description of ADC2 and the stabilizing effect of sucrose on ADC2 at the molecular level (FIGS. 16A-18B). In summary, the main stabilizing feature in ADC2 was that of the hinge loops by the salt-bridge interactions observed between the arginines and the nearby aspartate residues. The disruption of salt-bridge interactions were prevented by the second disulfide bridge introduced by site directed mutagenesis. Further stabilization was achieved by formulation conditions which included sucrose as excipient. Specifically, 15% sucrose also provided stabilization by H-bonding with these same residues.

TABLE 3

Summary of the curve-fit results stating the secondary structure composition of ADC fragment 2 at 26° C.

| spectrum # | position (cm$^{-1}$) | Area | Contributing Sub-bands assignment | Secondary Structure Composition (%) | Comments |
|---|---|---|---|---|---|
| 12 | 1688.2 | 4.1 | β-turn | | sum of β-turns |
| | 1670.6 | 12.5 | β-turn (hinge loop) | 29 | total area was 57.3 |
| | 1639.4 | 18.8 | β-sheet (anti) | 32.8 | essentially |
| | 1623.7 | 9.9 | β-strand | 17.3 | β-structure |
| | 1655.2 | 11.9 | random coil | 20.7 | 79.10% |
| 13 | 1691.1 | 3.27 | β-turn | | sum of β-turns |
| | 1670.2 | 13.2 | β-turn (hinge loop) | 29.4 | total area was 58.1 |
| | 1639.4 | 19.3 | β-sheet (anti) | 33.2 | essentially |
| | 1624.0 | 10.2 | β-strand | 17.5 | β-structure |
| | 1655.2 | 11.54 | random coil | 19.8 | 80.10% |
| 14 | 1692.2 | 1.86 | β-turn | | sum of β-turns |
| | 1672.2 | 16.0 | β-turn (hinge loop) | 29.3 | total area was 60.8 |
| | 1639.9 | 21.9 | β-sheet (anti) | 35.9 | essentially |
| | 1625.1 | 10.4 | β-strand | 17.0 | β-structure |
| | 1656.1 | 10.7 | random coil | 17.6 | 82.0% |

Figure 19:
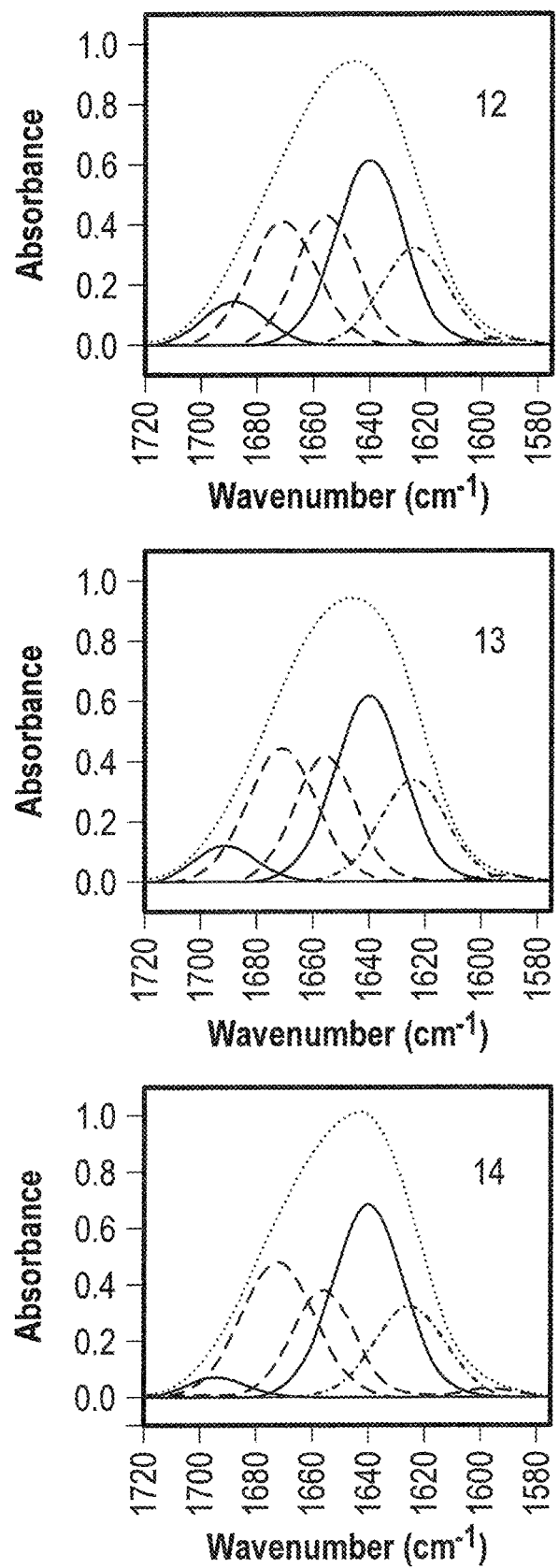
FIG. 19 shows representative curve-fit analysis for ADC Fragment 2 in $D_2O$ using the band assignments generated from the 2D IR correlation analysis and for which 80.4+/−1.1% of the protein was determined to comprise β-structure (see also Tables 2 and 3).

FIG. 19 shows plots corresponding to the results shown in Table 3.

Example 2

Samples including the National Institute of Standards & Technology Reference Material 8671 (RM8671) Lot No. 14HB-D-002, a humanized IgG1κ monoclonal antibody (NIST mAb), in H$_2$O were studied for analysis according to methods described herein. Samples were added to cells of a CaF$_2$ slide for data acquisition using a QCL microscope. The applied perturbation was temperature within the range of 24-60° C. with 4° C. temperature intervals. QCL IR spectral data was acquired using a 4× magnification objective at 4 cm$^{-1}$ with data encoded every 0.5 cm$^{-1}$ and baseline corrected.

The NIST mAb standard is an IgG1κ protein. The amino acid sequences of the heavy chain (SEQ ID NO:5) and the light chain (SEQ ID NO:6) of the antibody are presented below.

```
RM 8671 Heavy Chain AA
QVTLRESGPALVKPTQTLTLTCTFSGFSLSTAGMSVGWIRQPPGKALEW

LADIWWDDKKHYNPSLKDRLTISKDTSKNQVVLKVTNMDPADTATYYCA

RDMIFNFYFDVWGQGTTVTVSS ASTKGPSVFPLAPSSKSTSGGTAALG

CLVKDYFPEPVTVSWNSGALTSGVHTFPAVLQSSGLYSLSSVVTVPSSS

LGTQTYICNVNHKPSNTKVDKRV EPKSCDKTHTCPPCP APELLGGPS

VFLFPPKPKDTLMISRTPEVTCVVVDVSHEDPEVKFNWYVDGVEVHNAK

TKPREEQYNSTYRVVSVLTVLHQDWLNGKEYKCKVSNKALPAPIEKTIS

KAKGQPREPQVYTLPPSREEMTKNQVSLTCLVKGFYPSDIAVEWESNGQ

PENNYKTTPPVLDSDGSFELYSKLTVDKSRWQQGNVFSCSVMHEALHNH

YTQKSLSLSPGK

RM 8671 Light Chain
DIQMTQSPSTLSASVGDRVTITCSASSRVGYMHWYQQKPGKAPKLLIYD

KLASGVPSRFSGSGSGTEFTLTISSLQPDDFATYYCFQGSGYPFTTSFG

GGTKVEIK RTVAAPSVFIFPPSDEQLKSGTASVVCLLNNFYPREAKVQ

WKVDNALQSGNSQESVTEQDSKDSTYSLSSTLTLSKADYEKHKVYACEV

THQGLSSPVTKSFNRGEC
```

Assignment of amino acid side chains for the sample is provided in Tables 4 and 5.

TABLE 4

Assignment of heavy amino acid side chains for NIST mAb in H$_2$O

| item | side chain Heavy Chain | code | vibrational mode | position (cm$^{-1}$) | number of residues in sequence |
|---|---|---|---|---|---|
| 1 | Tyr | Y | ν (C=C) | 1518 | 32 |
| 2 | Glu$^-$ | E | ν (COO-) | 1543-1560 | 40 |
| 3 | Asp$^-$ | D | ν (COO-) | 1570-1574 | 42 |
| 4 | His | H | ν (C=C) | 1596 | 20 |
| 5 | C-term end | | ν (COO-) | 1598 | 2 |
| 6 | Arg | R | $v_{as}$ (CN$_3$H$_5^+$) | 1673 | 22 |
| 7 | Arg | R | $v_s$ (CN$_3$H$_5^+$) | 1633 | 22 |
| 8 | Lys | K | $δ_{as}$ (NH$_3^+$) | 1629 | 70 |
| 9 | Lys | K | $δ_s$ (NH$_3^+$) | 1526 | 70 |
| 10 | Asn | N | ν (C=O) | 1678 | 36 |
| 11 | Gln | Q | ν (C=O) | 1670 | 32 |

TABLE 5

Assignment of light amino acid side chains for NIST mAb in H$_2$O

| item | side chain light Chain | code | vibrational mode | position (cm$^{-1}$) | number of residues in sequence |
|---|---|---|---|---|---|
| 1 | Tyr | Y | ν (C=C) | 1518 | 20 |
| 2 | Glu$^-$ | E | ν (COO-) | 1543-1560 | 18 |
| 3 | Asp$^-$ | D | ν (COO-) | 1570-1574 | 20 |
| 4 | His | H | ν (C=C) | 1596 | 6 |
| 5 | C-term end | | ν (COO-) | 1598 | 2 |
| 6 | Arg | R | $v_{as}$ (CN$_3$H$_5^+$) | 1673 | 12 |

TABLE 5-continued

Assignment of light amino acid side chains for NIST mAb in H₂O

| item | side chain light Chain | code | vibrational mode | position (cm⁻¹) | number of residues in sequence |
|---|---|---|---|---|---|
| 7 | Arg | R | $v_s$ (CN₃H₅⁺) | 1633 | 22 |
| 8 | Lys | K | $\delta_{as}$ (NH₃⁺) | 1629 | 28 |
| 9 | Lys | K | $\delta_s$ (NH₃⁺) | 1526 | 28 |
| 10 | Asn | N | v (C=O) | 1678 | 10 |
| 11 | Gln | Q | v (C=O) | 1670 | 24 |

As shown in FIG. 20A, QCL spectra of NIST mAb at 50 mg/mL in the MID IR spectral region of 1750-1400 cm⁻¹ was acquired within the temperature range of 24-60° C. in H₂O. FIG. 20A shows overlaid spectra showing the amide I, II and III bands. Based on the spectral data synchronous (FIG. 20B) and asynchronous (FIG. 20C) 2D IR correlation analysis plots were generated. Overlapping H₂O absorbance was observed in the amide I band not so in the amide II and III bands, suggesting sufficient protein concentration was achieved for analysis. The method applied, according to embodiments of the present disclosure, eliminates the need for the subjective manipulation of H₂O or reference subtraction by the user.

Figures 21A, 21B, 21C:
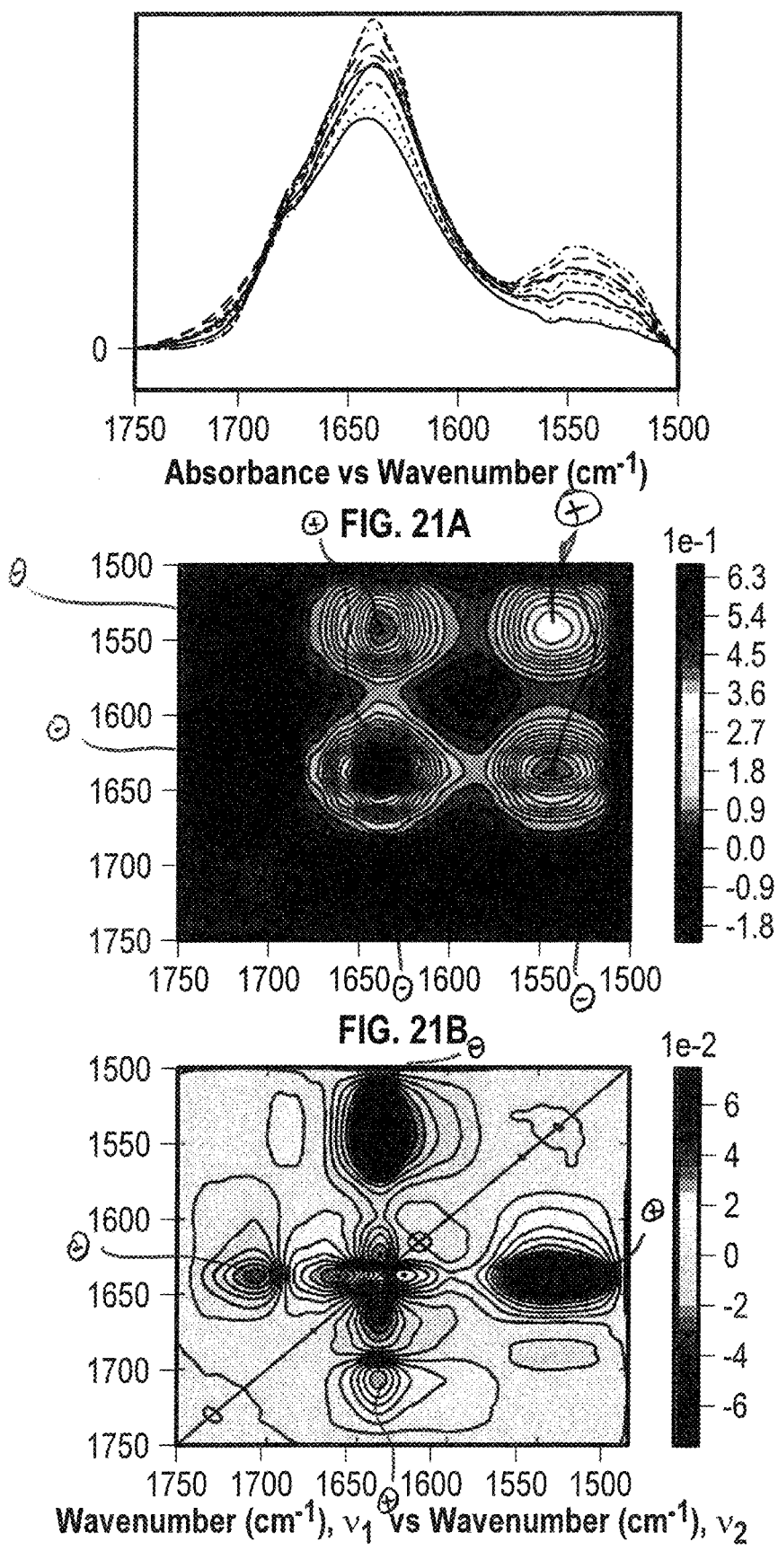
FIG. 21A shows overlaid spectra showing both the amide I and II bands for NIST mAb at 50 mg/mL in the MID IR spectral region of 1750-1500 $cm^{-1}$ acquired within the temperature range of 24-60° C. in $H_2O$.
FIGS. 21B and 21C show 2D IR correlation analysis plots (FIG. 21B: synchronous, FIG. 21C: asynchronous) for the sample of FIG. 21A.

As shown in FIG. 21A, QCL spectra of NIST mAb at 50 mg/mL in the MID IR spectral region of 1750-1500 cm⁻¹ was acquired within the temperature range of 24-60° C. in H₂O. FIG. 21A shows overlaid spectra showing both the amide II and III bands. Based on the spectral data synchronous (FIG. 21B) and asynchronous (FIG. 21C) plots. The correlation between the amide I and II bands is established. Enhanced resolution is achieved through the use of the asynchronous plot.

Peak assignments of NIST mAb at 50 mg/mL in H₂O are provided in Table 6.

TABLE 6

Summary of peak assignments of NIST mAb at 50 mg/mL in H₂O

| Peak Assignment | Peak Position (cm⁻¹) |
|---|---|
| β-turn | 1692 |
| β-turn | 1681.6 |
| Arg | 1668 |
| Hinge Loop | 1660 |
| α-helix | 1652 |
| β-sheet | 1635 |
| Agg | 1618 |
| His | 1602 |
| Asp⁻ | 1573 |
| Glu⁻ | 1542 |
| Try | 1515.8 |

Note:
Aggregation (Agg)

Figure 22:
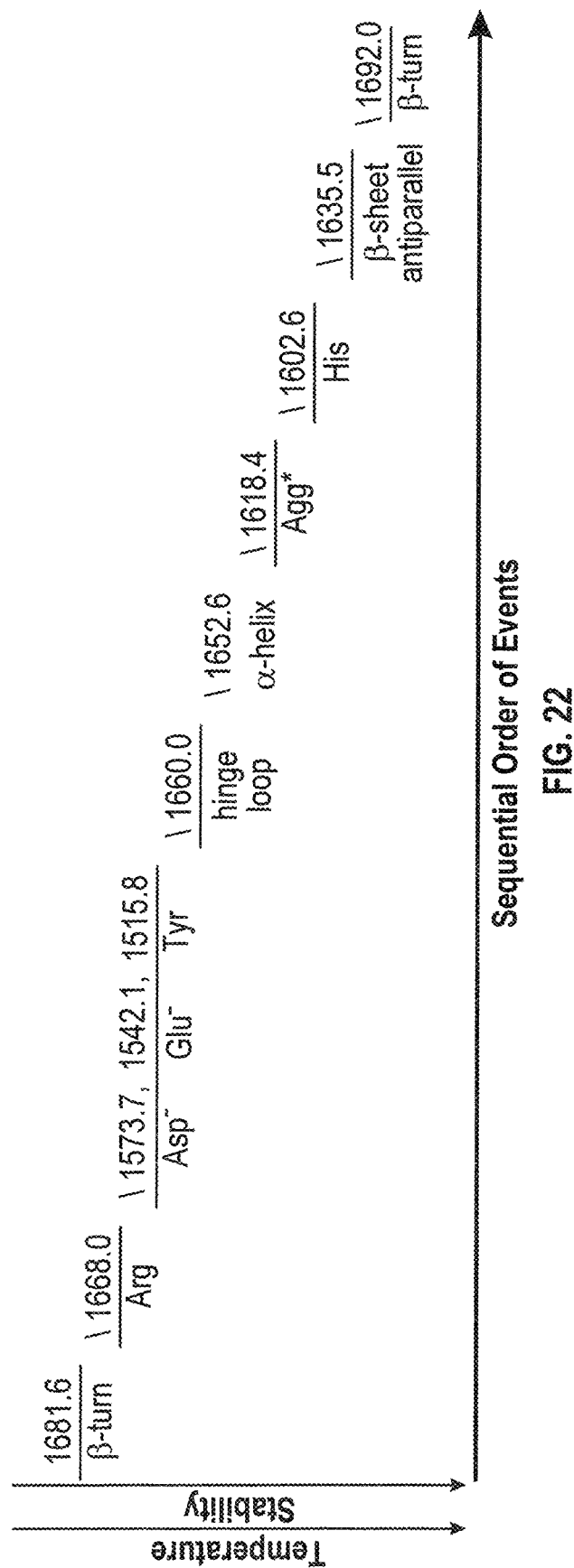
FIG. 22 shows the sequential order of events for NIST mAb at 50 mg/mL in $H_2O$ under thermal stress within the temperature range of 24-60° C.

The sequential order of events for NIST mAb at 50 mg/mL in H₂O under thermal stress within the temperature range of 24-60° C. is shown in FIG. 22. The 1635.5 cm⁻¹ is assigned antiparallel β-sheet due to the perturbation of the 1692 cm⁻¹ β-turn, both vibrational modes are the most stable. Also, 1618 cm⁻¹ has been assigned to protein Aggregation which was thermally induced at 60° C. based on this work. 1652 cm⁻¹ may be assigned to α-helix.

The sequential order of events for NIST mAb at 50 mg/mL in H₂O is provided in Table 7.

TABLE 7

Summary of sequential order of events for NIST mAb at 50 mg/mL in H₂O

| Event | Asynchronous and Synchronous plot analysis |
|---|---|
| 1 | β-turn (1681.6 cm⁻¹) → Arg (1668 cm⁻¹) |
| 2 | Asp⁻ (1573 cm⁻¹), Glu⁻ (1542 cm⁻¹), Try (1515.8 cm⁻¹) → α-helix (1652 cm⁻¹) |
| 3 | Arg (1668 cm⁻¹) → α-helix (1652 cm⁻¹) |
| 4 | Hinge loop (1660 cm⁻¹) → His (1602 cm⁻¹) |
| 5 | β-turn (1681.6 cm⁻¹) → His (1602 cm⁻¹) |
| 6 | Hinge loop (1660 cm⁻¹) → Agg (1618 cm⁻¹) |
| 7 | α-helix (1652 cm⁻¹) → Agg (1618 cm⁻¹) |
| 8 | Hinge loop (1660 cm⁻¹) → α-helix (1652 cm⁻¹) |
| 9 | His (1602 cm⁻¹) → β-turn (1692 cm⁻¹) |
| 10 | β-sheet (1635 cm⁻¹) → β-turn (1692 cm⁻¹) |

Figure 23:
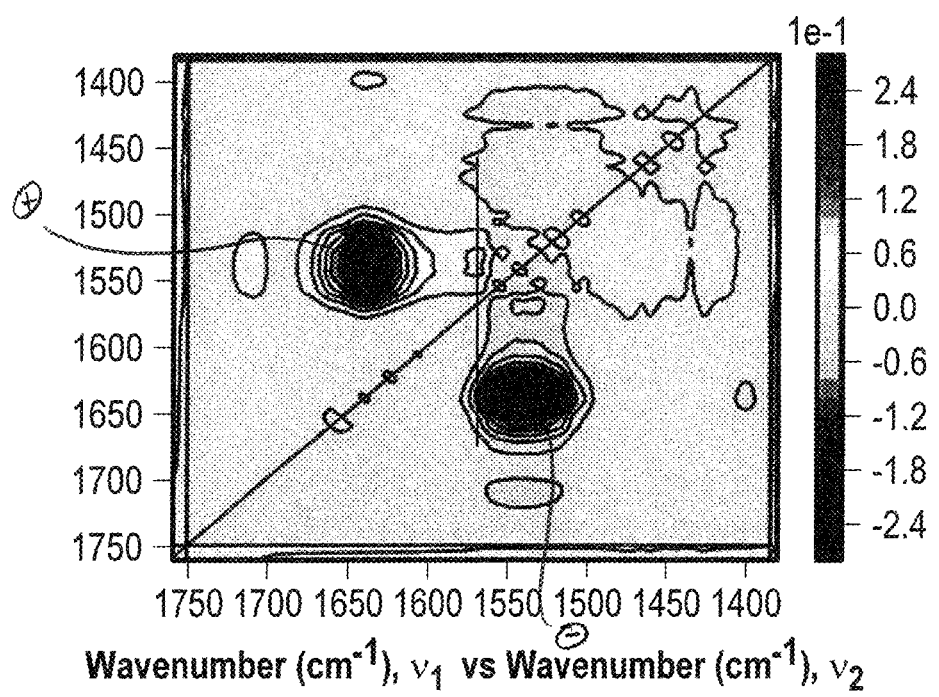
FIG. 23 shows an asynchronous 2D IR co-distribution analysis plot for NIST mAb at 50 mg/mL in $H_2O$ under thermal stress within the temperature range of 24-60° C.

Note:
Aggregation (Agg)
β-sheet and β-turn appear as coupled modes indicating presence of antiparallel β-sheet FIG. 23 shows an asynchronous 2D IR co-distribution analysis plot for NIST mAb at 50 mg/mL in H₂O under thermal stress within the temperature range of 24-60° C. The thermal stress within the NIST mAb (50 mg/mL) in the temperature range of 24-60° C. and spectral region 1760-1380 cm⁻¹. This plot provides the most common response in a population of proteins in solution. Therefore in the case of the NIST mAb at 50 mg/mL, its thermal stress was related to the perturbation of the glutamates along with the Arg presumably through salt-bridge interaction. Glutamates H-bonded to His residues, and these residues are located within the α-helices and β-sheets.

FIGS. 24A-D show an example of automated analysis providing the relationship within the (A) overlaid raw spectral data, 2D IR correlation: (B) synchronous and (C) asynchronous plots, and (D) co-distribution asynchronous plot. Broken vertical lines are provided during automated analysis based on the auto peak (positive peaks on the diagonal shown in FIG. 24B) absolute intensity values within the synchronous plot.

Example 3

Samples including Bovine Serum Albumin ("BSA") in H₂O were studied for analysis according to methods described herein. Samples were added to cells of a CaF₂ slide for data acquisition using a QCL microscope. The applied perturbation was temperature within the range of 24-60° C. with 4° C. temperature intervals. QCL spectral data was acquired using a 4× magnitude objective at 4 cm⁻¹ with data encoded every 0.5 cm⁻¹ and baseline corrected.

Below is an amino acid sequence for the BSA analyzed.

(SEQ ID NO: 7)
DTHKSEIAHRFKDLGEEHFKGLVLIAFSQYLQQCPFDEHVKLVNELTE

FAKTCVADESHAGCEKSLHTLFGDELCKVASLRETYGDMADCCEKQEP

ERNECFLSHKDDSPDLPKLKPDPNTLCDEFKADEKKFWGKYLYEIARR

HPYFYAPELLYYANKYNGVFQECCQAEDKGACLLPKIETMREKVLTSS

ARQRLRCASIQKFGERALKAWSVARLSQKFPKAEFVEVTKLVTDLTKV

HKECCHGDLLECADDRADLAKYICDNQDTISSKLKECCDKPLLEKSHC

IAEVEKDAIPENLPPLTADFAEDKDVCKNYQEAKDAFLGSFLYEYSRR

HPEYAVSVLLRLAKEYEATLEECCAKDDPHACYSTVFDKLKHLVDEPQ

-continued

```
NLIKQNCDQFEKLGEYGFQNALIVRYTRKVPQVSTPTLVEVSRSLGKV

GTRCCTKPESERMPCTEDYLSLILNRLCVLHEKTPVSEKVTKCCTESL

VNRRPCFSALTPDETYVPKAFDEKLFTFHADICTLPDTEKQIKKQTAL

VELLKHKPKATEEQLKTVMENFVAFVDKCCAADDKEACFAVEGPKLVV

STQTALA
```

Assignment of amino acid side chains for the sample is provided in Table 8.

TABLE 8

Assignment of amino acid side chains for BSA in $H_2O$

| item | side chain | code | vibrational mode | position (cm$^{-1}$) | number of residues in sequence |
|---|---|---|---|---|---|
| 1 | Tyr | Y | ν (C═C) | 1518 | 20 |
| 2 | Glu⁻ | E | ν (COO-) | 1543-1560 | 62 |
| 3 | Asp⁻ | D | ν (COO-) | 1570-1574 | 39 |
| 4 | His | H | ν (C═C) | 1596 | 17 |
| 5 | C-term end | | ν (COO-) | 1598 | 1 |
| 6 | Arg | R | $\nu_{as}$ (CN$_3$H$_5^+$) | 1673 | 21 |
| 7 | Arg | R | $\nu_s$ (CN$_3$H$_5^+$) | 1633 | 21 |
| 8 | Lys | K | $\delta_{as}$ (NH$_3^+$) | 1629 | 48 |
| 9 | Lys | K | $\delta_s$ (NH$_3^+$) | 1526 | 48 |
| 10 | Asn | N | ν (C═O) | 1678 | 14 |
| 11 | Gln | Q | ν (C═O) | 1670 | 21 |

Figure 25A:
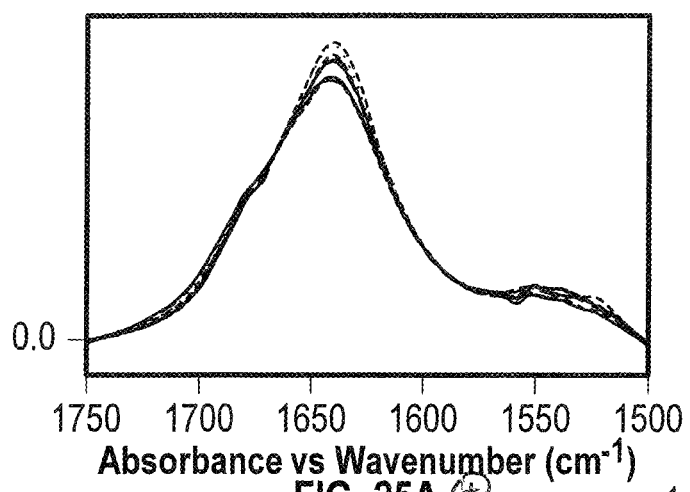
FIG. 25A shows overlaid spectra showing both the amide I and II bands for BSA at 40 mg/mL in the MID IR spectral region of 1750-1500 $cm^{-1}$ acquired within the temperature range of 24-60° C. in $H_2O$.
Figure 25B:
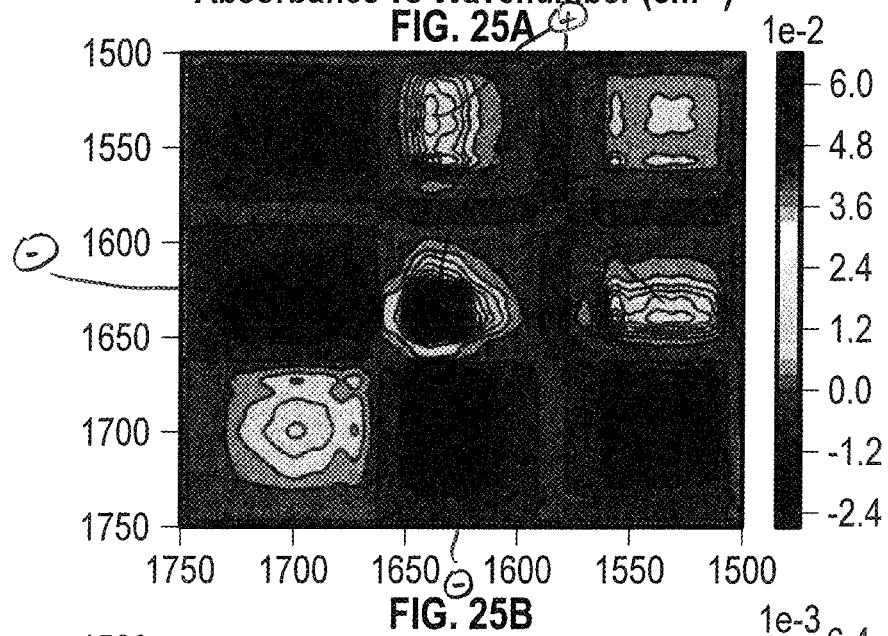
FIGS. 25B and 25C show 2D IR correlation analysis plots (FIG. 25B: synchronous, FIG. 25C: asynchronous) for the sample of FIG. 25A.
Figure 25C:
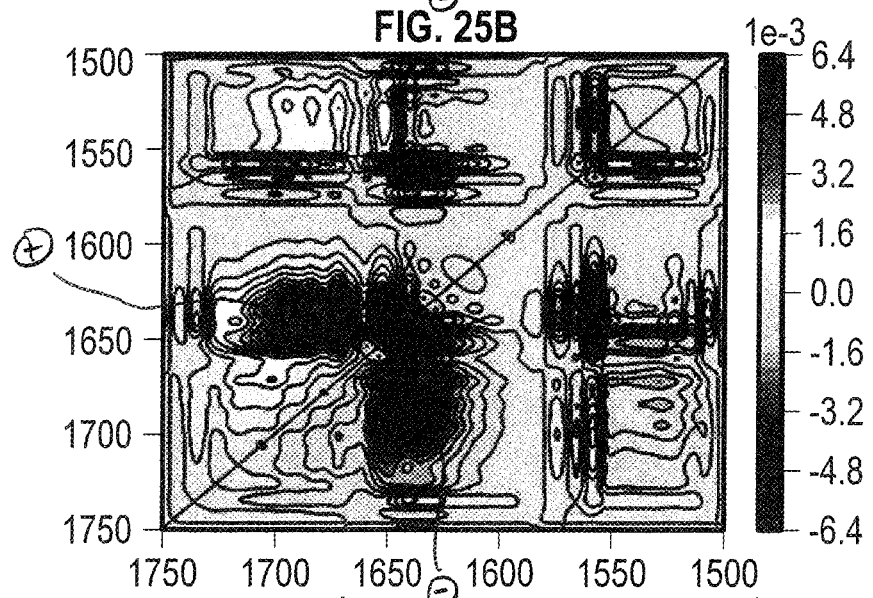

As shown in FIG. 25A, QCL spectra of BSA at 40 mg/mL in the MID IR spectral region of 1750-1500 cm$^{-1}$ was acquired within the temperature range of 24-60° C. in $H_2O$. FIG. 25A shows overlaid spectra showing the amide I and II bands. Based on the spectral data synchronous (FIG. 25B) and asynchronous (FIG. 25C) 2D IR correlation analysis plots were generated. The correlation between the amide I and II bands is established. Enhanced resolution is achieved through the use of the asynchronous plot. Also, the highest intensity auto peak within the synchronous plot is due to helical perturbation for this globular protein. In addition, no aggregation was observed.

Peak assignments of BSA at 40 mg/mL are provided in Table 9.

TABLE 9

Summary of peak assignments of BSA at 40 mg/mL

| Peak Assignment | Peak Position (cm$^{-1}$) |
|---|---|
| β-turn | 1698 |
| β-turn | 1684 |
| Arg | 1672.4 |
| α-helix | 1653.9 |
| β-sheet/Arg | 1629.6 |
| His | 1606.5 |
| Asp⁻ | 1584.5 |
| Asp⁻ | 1576.4 |
| Asp⁻ | 1567.1 |
| Glu⁻ | 1559 |
| Glu⁻ | 1541.7 |
| Lys | 1530 |
| Lys | 1525.5 |
| Tyr | 1518.5 |

Figure 26:
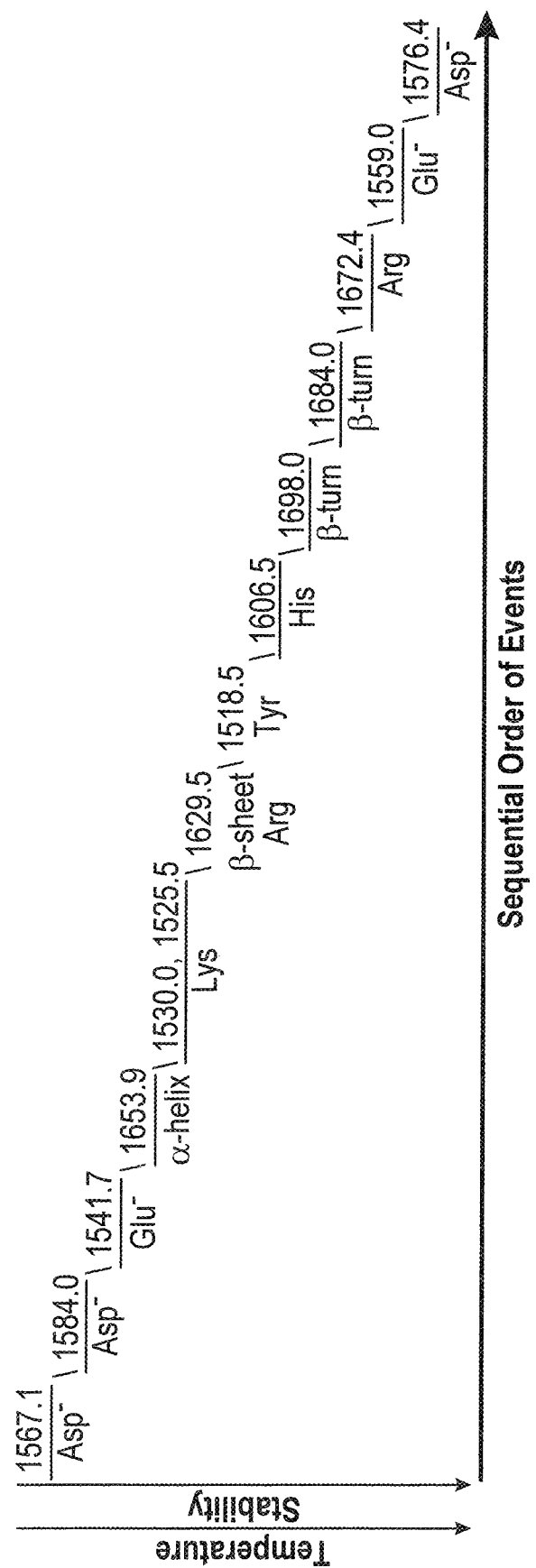
FIG. 26 shows the sequential order of events for BSA 40 mg/mL in $H_2O$ under thermal stress (24-60° C.).

The sequential order of events for BSA at 40 mg/mL under thermal stress within the temperature range of 24-60° C. is shown in FIG. 26. The sequential order of events for the BSA at 40 mg/mL is also provided in Table 10.

TABLE 10

Summary of sequential order of events for BSA at 40 mg/mL

Event Asynchronous and Synchronous plot analysis

| 1 | Asp⁻ (1567 cm$^{-1}$) → Asp⁻ (1584 cm$^{-1}$) |
| 2 | Lys (1530 cm$^{-1}$), Lys (1525.5 cm$^{-1}$) → β-sheet/Arg (1629.5 cm$^{-1}$) |
| 3 | Glu⁻ (1541.7 cm$^{-1}$) → α-helix (1653.9 cm$^{-1}$) |
| 4 | Asp⁻ (1584 cm$^{-1}$) → Glu⁻ (1541.7 cm$^{-1}$) |
| 5 | β-sheet/Arg (1629 cm$^{-1}$) → His (1606.5cm$^{-1}$) |
| 6 | Tyr (1518.5 cm$^{-1}$) → His (1606.5 cm$^{-1}$) |
| 7 | α-helix (1652 cm$^{-1}$) → Asp⁻ (1576.4 cm$^{-1}$) |
| 8 | Arg (1672.4 cm$^{-1}$) → Glu⁻ (1559 cm$^{-1}$) |
| 9 | His (1606.5 cm$^{-1}$) → β-turn (1684 cm$^{-1}$) |
| 10 | Glu⁻ (1559 cm) → Asp⁻ (1576.4 cm) |
| 11 | β-turn (1698 cm$^{-1}$) → β-turn (1684 cm$^{-1}$) |

The aspartates (1567 cm$^{-1}$) and glutamates (1584 cm$^{-1}$) located within the helical regions (1653.9 cm$^{-1}$) that are involved in salt bridge interactions with lysines (1530.0 and 1525.5 cm$^{-1}$) are perturbed first; followed by the β-sheets (1629.6 cm$^{-1}$), then the tyrosines (1518 cm$^{-1}$) and histidines (1606.5 cm$^{-1}$) within the antiparallel β-sheets (1629.6 cm$^{-1}$) β-turns (1698 cm$^{-1}$) are perturbed. Finally at high temperature the salt bridge interactions involving arginines with glutamates (1560 cm$^{-1}$) and aspartates (1576.4 cm$^{-1}$) located close to β-turns (1684.0 cm$^{-1}$) are perturbed.

Figure 27:
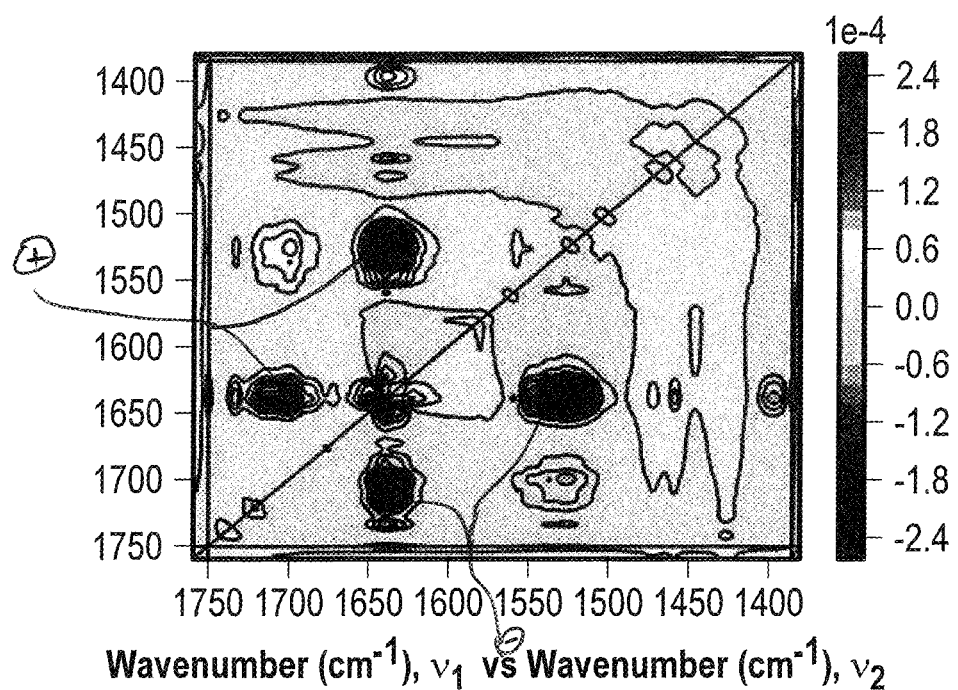
FIG. 27 shows an asynchronous 2D IR co-distribution analysis plot for BSA 40 mg/mL in $H_2O$ under thermal stress within the temperature range of 24-60° C. and spectral region of 1750-1380 $cm^{-1}$.

FIG. 27 shows an asynchronous 2D IR co-distribution analysis plot for BSA 40 mg/mL in $H_2O$ under thermal stress within the temperature range of 24-60° C. and spectral region of 1750-1380 cm$^{-1}$. In the case of the BSA 40 mg/mL, its thermal stress was related to the perturbation of the glutamates within the n-turns and the helical regions.

Example 4

Samples including a mixture of NIST mAb and BSA in $H_2O$ were studied for analysis according to methods described herein. Samples were added to cells of a $CaF_2$ slide for data acquisition using a QCL microscope. The applied perturbation was temperature within the range of 24-60° C. with 4° C. temperature intervals. QCL spectral data was acquired using a 4× magnitude objective at 4 cm$^{-1}$ with data encoded every 0.5 cm$^{-1}$ and baseline corrected.

Figure 28A:
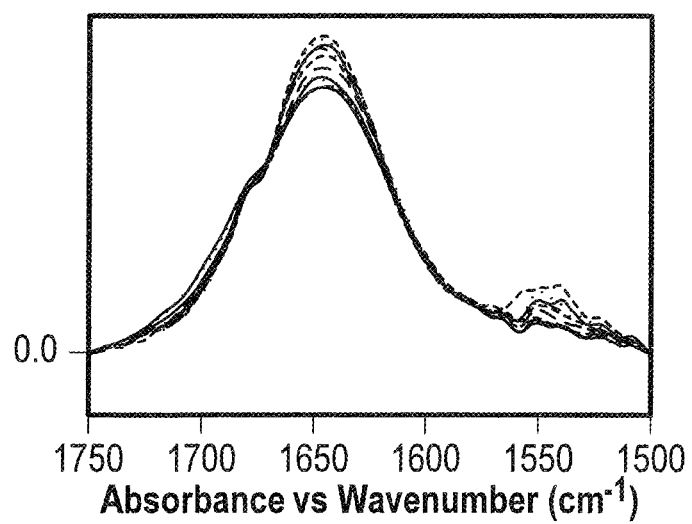
FIG. 28A shows overlaid spectra showing both the amide I and II bands for NIST mAb/BSA (1:2, mol ratio) mixture in the spectral region of 1750-1500 $cm^{-1}$ acquired within the temperature range of 24-60° C. in $H_2O$.
Figure 28B:
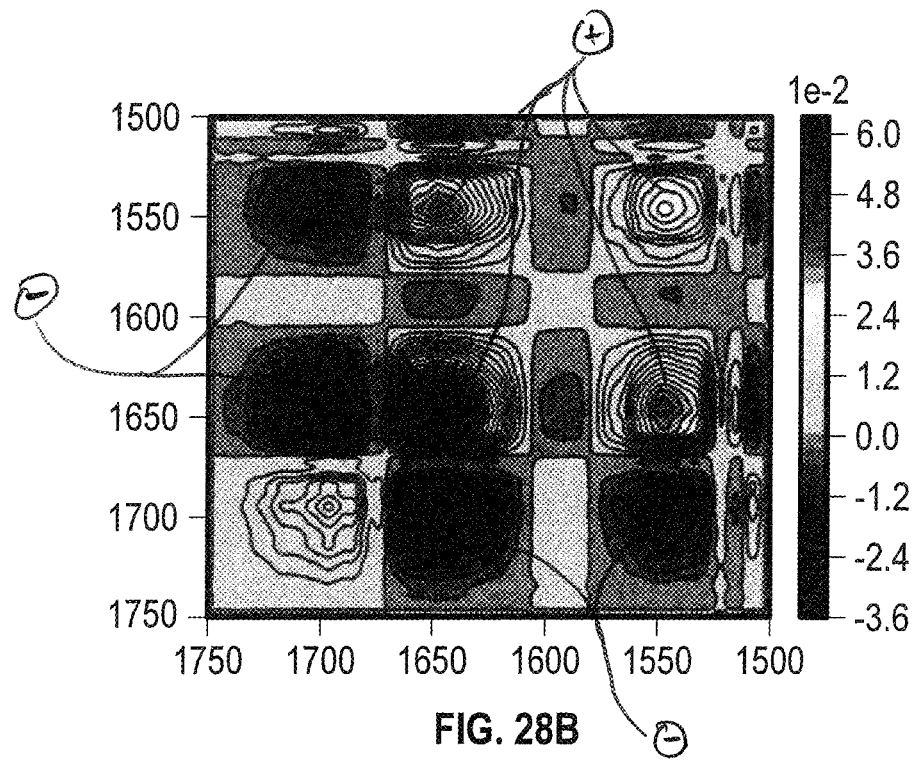
FIGS. 28B and 28C show 2D IR correlation analysis plots (FIG. 28B: synchronous, FIG. 28C: asynchronous) for the sample of FIG. 28A.
Figure 28C:
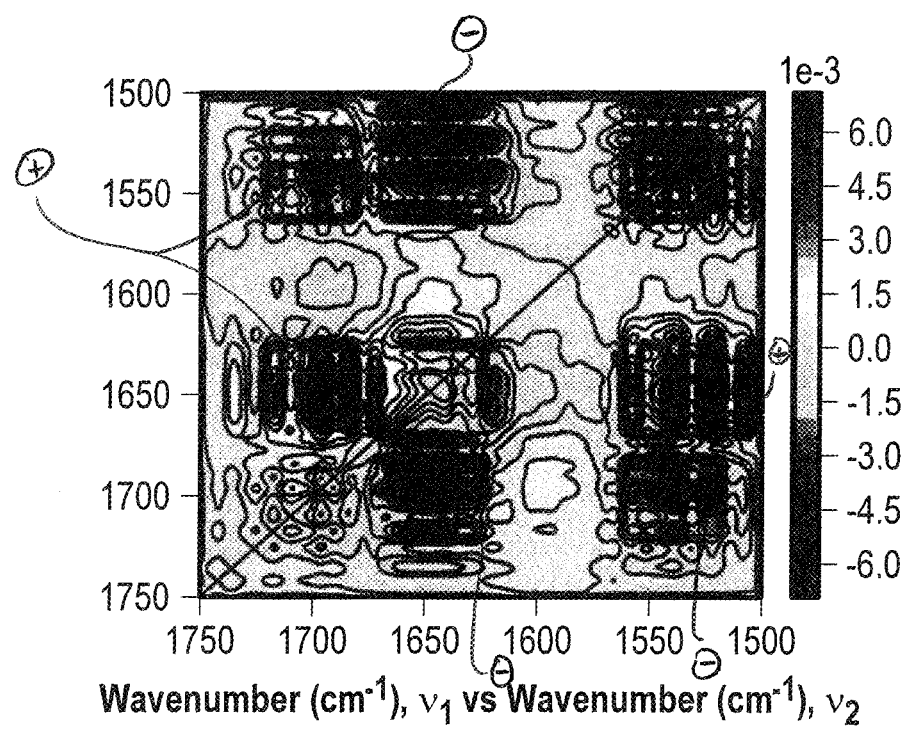

As shown in FIG. 28A, QCL spectra of NIST mAb/BSA (1:2, mol ratio) mixture in the spectral region of 1750-1500 cm$^{-1}$ was acquired within the temperature range of 24-60° C. in $H_2O$. FIG. 28A shows overlaid spectra showing the amide I and II bands. Based on the spectral data synchronous (FIG. 28B) and asynchronous (FIG. 28C) 2D IR correlation analysis plots were generated. Overall the synchronous plot contour exhibited features that are distinguishable both for NIST mAb and that of BSA pure components.

Peak assignments of NIST mAb/BSA are provided in Table 11.

TABLE 11

Summary of peak assignments of NIST mAb/BSA

| Protein | Peak Assignment | Peak Position (cm$^{-1}$) |
|---|---|---|
| NIST mAb | β-turn | 1692 |
| NIST mAb | β-turn | 1681.6 |
| NIST mAb | Arg | 1668 |
| BSA | α-helix | 1653.9 |
| NIST mAb | α-helix | 1652 |
| NIST mAb | β-sheet | 1635 |
| BSA | β-sheet/Arg | 1629.6 |
| NIST mAb | Agg | 1618 |

TABLE 11-continued

Summary of peak assignments of NIST mAb/BSA

| Protein | Peak Assignment | Peak Position (cm$^{-1}$) |
|---|---|---|
| BSA | His | 1606.5 |
| NIST mAb | Asp$^-$ | 1573 |
| BSA | Asp$^-$ | 1567.1 |
| BSA | Glu$^-$ | 1559 |
| NIST mAb | Glu$^-$ | 1542 |
| BSA | Glu$^-$ | 1541.7 |
| BSA | Lys | 1525.5 |

Note:
Aggregation (Agg)

Example 5

Samples including Lysozyme in H$_2$O were studied for analysis according to methods described herein. Custom CaF$_2$ slide cells were used with 7 μm path-length for samples in H$_2$O. The applied perturbation was temperature within the range of 24-60° C. with 4° C. temperature intervals. QCL IR spectral data was acquired using a 4× magnitude objective at 4 cm$^{-1}$ with data encoded every 0.5 cm$^{-1}$ and baseline corrected.

Below is an amino acid sequence for the Lysozyme analyzed.

(SEQ ID NO: 8)
KVFGRCELAAAMKRHGLDNYRGYSLGNWVCAAKFESNFNTQATNRNTD

GSTDYGILQINSRWWCNDGRTPGSRNLCNIPCSALLSSDITASVNCAK

KIVSDGNGMNAWVAWRNRCKGTDVQAWIRGCRL

Assignment of amino acid side chains for the sample is provided in Table 12.

TABLE 12

Assignment of amino acid side chains for Lysozyme in H$_2$O

| item | side chain | code | vibrational mode | position (cm$^{-1}$) | number of residues in sequence |
|---|---|---|---|---|---|
| 1 | Tyr | Y | ν (C=C) | 1518 | 3 |
| 2 | Glu$^-$ | E | ν (COO—) | 1543-1560 | 5 |
| 3 | Asp$^-$ | D | ν (COO—) | 1570-1574 | 7 |
| 4 | His | H | ν (C=C) | 1596 | 1 |
| 5 | C-term end | | ν (COO—) | 1598 | 1 |
| 6 | Arg | R | ν$_{as}$ (CN$_3$H$_5^+$) | 1673 | 11 |
| 7 | Arg | R | ν$_s$ (CN$_3$H$_5^+$) | 1633 | 11 |
| 8 | Lys | K | δ$_{as}$ (NH$_3^+$) | 1629 | 6 |
| 9 | Lys | K | δ$_s$ (NH$_3^+$) | 1526 | 6 |
| 10 | Asn | N | ν (C=O) | 1678 | 15 |
| 11 | Gln | Q | ν (C=O) | 1670 | 4 |

Figure 29B:
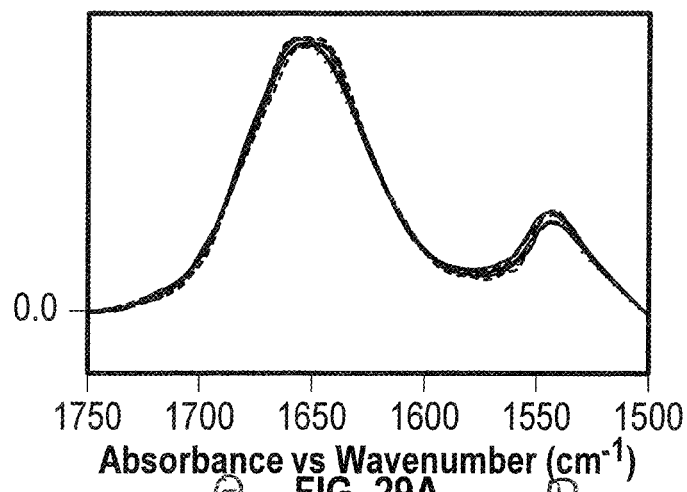
FIGS. 29B and 29C show 2D IR correlation analysis plots (FIG. 29B: synchronous, FIG. 29C: asynchronous) for the sample of FIG. 29A.
Figure 29B:
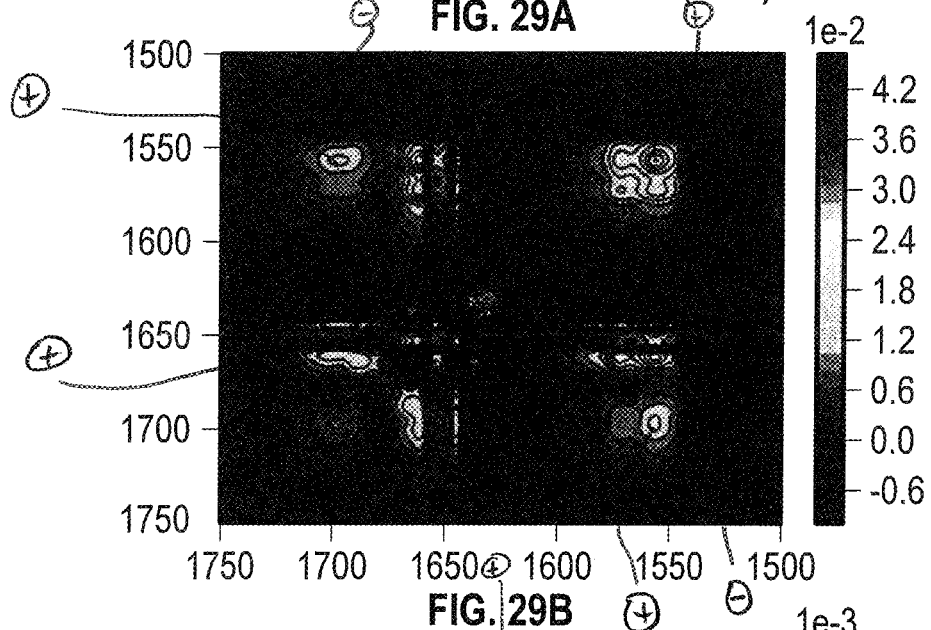
Figure 29C:
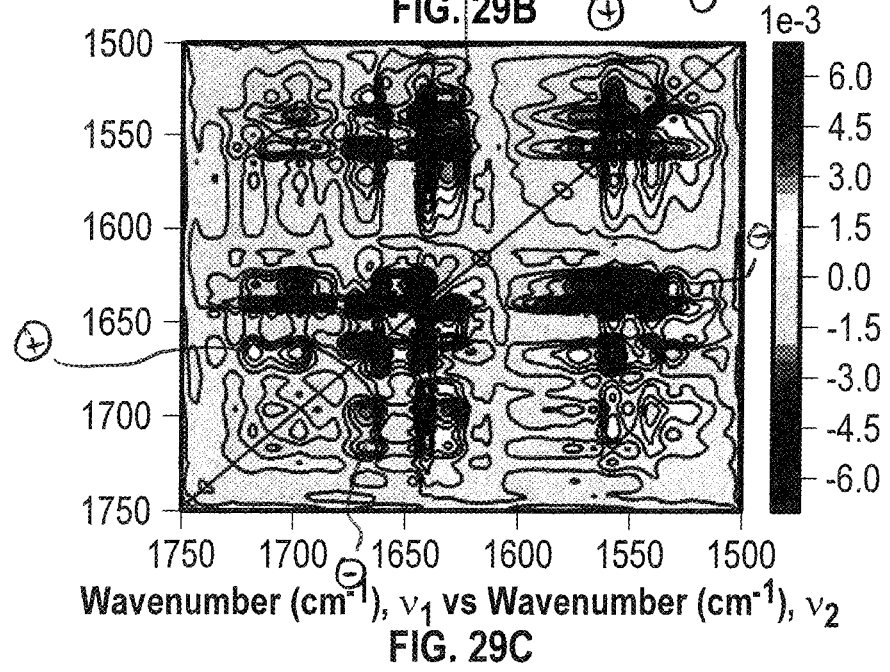

As shown in FIG. 29A, QCL spectra of Lysozyme at 600 mg/mL in the spectral region of 1750-1500 cm$^{-1}$ was acquired within the temperature range of 24-60° C. in H$_2$O. FIG. 29A shows overlaid spectra showing the amide I and II bands. Based on the spectral data synchronous (FIG. 29B) and asynchronous (FIG. 29C) 2D IR correlation analysis plots were generated. Correlation between the helical regions of the protein and the β-turns can be established due to the thermal stress. Also, the weak interactions between glutamate, aspartate and arginine, lysine, histidine residues are critical to the stability of Lysozyme as established by the correlations observed in both the synchronous and asynchronous plot. No aggregation was observed for this protein.

Peak assignments of Lysozyme at 600 mg/mL are provided in Table 13.

TABLE 13

Summary of peak assignments of Lysozyme at 600 mg/mL

| Peak Assignment | Peak Position (cm$^{-1}$) |
|---|---|
| β-turn | 1698 |
| β-turn | 1683.8 |
| Arg | 1672.4 |
| Arg/Asn/Gln | 1666.6 |
| Hinge loop | 1660.5 |
| α-helix | 1647 |
| β-sheet | 1637.2 |
| Arg | 1628.7 |
| His | 1596.6 |
| Asp$^-$ | 1572.3 |
| Asp$^-$ | 1566.1 |
| Glu$^-$ | 1556.3 |
| Glu$^-$ | 1547.8 |
| Glu$^-$ | 1536.8 |
| Lys | 1526.9 |
| Tyr | 1514.6 |

Figure 30:
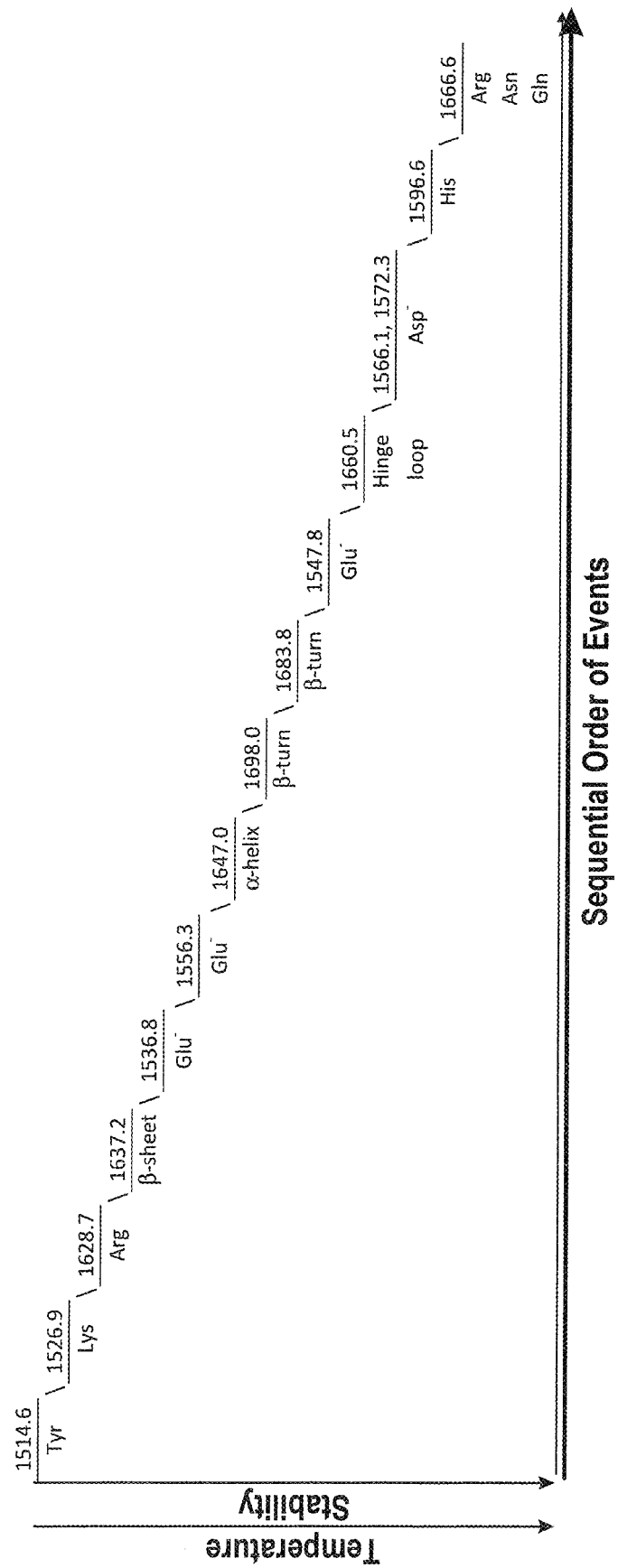
FIG. 30 shows the sequential order of events for Lysozyme at 600 mg/mL in H2O under thermal stress (24-60° C.).

The sequential order of events for Lysozyme at 600 mg/mL under thermal stress within the temperature range of 24-60° C. is shown in FIG. 30. The sequential order of events for the BSA at 40 mg/mL is also provided in Table 14.

TABLE 14

Summary of sequential order of events for Lysozyme at 600 mg/mL

| Event | Asynchronous and Synchronous plot analysis |
|---|---|
| 1 | Tyr (1514.6 cm$^{-1}$) → Lys (1526.9 cm$^{-1}$) |
| 2 | Lys (1526.9 cm$^{-1}$) → β-sheet (1637.2 cm$^{-1}$) |
| 3 | Lys (1526.9 cm$^{-1}$) → Arg (1628.7 cm$^{-1}$) |
| 4 | Arg (1628.7 cm$^{-1}$) → Glu$^-$ (1536.8 cm$^{-1}$) |
| 5 | β-sheet (1637.2 cm$^{-1}$) → Glu$^-$ (1556.3 cm$^{-1}$) |
| 6 | Glu$^-$ (1536.8 cm$^{-1}$) → Glu$^-$ (1556.3 cm$^{-1}$) |
| 7 | Glu$^-$ (1556.3 cm$^{-1}$) → Glu$^-$ (1547.8 cm$^{-1}$) |
| 8 | α-helix (1647 cm$^{-1}$) → β-turn (1683 cm$^{-1}$) |
| 9 | β-turn (1698 cm$^{-1}$) → Arg/Asn/Gln (1666.6 cm$^{-1}$) |
| 10 | Glu$^-$ (1547.8 cm$^{-1}$) → Asp$^-$ (1566.1 cm$^{-1}$, 1572.3 cm$^{-1}$) |
| 11 | Glu$^-$ (1547.8 cm$^{-1}$) → Hinge loop (1660.5 cm$^{-1}$) |
| 12 | Glu$^-$ (1556.3 cm$^{-1}$) → α-helix (1647 cm$^{-1}$) |
| 13 | Hinge loop (1660.5 cm$^{-1}$) → His (1596.6 cm$^{-1}$) |
| 14 | Tyr (1514.6 cm$^{-1}$) → Arg/Asn/Gln (1666.6 cm$^{-1}$) |

The tyrosines (1514.6 cm$^{-1}$) and lysines (1526.9 cm$^{-1}$) are perturbed first, followed by the arginines (1628.7 cm$^{-1}$) then the β-sheets (1637.2 cm$^{-1}$), then the glutamates (1536.8 cm$^{-1}$) within the β-sheets followed by the glutamates (1556 cm$^{-1}$) located within the helical regions (1647.0 cm$^{-1}$) and the β-turns (1698.0 cm$^{-1}$ and 1683.8 cm$^{-1}$) followed by glutamates (1547.8 cm$^{-1}$) the hinge loops (1660.5 cm$^{-1}$) then the aspartates (1566.1, 1672.3 cm$^{-1}$) and a single histidine (1596.6 cm$^{-1}$) presumably interacting with an aspartate by H-bonding interaction located near the N-terminal end and finally the Arg, Asn, Gln all assigned to (1666.6 cm$^{-1}$). No aggregation was observed.

Figure 31:
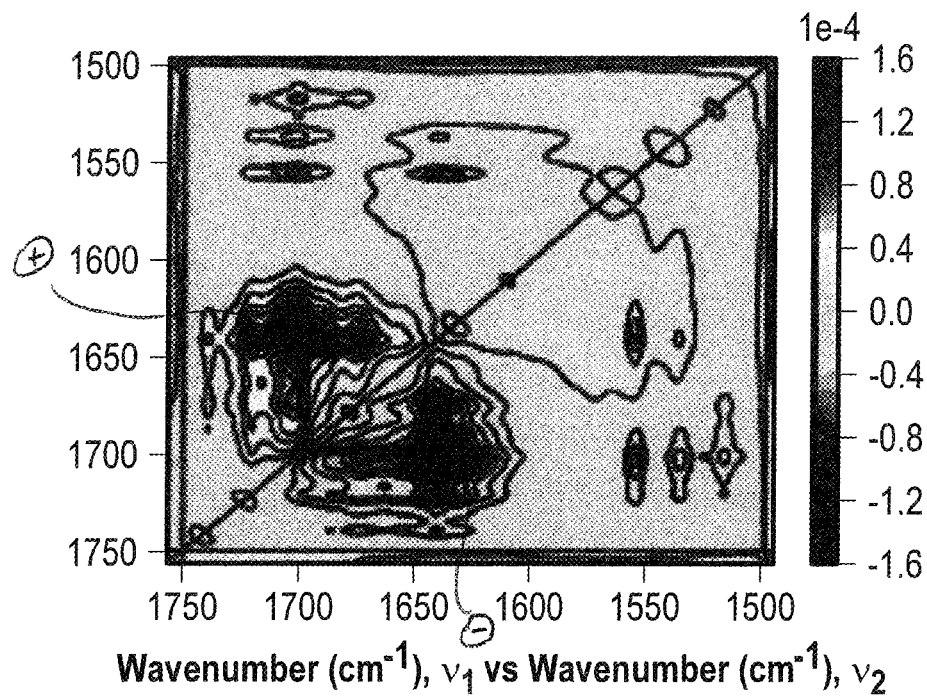
FIG. 31 shows an asynchronous 2D IR co-distribution analysis plot for Lysozyme at 600 mg/mL in $H_2O$ under thermal stress within the temperature range of 24-60° C. and spectral region of 1750-1500 $cm^{-1}$.

FIG. 31 shows an asynchronous 2D IR co-distribution analysis plot for Lysozyme at 600 mg/mL in H$_2$O under thermal stress within the temperature range of 24-60° C. and spectral region of 1750-1500 cm$^{-1}$. In the case of the Lysozyme (600 mg/mL), its thermal stress was related to the perturbation of the, tyrosines located within the hinge loops and lysines and glutamates located near or at the β-turns and helical regions.

Figure 32:
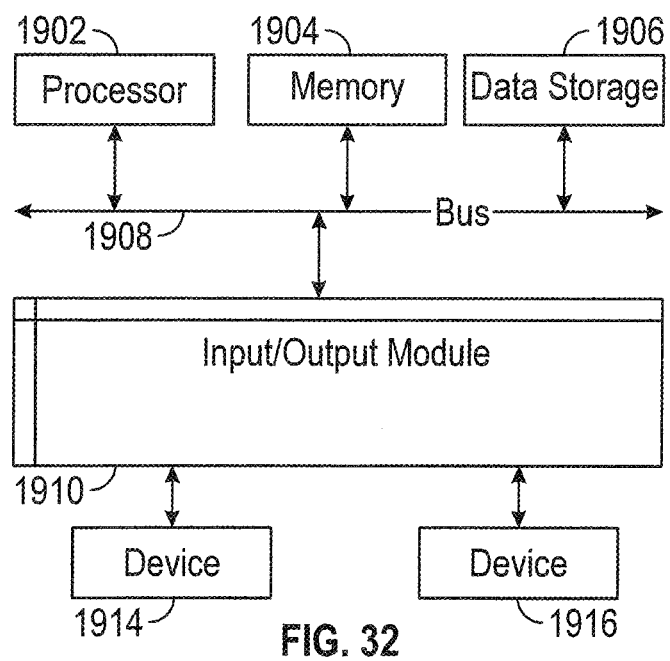
FIG. 32 shows an exemplary diagram of a computing system.

FIG. 32 is a block diagram illustrating an exemplary computer system with which a computing device (e.g., of FIG. 4) can be implemented. In certain embodiments, the computer system 1900 may be implemented using hardware or a combination of software and hardware, either in a dedicated server, or integrated into another entity, or distributed across multiple entities.

The computer system 1900 includes a bus 1908 or other communication mechanism for communicating information, and a processor 1902 coupled with the bus 1908 for processing information. By way of example, the computer system 1900 may be implemented with one or more processors 1902. The processor 1902 may be a general-purpose microprocessor, a microcontroller, a Digital Signal Processor (DSP), an Application Specific Integrated Circuit (ASIC), a Field Programmable Gate Array (FPGA), a Programmable Logic Device (PLD), a controller, a state machine, gated logic, discrete hardware components, and/or any other suitable entity that can perform calculations or other manipulations of information.

The computer system 1900 can include, in addition to hardware, code that creates an execution environment for the computer program in question, e.g., code that constitutes processor firmware, a protocol stack, a database management system, an operating system, or a combination of one or more of them stored in an included memory 1904, such as a Random Access Memory (RAM), a flash memory, a Read Only Memory (ROM), a Programmable Read-Only Memory (PROM), an Erasable PROM (EPROM), registers, a hard disk, a removable disk, a CD-ROM, a DVD, and/or any other suitable storage device, coupled to the bus 1908 for storing information and instructions to be executed by the processor 1902. The processor 1902 and the memory 1904 can be supplemented by, or incorporated in, special purpose logic circuitry.

The instructions may be stored in the memory 1904 and implemented in one or more computer program products, i.e., one or more modules of computer program instructions encoded on a computer readable medium for execution by, or to control the operation of, the computer system 1900, and according to any method well known to those of skill in the art, including, but not limited to, computer languages such as data-oriented languages (e.g., SQL, dBase), system languages (e.g., C, Objective-C, C++, Assembly), architectural languages (e.g., Java, .NET), and/or application languages (e.g., PHP, Ruby, Perl, Python). Instructions may also be implemented in computer languages such as array languages, aspect-oriented languages, assembly languages, authoring languages, command line interface languages, compiled languages, concurrent languages, curly-bracket languages, dataflow languages, data-structured languages, declarative languages, esoteric languages, extension languages, fourth-generation languages, functional languages, interactive mode languages, interpreted languages, iterative languages, list-based languages, little languages, logic-based languages, machine languages, macro languages, metaprogramming languages, multiparadigm languages, numerical analysis, non-English-based languages, object-oriented class-based languages, object-oriented prototype-based languages, off-side rule languages, procedural languages, reflective languages, rule-based languages, scripting languages, stack-based languages, synchronous languages, syntax handling languages, visual languages, wirth languages, and/or xml-based languages. The memory 1904 may also be used for storing temporary variable or other intermediate information during execution of instructions to be executed by the processor 1902.

A computer program as discussed herein does not necessarily correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, subprograms, or portions of code). A computer program can be deployed to be executed on one computer or on multiple computers that are located at one site or distributed across multiple sites and interconnected by a communication network. The processes and logic flows described in this specification can be performed by one or more programmable processors executing one or more computer programs to perform functions by operating on input data and generating output.

The computer system 1900 further includes a data storage device 1906 such as a magnetic disk or optical disk, coupled to the bus 1908 for storing information and instructions. The computer system 1900 may be coupled via an input/output module 1910 to various devices (e.g., devices 1914 and 1916). The input/output module 1910 can be any input/output module. Exemplary input/output modules 1910 include data ports (e.g., USB ports), audio ports, and/or video ports. In some embodiments, the input/output module 1910 includes a communications module. Exemplary communications modules include networking interface cards, such as Ethernet cards, modems, and routers. In certain aspects, the input/output module 1910 is configured to connect to a plurality of devices, such as an input device 1914 and/or an output device 1916. Exemplary input devices 1914 include a keyboard and/or a pointing device (e.g., a mouse or a trackball) by which a user can provide input to the computer system 1900. Other kinds of input devices 1914 can be used to provide for interaction with a user as well, such as a tactile input device, visual input device, audio input device, and/or brain-computer interface device. For example, feedback provided to the user can be any form of sensory feedback (e.g., visual feedback, auditory feedback, and/or tactile feedback), and input from the user can be received in any form, including acoustic, speech, tactile, and/or brain wave input. Exemplary output devices 1916 include display devices, such as a cathode ray tube (CRT) or liquid crystal display (LCD) monitor, for displaying information to the user.

According to certain embodiments, a client device and/or a server can be implemented using the computer system 1900 in response to the processor 1902 executing one or more sequences of one or more instructions contained in the memory 1904. Such instructions may be read into the memory 1904 from another machine-readable medium, such as the data storage device 1906. Execution of the sequences of instructions contained in the memory 1904 causes the processor 1902 to perform the process steps described herein. One or more processors in a multi-processing arrangement may also be employed to execute the sequences of instructions contained in the memory 1904. In some embodiments, hard-wired circuitry may be used in place of or in combination with software instructions to implement various aspects of the present disclosure. Thus, aspects of the present disclosure are not limited to any specific combination of hardware circuitry and software.

Various aspects of the subject matter described in this specification can be implemented in a computing system that includes a back end component (e.g., a data server), or that includes a middleware component (e.g., an application server), or that includes a front end component (e.g., a client computer having a graphical user interface and/or a Web browser through which a user can interact with an implementation of the subject matter described in this specification), or any combination of one or more such back end, middleware, or front end components. The components of the system 1900 can be interconnected by any form or medium of digital data communication (e.g., a communication network). Examples of communication networks include a local area network and a wide area network.

The term "machine-readable storage medium" or "computer readable medium" as used herein refers to any medium or media that participates in providing instructions to the processor 1902 for execution. Such a medium may take many forms, including, but not limited to, non-volatile media, volatile media, and transmission media. Non-volatile media include, for example, optical or magnetic disks, such as the data storage device 1906. Volatile media include dynamic memory, such as the memory 1904. Transmission media include coaxial cables, copper wire, and fiber optics, including the wires that comprise the bus 1908. Common forms of machine-readable media include, for example, floppy disk, a flexible disk, hard disk, magnetic tape, any other magnetic medium, a CD-ROM, DVD, any other optical medium, punch cards, paper tape, any other physical medium with patterns of holes, a RAM, a PROM, an EPROM, a FLASH EPROM, any other memory chip or cartridge, or any other medium from which a computer can read. The machine-readable storage medium can be a machine-readable storage device, a machine-readable storage substrate, a memory device, a composition of matter effecting a machine-readable propagated signal, or a combination of one or more of them.

As used herein, a "processor" can include one or more processors, and a "module" can include one or more modules.

In an aspect of the subject technology, a machine-readable medium is a computer-readable medium encoded or stored with instructions and is a computing element, which defines structural and functional relationships between the instructions and the rest of the system, which permit the instructions' functionality to be realized. Instructions may be executable, for example, by a system or by a processor of the system. Instructions can be, for example, a computer program including code. A machine-readable medium may comprise one or more media.

As used herein, the word "module" refers to logic embodied in hardware or firmware, or to a collection of software instructions, possibly having entry and exit points, written in a programming language, such as, for example C++. A software module may be compiled and linked into an executable program, installed in a dynamic link library, or may be written in an interpretive language such as BASIC. It will be appreciated that software modules may be callable from other modules or from themselves, and/or may be invoked in response to detected events or interrupts. Software instructions may be embedded in firmware, such as an EPROM or EEPROM. It will be further appreciated that hardware modules may be comprised of connected logic units, such as gates and flip-flops, and/or may be comprised of programmable units, such as programmable gate arrays or processors. The modules described herein are preferably implemented as software modules, but may be represented in hardware or firmware.

It is contemplated that the modules may be integrated into a fewer number of modules. One module may also be separated into multiple modules. The described modules may be implemented as hardware, software, firmware or any combination thereof. Additionally, the described modules may reside at different locations connected through a wired or wireless network, or the Internet.

In general, it will be appreciated that the processors can include, by way of example, computers, program logic, or other substrate configurations representing data and instructions, which operate as described herein. In other embodiments, the processors can include controller circuitry, processor circuitry, processors, general purpose single-chip or multi-chip microprocessors, digital signal processors, embedded microprocessors, microcontrollers and the like.

Furthermore, it will be appreciated that in one embodiment, the program logic may advantageously be implemented as one or more components. The components may advantageously be configured to execute on one or more processors. The components include, but are not limited to, software or hardware components, modules such as software modules, object-oriented software components, class components and task components, processes methods, functions, attributes, procedures, subroutines, segments of program code, drivers, firmware, microcode, circuitry, data, databases, data structures, tables, arrays, and variables.

The foregoing description is provided to enable a person skilled in the art to practice the various configurations described herein. While the subject technology has been particularly described with reference to the various figures and configurations, it should be understood that these are for illustration purposes only and should not be taken as limiting the scope of the subject technology.

There may be many other ways to implement the subject technology. Various functions and elements described herein may be partitioned differently from those shown without departing from the scope of the subject technology. Various modifications to these configurations will be readily apparent to those skilled in the art, and generic principles defined herein may be applied to other configurations. Thus, many changes and modifications may be made to the subject technology, by one having ordinary skill in the art, without departing from the scope of the subject technology.

It is understood that the specific order or hierarchy of steps in the processes disclosed is an illustration of exemplary approaches. Based upon design preferences, it is understood that the specific order or hierarchy of steps in the processes may be rearranged. Some of the steps may be performed simultaneously. The accompanying method claims present elements of the various steps in a sample order, and are not meant to be limited to the specific order or hierarchy presented.

As used herein, the phrase "at least one of" preceding a series of items, with the term "and" or "or" to separate any of the items, modifies the list as a whole, rather than each member of the list (i.e., each item). The phrase "at least one of" does not require selection of at least one of each item listed; rather, the phrase allows a meaning that includes at least one of any one of the items, and/or at least one of any combination of the items, and/or at least one of each of the items. By way of example, the phrases "at least one of A, B, and C" or "at least one of A, B, or C" each refer to only A, only B, or only C; any combination of A, B, and C; and/or at least one of each of A, B, and C.

Terms such as "top," "bottom," "front," "rear" and the like as used in this disclosure should be understood as referring to an arbitrary frame of reference, rather than to the ordinary gravitational frame of reference. Thus, a top surface, a bottom surface, a front surface, and a rear surface may extend upwardly, downwardly, diagonally, or horizontally in a gravitational frame of reference.

Furthermore, to the extent that the term "include," "have," or the like is used in the description or the claims, such term is intended to be inclusive in a manner similar to the term "comprise" as "comprise" is interpreted when employed as a transitional word in a claim.

The word "exemplary" is used herein to mean "serving as an example, instance, or illustration." Any embodiment described herein as "exemplary" is not necessarily to be construed as preferred or advantageous over other embodiments.

A reference to an element in the singular is not intended to mean "one and only one" unless specifically stated, but rather "one or more." Pronouns in the masculine (e.g., his) include the feminine and neuter gender (e.g., her and its) and vice versa. The term "some" refers to one or more. Underlined and/or italicized headings and subheadings are used for convenience only, do not limit the subject technology, and are not referred to in connection with the interpretation of the description of the subject technology. All structural and functional equivalents to the elements of the various configurations described throughout this disclosure that are known or later come to be known to those of ordinary skill in the art are expressly incorporated herein by reference and intended to be encompassed by the subject technology. Moreover, nothing disclosed herein is intended to be dedicated to the public regardless of whether such disclosure is explicitly recited in the above description.

While certain aspects and embodiments of the subject technology have been described, these have been presented by way of example only, and are not intended to limit the scope of the subject technology. Indeed, the novel methods and systems described herein may be embodied in a variety of other forms without departing from the spirit thereof. The accompanying claims and their equivalents are intended to cover such forms or modifications as would fall within the scope and spirit of the subject technology.

What is claimed is:

1. A method for processing data representing a characteristic of proteins, peptides, and/or peptoids, the method comprising:

applying a controlled perturbation to the proteins, peptides, and/or peptoids in a solution;

sequentially acquiring spectral images of the proteins, peptides, and/or peptoids in the solution using a quantum cascade laser microscope without the use of exogenous probes or additives, the sequentially acquired spectral images capturing induced changes in spectral intensities as a function of the applied perturbation;

identifying and selecting, in at least one of the acquired spectral images, a region of interest with respect to the applied perturbation;

selecting and analyzing spectral data including data for side chains of amino acids in the proteins, peptides and/or peptoids in the solution for the region of interest in a plurality of the sequentially acquired spectral images, wherein analyzing the spectral data includes analyzing side chain modes of the proteins, peptides, and/or peptoids as internal probes;

applying two-dimensional co-distribution (2DCDS) analysis to generate an asynchronous co-distribution plot for the proteins, peptides, and/or peptoids; and identifying in the asynchronous co-distribution plot at least one cross peak associated with aggregation of the proteins, peptides, and/or peptoids.

2. The method of claim 1, comprising using the at least one cross peak to determine an order of a distributed presence of spectral intensity changes with respect to the applied perturbation.

3. The method of claim 2, wherein using the at least one cross peak comprises:

determining, for two wavenumbers $v_1$ and $v_2$, whether the at least one cross peak corresponding to the two wavenumbers has a positive value; and when the at least one cross peak has a positive value, determining that a presence of spectral intensity at $v_1$ is distributed within an interval of the applied perturbation that is lower than an interval within which a presence of spectral intensity at $v_2$ is distributed.

4. The method of claim 2, wherein using the at least one cross peak comprises:
determining, for two wavenumbers $v_1$ and $v_2$, whether the at least one cross peak corresponding to the two wavenumbers has a negative value; and
when the at least one cross peak has a negative value, determining that a presence of spectral intensity at $v_2$ is distributed within an interval of the applied perturbation that is lower than an interval within which a presence of spectral intensity at $v_1$ is distributed.

5. The method of claim 1, wherein the proteins, peptides, and/or peptoids are in a water ($H_2O$) solution.

6. The method of claim 1, wherein an asynchronous co-distribution intensity in the asynchronous co-distribution plot is represented as a difference in distributions of two spectral signals.

7. The method of claim 1, further comprising:
applying the two-dimensional co-distribution (2DCDS) analysis to generate a synchronous co-distribution plot for the proteins, peptides, and/or peptoids;
identifying, in the synchronous co-distribution plot, synchronous co-distribution peaks associated with aggregation of the proteins, peptides, and/or peptoids; and
using the synchronous co-distribution peaks to determine a degree of overlap of distribution patterns for spectral intensities with respect to the applied perturbation.

8. The method of claim 7, wherein using the synchronous co-distribution peaks comprises:
determining, for two wavenumbers v1 and v2, whether the synchronous co-distribution peaks corresponding to the two wavenumbers are within a range.

9. The method of claim 1, further comprising:
applying two-dimensional correlation (2DCOS) analysis to generate a synchronous correlation plot and an asynchronous correlation plot for the proteins, peptides, and/or peptoids;
identifying in the synchronous correlation plot positive cross peaks that correlate with auto peaks associated with aggregation of the proteins, peptides, and/or peptoids; and
using identified peak intensities of the spectral data to determine an amount of aggregation of the proteins, peptides, and/or peptoids.

10. The method of claim 9, further comprising comparing the amount of aggregation of the proteins, peptides, and/or peptoids to an order of a distributed presence of spectral intensities with respect to the applied perturbation.

11. The method of claim 9, further comprising determining the presence and/or extent of deamination of amino acid side chains in the proteins, peptides, and/or peptoids.

12. The method of claim 9, further comprising determining the stability of domains in the proteins, peptides, and/or peptoids.

13. Non-transitory computer-readable medium comprising instructions which, when executed by one or more computers, cause the one or more computers to:
obtain sequentially acquired spectral images, taken using a quantum cascade laser microscope, of the proteins, peptides, and/or peptoids in a solution without the use of exogenous probes or additives, the sequentially acquired spectral images capturing induced changes in spectral intensities as a function of an applied controlled perturbation;
identify and select, in at least one of the acquired spectral images, a region of interest with respect to the applied perturbation;
select and analyze spectral data including data for side chains of amino acids in the proteins, peptides and/or peptoids in the solution for the region of interest in a plurality of the sequentially acquired spectral images, wherein analyzing the spectral data includes analyzing side chain modes of the proteins, peptides, and/or peptoids as internal probes;
apply two-dimensional co-distribution (2DCDS) analysis to generate an asynchronous co-distribution plot for the proteins, peptides, and/or peptoids; and
identify in the asynchronous co-distribution plot at least one cross peak associated with aggregation of the proteins, peptides, and/or peptoids.

14. The method of claim 1, wherein the applied perturbation is a thermal, electrical potential, concentration, pressure, chemical, agitation, oxidation, or acoustic perturbation.

15. The method of claim 1, wherein the applied controlled perturbation is change in temperature over a temperature range.

16. The method of claim 15, wherein sequentially acquiring spectral images comprises acquiring spectral images at regular temperature intervals.

* * * * *

UNITED STATES PATENT AND TRADEMARK OFFICE
CERTIFICATE OF CORRECTION

PATENT NO. : 10,714,209 B2
APPLICATION NO. : 16/240441
DATED : July 14, 2020
INVENTOR(S) : Belinda Pastrana-Rios and Jose Javier Rodriguez-Toro Page 1 of 1

It is certified that error appears in the above-identified patent and that said Letters Patent is hereby corrected as shown below:

In the Specification

Please add the following paragraph, immediately after Column 1, Lines 4-14 of the RELATED APPLICATIONS, and immediately before the SEQUENCE LISTING heading:

-- STATEMENT REGARDING FEDERALLY SPONSORED RESEARCH
This invention was made with Government support under Award No. 1632420 awarded by the National Science Foundation. The Government has certain rights in this invention. --

Signed and Sealed this
Twentieth Day of October, 2020

Andrei Iancu
*Director of the United States Patent and Trademark Office*